(12) United States Patent
Mäntylä et al.

(10) Patent No.: US 7,816,129 B2
(45) Date of Patent: Oct. 19, 2010

(54) PRODUCTION AND SECRETION OF PROTEINS OF BACTERIAL ORIGIN IN FILAMENTOUS FUNGI

(75) Inventors: Arja Mäntylä, Helsinki (FI); Marja Paloheimo, Vantaa (FI); Raija Lantto, Klaukkala (FI); Richard Fagerström, Espoo (FI); Tarja Lahtinen, Vantaa (FI); Pirkko Suominen, Helsinki (FI); Jari Vehmaanperä, Klaukkala (FI)

(73) Assignee: AB Enzymes GmbH, Darmstadt (DE)

( * ) Notice: Subject to any disclaimer, the term of this patent is extended or adjusted under 35 U.S.C. 154(b) by 851 days.

(21) Appl. No.: 10/286,993

(22) Filed: Aug. 13, 2002

(65) Prior Publication Data

US 2003/0148453 A1   Aug. 7, 2003

Related U.S. Application Data

(63) Continuation of application No. 09/120,804, filed on Jul. 23, 1998, now abandoned, which is a continuation of application No. PCT/FI97/00037, filed on Jan. 24, 1997, which is a continuation-in-part of application No. 08/590,563, filed on Jan. 26, 1996, now Pat. No. 6,300,114, which is a continuation-in-part of application No. 08/468,812, filed on Jun. 6, 1995, now Pat. No. 5,935,836, which is a continuation-in-part of application No. 08/332,412, filed on Oct. 31, 1994, now abandoned, which is a continuation-in-part of application No. 08/282,001, filed on Jul. 29, 1994, now abandoned.

(51) Int. Cl.
| | |
|---|---|
| C12N 15/00 | (2006.01) |
| C12N 9/00 | (2006.01) |
| C12N 9/24 | (2006.01) |
| C12N 9/30 | (2006.01) |
| C07H 21/04 | (2006.01) |

(52) U.S. Cl. .................. 435/320.1; 435/183; 435/200; 435/203; 536/23.2

(58) Field of Classification Search .................. 435/183, 435/200, 203, 320.1; 536/23.2
See application file for complete search history.

(56) References Cited

U.S. PATENT DOCUMENTS

| 5,298,405 A | 3/1994 | Nevalainen et al. |
|---|---|---|
| 5,306,633 A | 4/1994 | Gottschalk et al. |
| 5,364,770 A | 11/1994 | Berka et al. |
| 5,437,992 A | 8/1995 | Bodie et al. |
| 5,578,463 A | 11/1996 | Berka et al. |
| 5,661,021 A | 8/1997 | Buchert et al. |
| 5,679,543 A | 10/1997 | Lawlis |
| 5,871,730 A | 2/1999 | Brzezinski et al. |
| 5,935,836 A | 8/1999 | Vehmaanperä et al. |
| 6,004,785 A | 12/1999 | Berka et al. |
| 6,228,629 B1 | 5/2001 | Paloheimo et al. |
| 6,265,204 B1 | 7/2001 | Ward |
| 6,300,114 B1 | 10/2001 | Mäntylä et al. |
| 6,506,593 B2 | 1/2003 | Mäntylä et al. |
| 6,667,170 B1 | 12/2003 | Mäntylä et al. |

FOREIGN PATENT DOCUMENTS

| DE | 40 00 558 | | 7/1990 |
|---|---|---|---|
| EP | 0 137 280 | A1 | 8/1984 |
| EP | 0 215 594 | | 3/1987 |
| EP | 0 238 023 | | 9/1987 |
| EP | 0 244 234 | | 11/1987 |
| EP | 0 262 040 | | 3/1988 |
| EP | 0 334 739 | | 9/1989 |
| EP | 0 351 655 | | 1/1990 |
| EP | 0 383 999 | | 8/1990 |
| EP | 0 386 888 | | 9/1990 |
| EP | 0 395 792 | | 11/1990 |
| EP | 0 429 628 | | 6/1991 |
| EP | 0 463 706 | | 1/1992 |
| EP | 0 473 545 | | 3/1992 |
| EP | 0 513 140 | | 11/1992 |
| EP | 0 489 104 | | 12/1993 |

(Continued)

OTHER PUBLICATIONS

Nyyssonene et al. Biotechnology (N Y). May 1993;11(5):591-5.*
Srivastava et al. FEMS Microbiol Lett. Mar. 1, 1991;78(2-3):201-5.*
Aho. FEBS Lett. Oct. 7, 1991;291(1):45-9.*
Chica et al. Curr Opin Biotechnol. Aug. 2005;16(4):378-84.*
Paloheimo et al. Appl Environ Microbiol. Dec. 2003;69(12):7073-82.*
Aho, S., et al., "Monoclonal antibodies against core and cellulose-binding domains of *Trichoderma reesei* cellobiohydrolases I and II and endoglucanase I," *Eur. J. Biochem.* 200:643-649, Springer International (1991).
Archer, D., et al., "Strategies for Improving Heterologous Protein Production from Filamentous Fungi," *Antonie van Leeuwenhoek* 65:245-250, Kluwer Academic Publishers (April 1994).

(Continued)

*Primary Examiner*—Christian L Fronda
(74) *Attorney, Agent, or Firm*—Sterne, Kessler, Goldstein & Fox P.L.L.C.

(57) ABSTRACT

The present invention is related to an improved production of bacterial proteins in filamentous fungus, e.g. in *Trichoderma* and *Aspergillus*. The improvement is achieved by constructing expression vectors, which comprise the bacterial protein encoding DNA sequences fused in frame with a DNA sequence encoding a filamentous fungus secretable protein or one or more functional domains of said protein. Filamentous fungus hosts transformed with such expression vectors secrete the desired proteins or enzymes, especially xylanases or cellulases originating from bacteria or more preferably from actinomycetes into the culture medium of the host. The desired proteins or enzymes can be used directly from the culture medium after separation of host cells or recovered and treated using down-stream processes, which are appropriate for the respective application. Xylanases or cellulases from actinomycetes produced using the above expression vectors are most suitable for treating plant derived materials e.g. in pulp and paper industries.

27 Claims, 31 Drawing Sheets

FOREIGN PATENT DOCUMENTS

| GB | 2 249 096 | | 4/1992 |
|----|-----------|---|--------|
| WO | WO 85/04672 | | 10/1985 |
| WO | WO 89/01969 | | 3/1989 |
| WO | WO 89/08738 | | 9/1989 |
| WO | WO 90/15860 | | 12/1990 |
| WO | WO 91/02791 | | 3/1991 |
| WO | WO 91/05908 | | 5/1991 |
| WO | WO 92/01797 | | 2/1992 |
| WO | WO 92/03540 | | 3/1992 |
| WO | WO 93/24621 | | 12/1993 |
| WO | WO 93/24622 | * | 12/1993 |
| WO | WO 93/25671 | | 12/1993 |
| WO | WO 93/25693 | | 12/1993 |
| WO | WO 94/21785 | | 9/1994 |
| WO | WO 95/12668 | | 5/1995 |
| WO | WO 95/18219 | | 7/1995 |
| WO | WO 95/27779 | | 10/1995 |
| WO | WO 95/34662 | | 12/1995 |
| WO | WO 97/22692 A1 | | 6/1997 |
| WO | WO 97/27306 | | 7/1997 |
| WO | WO 98/31821 A2 | | 7/1998 |
| WO | WO 98/31821 A3 | | 7/1998 |

OTHER PUBLICATIONS

Bailey, M.J., et al., "Interlaboratory testing of methods for assay of xylanase activity," *J. Biotech.* 23:257-270, Elsevier Science Publishers B.V. (1992).

Bajpai, P., and Bajpai, P.K., "Biobleaching of Kraft Pulp," *Proc. Biochem.* 27:319-325, Elsevier Science Publishers Ltd. (1992).

Benson, S.A., "A Rapid Procedure for Isolation of DNA Fragments from Agarose Gels," *BioTech.* 2:66-67, Eaton Publishing Company (1984).

Boel, E., et al., "Glucoamylases G1 and G2 from *Aspergillus niger* are synthesized from two different but closely related mRNAs," *EMBO J.* 3:1097-1102, IRL Press Limited (1984).

Boel, E., et al., "Two different types of intervening sequences in the glucoamylase gene from *Aspergillus niger*," *EMBO J.* 3:1581-1585, IRL Press Limited (1984).

Boucher, F., et al., "Complete nucleotide sequence of the xylanase gene from the yeast *Cryptococcus albidus*," *Nucl. Acids Res.* 16:9874, IRL Press Limited (1988).

Drocourt, D., et al., "Cassettes of the *Streptoalloteichus hindustanus ble* gene for transformation of lower and higher eukaryotes to phleomycin resistance," *Nucl. Acids Res.* 18:4009, Oxford University Press (1990).

Ethier, J.-F., "Isolement d'actinomycetes thermophiles et clonage de genes de xylanase," M.Sc. Thesis, UMI Dissertation Services from Proquest (1992).

Ethier, J.-F., et al., "Cloning and characterization of two xylanase genes from *Actinomadura* sp. FC7, a newly isolated thermophilic actinomycete," In: *Industrial Microorganisms: Basic and Appl. Mol. Genet.*, Baltz, R. H., et al., eds., Blackwell Publishers (Proc. 5th ASM Conf. Gen. Mol. Biol. Indust. Microorg., Oct. 11-15, 1992. Bloomington, IN, poster C25).

Ethier, J.-F., et al., "Cloning of two xylanase genes from the newly isolated actinomycete *Actinomadura* sp. strain FC7 and characterization of the gene products," *Can. J. Microbiol.* 40:362-368, National Research Council Canada (May 1994).

Farrell, R.L., et al., "New bleach sequences of kraft pulp using white white-rot fungi," *Lignocellulosics* pp. 305-315, Ellie Horwood (1992).

Georgiou, G., "Optimization the Production of Recombinant Proteins in Microorganisms," *AIChE J.* 34:1233-1248, American Institute of Chemical Engineers (1988).

Ghangas, G.S., et al., "Cloning of a *Thermomonospora fusca* Xylanase Gene and Its Expression in *Escherichia coli* and *Streptomyces lividans*," *J. Bacteriol.* 171:2963-2969, American Society for Microbiology (1989).

Greiner-Mai, E., et al., "Morphological and Biochemical Characterization and Emended Descriptions of Thermophilic Actinomycetes Species," *System. Appl. Microbiol.* 9:97-109, G. Fischer Verlag (1987).

Gwynne, D.I., et al., "Genetically Engineered Secretion of Active Human Interferon and a Bacterial Endoglucanase from *Aspergillus Nidulans*," *Bio/Technology* 5:713-719, Nature Publishing Company (1987).

Gwynne, D.I., et al., in Aspergillus: Biology and Industrial Applications, Bennett et al., eds. Butterworth-Heinemann, Boston, pp. 203-214 (1992).

Harkki, A., et al., "A Novel Fungal Expression System: Secretion of Active Calf Chymosin From the Filamentous Fungus *Trichoderma Reesei*," *Biotechnology* 7:596-603, Nature Publishing Company (1989).

Harkki, A., et al., "Genetic engineering of *Trichoderma* to product strains with novel cellulase profiles," *Enzyme Microb. Technol.* 13:227-233, Butterworth-Heinemann (1991).

Harpin, S., "Cloning and characterization of xylanase genes of the actinomycetes Actinomadura sp. FC7," M.Sc. Thesis, (1993).

Harris, E.L.V., et al., In *Protein Purification Methods: A Practical Approach*, Harris, E.L.V., and Angal, S., eds., IRL Press, Oxford, England (1989).

Holtz, C., et al., "Production and properties of xylanases from thermophilic actinomycetes," *Antonie van Leeuwenhoek* 59:1-7, Kluwer Academic Publishers (1991).

Hynes, M.J., et al., "Isolation of Genomic Clones Containing the *amdS* Gene of *Aspergillus nidulans* and Their Use in the Analysis of Structural and Regulatory Mutations," *Mol. Cell. Biol.* 3:1430-1439, American Society for Microbiology (1983).

Irwin, D.C., et al., "Activity Studies of Eight Purified Cellulases: Specificity, Synergism, and Binding Domain Effects," *Biotechnol. & Bioengin.* 42:1002-1013, John Wiley & Sons, Inc. (Oct. 1993).

Irwin, D., at al., "Characterization and Sequence of a *Thermomonospora fusca* Xylanase," *Appl. Environ. Microbiol.* 60:763-770, American Society for Microbiology (Mar. 1994).

Ito, K., et al., "Cloning and Sequencing of the *xynA* Gene Encoding Xylanase A of *Aspergillus kawachii*," *Biosci. Biotech. Biochem.* 56:906-912, Japan Society for Bioscience, Biotechnology, and Agrochemistry (1992).

Joutsjoki, V.V., et al., "Transformation of *Trichoderma reesei* with the *Hormoconis resinae* glucoamylase P (*gam*P) gene: production of a heterologous glucoamylase by *Trichoderma reesei*," *Curr. Genet.* 24:223-228, Springer-Verlag (Sep. 1993).

Jurasek, L., "Direct biological bleaching of pulps," *Lignocellulosics* pp. 317-325, Ellis Horwood (1992).

Kalkkinen, N., and Tilgmann, C., "A Gas-Pulsed-Liquid-Phase Sequencer Constructed from a Beckman 890D Instrument by Using Applied Biosystems Delivery and Cartridge Blocks," *J. Protein Chem.* 7:242-243, Plenum Press (1988).

Kantelinen, A., et al., "Hemicellulases and their Potential Role in Bleaching," in *1988 International Pulp Bleaching Conference*, Tappi Proceedings, pp. 1-9 (1988).

Karhunen, T., et al.,"High frequency one-step gene replacement in *Trichoderma reesei*. I. Endoglucanase I overproduction," *Mol. Gen. Genet.* 241:515-522, Springer-Verlag (Dec. 1993).

Kelly, J.M., and Hynes, M.J., "Transformation of *Aspergillus niger* by the *amdS* gene of *Aspergillus nidulans*," *EMBO J.* 4:475-479, European Molecular Biology Organization/IRL Press (1985).

Korman, D.R., et al., "Cloning, characterization, and expression of two α-amylase genes from *Aspergillus niger* var. *awamori*," *Curr. Genet.* 17:203-212, Springer-Verlag (1990).

Kroppenstedt, R.M., et al., "Taxonomic Revision of the Actinomycete Genera *Actinomadura* and *Microtetraspora*," *System. Appl. Microbiol.* 13:148-160, Gustav Fischer Verlag (1990).

Lantto, R., et al., "Use of Thermostable Xylanases in Softwood Kraft Pulp Bleaching," Presented at the 8th Int. Symp. on Wood and Pulping Chemistry, Jun. 6-9, 1995, published by Jyvaskyla: Gummerus Kirjapaino Oy, Helsinki, Finland, pp. 409-412.

Lao, G., et al., "DNA Sequences of Three β-1, 4-Endoglucanase Genes from *Thermomonospora fusca*," *J. Bacteriol.* 173:3397-3407, American Society for Microbiology (1991).

Lin, L.-L., and Thomson, J.A., "Cloning, sequencing and expression of a gene encoding a 73 kDa xylanase enzyme from the rumen anaerobe *Butyrivibrio fibrisolvens* H17c," *Mol. Gen. Genet.* 228:55-61, Springer-Verlag (1991).

Maat, J., et al., "Xylanases and their application in bakery," In: *Xylans and Xylanases*, J. Visser et al., eds., (Elsevier Science, Amsterdam) pp. 349-360 (1992).

Mattern, I.E., and Punt, P.J., "A vector of *Aspergillus* transformation conferring phleomycin resistance," *Fungal Genet. Newsletter* 35:25, Fungal Genetics Stock Center (1988).

Nyyssönen, E., et al., "Efficient Production of Antibody Fragments by the Filamentous Fungus *Trichoderma reesei*," *Bio/Tech.* 11:591-595, Nature Publishing Company (May 1993).

Onysko, K.A., "Biological Bleaching of Chemical Pulps: A Review," *Biotech. Adv.* 11:179-198, Pergamon Press Ltd. (1993).

Parkkinen, E., et al., "Thermostable Xylanases Produced by a Thermophilic *Microtetraspera flexuosa*," (Text of a Poster Presented at the 7th European Congress in Biotechnology, Feb. 19-23, 1995, Nice, France, Poster MAP-191 ECB7).

Parkkinen, E., et al., "Thermostable Xylanases Produced by a Thermophilic *Microtetraspora flexuosa*," (Abstract of a Poster Presented at the 7th European Congress in Biotechnology, Feb. 19-23, 1995, Nice, France, Poster MAP-191 ECB7).

Penttilä, M., et al., "A versatile transformation system for the cellulolytic filamentous fungus *Trichoderma reesei*," *Gene* 61:155-164, Elsevier Science Publishers B.V. (1987).

Punt, P.J., et al., "Intracellular and extracellular production of proteins in *Aspergillus* under the control of expression signals of the highly expressed *Aspergillus nidulans gpdA* gene," *J. Biotechnol.* 17:19-34, Elsevier Science Publishers B.V. (1991).

Rowlands, R.T., and Turner, G., "Nuclear and Extranuclear Inheritance of Oligomycin Resistance in *Aspergillus nidulans*," *Mol. Gen. Genet.* 126:201-216, Springer-Verlag (1973).

Scheirlinck, T., et al., "Cloning and expression of cellulase and xylanase genes in *Lactobacillus plantarum*," *Appl. Microbiol. Biotechnol.* 33:534-541, Springer-Verlag (1990).

Senior, D.J., and Hamilton, J., "Biobleaching with Xylanases Brings Biotechnology to Reality," *Pulp & Paper* 66:111-114, Miller Freeman Inc. (1992).

Shareck, F., et al., "Sequences of three genes specifying xylanases in *Streptomyces lividans*," *Gene* 107:75-82, Elsevier Science Publishers B.V. (1991).

Shoemaker, S., et al., "Molecular Cloning of Exo-Cellobiohydrolase I Derived from *Trichoderma reesei* Strain L27," *Bio/Tech.* 1:691-696, Nature Publishing Company (1983).

Stålbrand, H., et al., "Cloning and Expression in *Saccharomyces cerevisiae* of a *Trichoderma reesei* β-Mannanase Gene Containing a Cellulose Binding Domain," *Appl. Environ. Microbiol.* 61:1090-1097, American Society for Microbiology (Mar. 1995).

Stangl, H., et al., "Characterization of the *Trichoderma reesei* cbh2 promoter," *Curr. Genet.* 23:115-122, Springer-Verlag (Feb. 1993).

Stoffer, B., et al., "Production, purification and characterization of the catalytic domain of glucoamylase from *Aspergillus niger*," *Biochem. J.* 292:197-202, The Biochemical Society (May 1993).

Suominen, P.L., et al., "High frequency one-step gene replacement in *Trichoderma reesei*. II. Effects of deletions of individual cellulase genes," *Mol. Gen. Genet.* 241:523-530, Springer-Verlag (Dec. 1993).

Svensson, B., et al., "Structure—Function Relationship in Amylases," in *Biotechnology of Amylodextrin Oligosaccharides*, Friedman, R.B., ed., ACS Symposium Series 458, American Chemical Society, Washington, DC (1991).

Teeri, T., et al., "The Molecular Cloning of the Major Cellulase Gene from *Trichoderma reesei*," *Bio/Tech.* 1:696-699, Nature Publishing Company (1983).

Uusitalo, J.M., et al., "Enzyme production by recombinant *Trichoderma reesei*," *J. Biotechnol.* 17:35-50, Elsevier Science Publishers B.V. (1991).

van den Hondel, C.A.M.J.J., et al., "Heterologous Gene Expression in Filamentous Fungi," in *More Gene Manipulations in Fungi*, Bennett, J.W. and Lasure, L.L., eds., Academic Press, Inc., San Diego, CA, pp. 396-428 (1991).

Viikari, L., et al., "Bleaching with Enzymes," in *Proceedings of the Third International Conference on Biotechnology in the Pulp Paper Industry*, Stockholm, pp. 67-69, Swedish Forest Products Research Laboratory and the Swedish Association of Pulp and Paper Engineers (1986).

Viikari, L., et al., "Application of Enzymes in Bleaching," in *Proceedings of the Fourth International Symposium Wood and Pulping Chem.*, Paris, vol. I, pp. 151-154, Jacques Poncet Bresson (1987).

Viikari, L., et al., "Hemicellulases for Industrial Applications," *Biotech. in Agric.* 9:131-182 (Bioconversion of Forest and Agricultural Plant Residues), Saddler, J. ed., CAB Intl. (Jul. 1993).

Viikari, L., et al., "Xylanases in bleaching: From an idea to the industry," *FEMS Microbiol. Rev.* 13:335-350, Elsevier (Mar. 1994).

Whitehead, T.R., and Lee, D.A., "Cloning and Comparison of Xylanase Genes from Ruminal and Colonic *Bacteroides Species*," *Curr. Microbiol.* 23:15-19, Springer-Verlag (1991).

Wick, C.B., "Enzymology Advances Offer Economical and Environmentally Safe Ways to Make Paper," *Gen. Eng. News*, Mary Ann Liebert, Inc. (Nov. 1994).

American Type Culture Collection, Catalogue of Bacteria and Phages, 18th ed., p. 197 (1992).

World Patent Index, Dialog file 351, Abstract of DE 40 00 558, Kunnas, A., et al., "Paper-Making with Application of Pulp Suspension to a Sieve Wire—With Addition of Enzyme to Recirculation Water Passing Through Wire to Cleave Deleterious Dissolved Substances Such as Hemicellulose."

World Patent Index, Dialog file 351, Abstract of EP 262 040, Fuentes, J.L., et al., "Enzymatic Treatment of Paper Pulp Using Cellulase and/or Hemicellulase Enzyme Preparation to Improve Draining."

World Patent Index, Dialog file 351, Abstract of EP 334 739, Fuentes, J.L., and Robert, M., "Paper or Cardboard Production—By Enzyme Treatment of Recycled Fibre Pulp to Improve Draining Characteristics."

International Search Report issued by PCT International Searching Authority for Application No. PCT/FI97/00037 (WO 97/27306), mailed May 8, 1997.

Paloheimo, M., et al., "High-Yield Production of a Bacterial Xylanase in the Filamentous Fungus *Trichoderma reesei* Requires a Carrier Polypeptide with an Intact Domain Structure," *Appl. Environ. Microbiol.* 69:7073-7082, American Society for Microbiology (Dec. 2003).

Stålbrand, H., et al., "Cloning and Expression in *Saccharomyces cerevisiae* of a *Trichoderma reesei* β-Mannanase Gene Containing a Cellulose Binding Domain, " *Appl. Environ. Microbiol.* 61:1090-1097, American Society for Microbiology (Mar. 1995).

Saarelainen, R., et al., "Cloning, sequencing and enhanced expression of the *Trichoderma reesei* endoxylanase II (pI 9) gene xln2," *Mol. Gen. Genet.* 241:497-503, Springer-Verlag (Nov. 1993).

Törrönen, A., et al., "The two major xylanases from *Trichoderma reesei*: characterization of both enzymes and genes," *Biotechnology* 10:1461-1465, Nature Publishing Co. (1992).

Ahn, J.O., et al., "Enhanced secretion of *Bacillus stearothermophilus* L1 lipase in *Saccharomyces cerevisiae* by translational fusion to cellulose-binding domain," *Appl. Microbiol. Biotechnol.* 64:833-839, Springer-Verlag (Jun. 2004).

Gilkes, N.R., et al., "Structural and functional relationships in two families of β-1,4-glycanases," *Eur. J. Biochem.* 202:367-377, Federation of European Biochemical Societies (1991).

Gouka, R.J., et al., "Efficient production of secreted proteins by *Aspergillus*: progress, limitations and prospects," *Appl. Microbiol. Biotechnol.* 47:1-11, Springer-Verlag (Jan. 1997).

Nyyssönen, E., et al., "Protein production by the filamentous fungus *Trichoderma reesei*: secretion of active antibody molecules," *Can. J. Bot.* 73(*Suppl. 1*):S885-S890, The National Research Council of Canada (1995).

Teeri, T.T., et al., "Homologous domains in *Trichoderma reesei* cellulolytic enzymes: gene sequence and expression of cellobiohydrolase II," *Gene* 51:43-52, Elsevier Science Publishers B.V. (1987).

Teeri, T.T., et al., "Domain function in *Trichoderma reesei* cellobiohydrolases," *J. Biotechnol.* 24:169-176, Elsevier Science Publishers B.V. (1992).

Paloheimo, M. et al., "Bacterial Xylanase Production in *Trichoderma reesei*," Poster presented Apr. 6, 2002, at the 6 th European Conference on Fungal Genetics, Pisa, Italy.

Li, X.-L., et al., "Codon Optimization of an A+T Rich Xylanase Gene from the Anaerobic Fungus *Orpinomyces* PC-2 for Expression by *Trichoderma reesei*," Poster T3, presented at the *9th International Workshop on Trichoderma and Gliocladium*, Vienna, Austria (Apr. 2006).

Penttilä, M., et al., "Homology between cellulase genes of *Trichoderma reesei*: complete nucleotide sequence of the endoglucanase I gene," *Gene* 44:253-263, Elsevier Science Publishers B.V. (1986).

Saloheimo, M., et al., "EGIII, a new endoglucanase from *Trichoderma reesei*: the characterization of both gene and enzyme," *Gene* 63:11-21, Elsevier Science Publishers B.V. (1988).

Tomme, P., et al., "Cellulose-Binding Domains: Classification and Properties," in *Enzymatic Degradation of Insoluble Carbohydrates*, Saddler, J.N., et al., eds., American Chemical Society, Washington, D.C., pp. 142-163 (Feb. 1995).

Chen, C.M., et al., "Nucleotide sequence and deduced primary structure of cellobiohydrolase II from *Trichoderma reesei*," *Biotechnology* (N.Y.) 5:274-278, Nature Publishing Group (1987).

Davies, G. and Henrissat, B., "Structures and mechanisms of glycosyl hydrolases," *Structure* 3:853-859, Cell Press (Sep. 1995).

Henrissat, B., "A classification of glycosyl hydrolases based on amino acid sequence similarities," *Biochem. J.* 280:309-316, Portland Press on behalf of the Biochemical Society (1991).

Henrissat, B. and Bairoch, A., "New families in the classification of glycosyl hydrolases based on amino acid sequence similarities," *Biochem. J.* 293:781-788, Portland Press on behalf of the Biochemical Society (Aug. 1993).

Nevalainen, H. and Penttila, M., "Molecular biology of Cellulolytic Fungi," in *Mycota II, Genetics and Biotechnology*, Kück, U., ed., Springer Verlag Berlin Heidelberg, Berlin, Germany, pp. 303-319 (Mar. 1995).

Tomme, P., et al., "Studies of the Cellulolytic System of *Trichoderma reesei* QM 9414," *Eur. J. Biochem.* 170:575-581, Blackwell Publishing (Jan. 1988).

Van Arsdell, J.N., et al., "Cloning, characterization, and expression in *Saccharomyces cerevisiae* of endoglucanase I from *Trichoderma reesei*," *Biotechnology* 5:60-64, Nature Publishing Group (1987).

\* cited by examiner

LANE

LANE

LANE

```
  1  CCCGGGTATTCATGTGAATGATTAGCAACAGTTATGTTACGGAGATATTTCTGAGAGTGTTGACAGGTCGTGAAGTCGGT    80

81  CCGATACTTTCGAGCTAGCTCCGATAGTTTTCGATACGCCGGCACATCGAGCACGTCGGACGAGTCACGCGCCACGTCGG   160

161  TTTTCCGCCGCACGCCGCGCAGAGCGGCCGGAGAACCCCCGCGTGTCCGCGGCATCGGTGCCGGTCCGTCGTTCGCCGCC   240

241  GACCGCGCGCCGGGTCGCGACACGCCAGCCCCCATCGGCCCTTCTTCACGAGGAAGCCGTACATGAACGAACCCCTCACC   320
                                                                     M  N  E  P  L  T

321  ATCACGCAGGCCAGGCGCCGCAGACGCCTCGGCCTCCGGCGCATCGTCACCAGTGCCTTCGCCCTGGCACTCGCCATCGC   400
      I  T  Q  A  R  R  R  R  R  L  G  L  R  R  I  V  T  S  A  F  A  L  A  I  A

401  CGGTGCGCTGCTGCCCGGCACGCCCACGCCGACACCACCATCACCCAGAACCAGACCGGGTACGACAACGGCTACTTCT   480
      G  A  L  L  P  G  T  A  H  A  D  T  T  I  T  Q  N  Q  T  G  Y  D  N  G  Y  F  Y

481  ACTCGTTCTGGACCGACGCGCCCGGGACCGTCTCCATGACCCTCCACTCGGGCGGCAGCTACAGCACCTCGTGGCGGAAC   560
      S  F  W  T  D  A  P  G  T  V  S  M  T  L  H  S  G  G  S  Y  S  T  S  W  R  N

561  ACCGGGAACTTCGTCGCCGGCAAGGGCTGGTCCACCGGGGGACGGCGGACCGTGACCTACAACGCCTCCTTCAACCCGTC   640
      T  G  N  F  V  A  G  K  G  W  S  T  G  G  R  R  T  V  T  Y  N  A  S  F  N  P  S

641  GGGTAACGGCTACCTCACGCTCTACGGCTGGACCAGGAACCCGCTCGTCGAGTACTACATCGTCGAGAGCTGGGGCACCT   720
      G  N  G  Y  L  T  L  Y  G  W  T  R  N  P  L  V  E  Y  Y  I  V  E  S  W  G  T  Y

721  ACCGGCCCACCGGCACCTACAAGGGCACCGTCACCACCGACGGGGAACGTACGACATCTACGAGACCTGGCGGTACAAC   800
      R  P  T  G  T  Y  K  G  T  V  T  T  D  G  G  T  Y  D  I  Y  E  T  W  R  Y  N

801  GCGCCGTCCATCGAGGGCACCCGGACCTTCCAGCAGTTCTGGAGCGTCCGGCAGCAGAAGCGGACCAGCGGCACCATCAC   880
      A  P  S  I  E  G  T  R  T  F  Q  Q  F  W  S  V  R  Q  Q  K  R  T  S  G  T  I  T

881  CATCGGCAACCACTTCGACGCCTGGGCCCGCGCCGGCATGAACCTGGGCAGCCACGACTACCAGATCATGGCGACCGAGG   960
      I  G  N  H  F  D  A  W  A  R  A  G  M  N  L  G  S  H  D  Y  Q  I  M  A  T  E  G

961  GCTACCAGAGCAGCGGTAGCTCCACCGTCTCCATCAGCGAGGGTGGCAACCCCGGCAACCCGGGTAACCCCGGCAACCCC  1040
      Y  Q  S  S  G  S  S  T  V  S  I  S  E  G  G  N  P  G  N  P  G  N  P  G  N  P

1041 GGCAACCCCGGTAACCCGGGTAACCCCGGCGGTGGCTGCGTCGCGACCCTCTCCGCCGGCCAGCAGTGGAGCGACCGCTA  1120
      G  N  P  G  N  P  G  G  G  C  V  A  T  L  S  A  G  Q  Q  W  S  D  R  Y

1121 CAACCTCAACGTCTCGGTCAGCGGCTCGAACAACTGGACGGTCCGGATGGACGTGCCCTACCCGGCCCGCATCATCGCCA  1200
      N  L  N  V  S  V  S  G  S  N  N  W  T  V  R  M  D  V  P  Y  P  A  R  I  I  A  T

1201 CCTGGAACATCCACGCCCAGTGGCCCGAGTCCCAGGTGCTCATCGCCAGACCCAACGGCAACGGCAACAACTGGGGCGTG  1280
      W  N  I  H  A  Q  W  P  E  S  Q  V  L  I  A  R  P  N  G  N  G  N  N  W  G  V

1281 ACGATCCAGCACAACGGCAACTGGACCTGGCCGACGGTCACCTGTACCGCGAACTGAGTTCCCGCCCCCAAAGGTGGCGC  1360
      T  I  Q  H  N  G  N  W  T  W  P  T  V  T  C  T  A  N  *

1361 GGCGGCTCCCGGCCG  1375
```

FIGURE 13

```
  1  TTCGGCAGCCTATTGACAAATTTCGTGAATGTTTCCCACACTTGCTCTGCAGACGGCCCCGCCGATCATGGGTGCACCGG    80

81  TCGGCGGGACCGTGCTCCGACGCCATTCGGGGGTGTGCGCCTGCGGGCGCGGCGTCGATCCCGCGGGGACTCCCGCGGTT   160

161  CCCTTTCCGTGTCCCTCTAATGGAGGCTCAGGCATGGGCGTGAACGCCTTCCCCAGACCCGGAGCTCGGCGGTTCACCGG   240
                                       M  G  V  N  A  F  P  R  P  G  A  R  R  F  T  G

241  CGGGCTGTACCGGGCCCTGGCCGCGGCCACGGTGAGCGTGGTCGGCGTGGTCACGGCCCTGACGGTGACCCAGCCCGCCA   320
      G  L  Y  R  A  L  A  A  A  T  V  S  V  V  G  V  V  T  A  L  T  V  T  Q  P  A  S

321  GCGCCGCGGCGAGCACGCTCGCCGAGGGTGCCGCGCAGCACAACCGGTACTTCGGCGTGGCCATCGCCGCGAACAGGCTC   400
      A  A  A  S  T  L  A  E  G  A  A  Q  H  N  R  Y  F  G  V  A  I  A  A  N  R  L
     <------------- #1696 peptide -------------><------- #1697 peptide -------><---

401  ACCGACTCGGTCTACACCAACATCGCGAACCGCGAGTTCAACTCGGTGACGGCCGAGAACGAGATGAAGATCGACGCCAC   480
      T  D  S  V  Y  T  N  I  A  N  R  E  F  N  S  V  T  A  E  N  E  M  K  I  D  A  T
     ------ #1698 peptide ----------><------- # 1704 peptide ------------>

481  CGAGCCGCAGCAGGGGCGGTTCGACTTCACCCAGGCCGACCGGATCTACAACTGGGCGCGCCAGAACGGCAAGCAGGTCC   560
      E  P  Q  Q  G  R  F  D  F  T  Q  A  D  R  I  Y  N  W  A  R  Q  N  G  K  Q  V  R

561  GCGGCCACACCCTGGCCTGGCACTCGCAGCAGCCGCAGTGGATGCAGAACCTCAGCGGCCAGGCGCTGCGCCAGGCGATG   640
      G  H  T  L  A  W  H  S  Q  Q  P  Q  W  M  Q  N  L  S  G  Q  A  L  R  Q  A  M

641  ATCAACCACATCCAGGGGGTCATGTCCTACTACCGGGGCAAGATCCCGATCTGGGACGTGGTGAACGAGGCGTTCGAGGA   720
      I  N  H  I  Q  G  V  M  S  Y  Y  R  G  K  I  P  I  W  D  V  V  N  E  A  F  E  D

721  CGGAAACTCCGGCCGCCGGTGCGACTCCAACCTCCAGCGCACCGGTAACGATTGGATCGAGGTCGCGTTCCGCACCGCCC   800
      G  N  S  G  R  R  C  D  S  N  L  Q  R  T  G  N  D  W  I  E  V  A  F  R  T  A  R

801  GCCAGGGGGACCCCTCGGCCAAGCTCTGCTACAACGACTACAACATCGAGAACTGGAACGCGGCCAAGACCCAGGCGGTC   880
      Q  G  D  P  S  A  K  L  C  Y  N  D  Y  N  I  E  N  W  N  A  A  K  T  Q  A  V
                                                                       <-------------

881  TACAACATGGTGCGGGACTTCAAGTCCCGCGGCGTGCCCATCGACTGCGTGGGCTTCCAGTCGCACTTCAACAGCGGTAA   960
      Y  N  M  V  R  D  F  K  S  R  G  V  P  I  D  C  V  G  F  Q  S  H  F  N  S  G  N
     -  #1703 peptide --->

961  CCCCGTACAACCCGAACTTCCGCACCACCCTGCAGCAGTTCGCGGCCCTCGGCGTGGACGTCGAGGTCACCGAGCTGGACA  1040
      P  Y  N  P  N  F  R  T  T  L  Q  Q  F  A  A  L  G  V  D  V  E  V  T  E  L  D  I

1041 TCGAGAACGCCCCCGGCCCAGACCTACGCCAGCGTGATCCGGGACTGCCTGGCCGTGGACCGCTGCACCGGCATCACCGTC  1120
      E  N  A  P  A  Q  T  Y  A  S  V  I  R  D  C  L  A  V  D  R  C  T  G  I  T  V
                                                                 <--- # 1699 peptide 1121 TGGGGTGTCCGCGACAGCGACTCCTGGCGCTCGTACCAGAACCCGCTGCTGTTCGACAACAACGGCAACAAGAAGCAGGC  1200
      W  G  V  R  D  S  D  S  W  R  S  Y  Q  N  P  L  L  F  D  N  N  G  N  K  K  Q  A
     ------>
```

FIGURE 14

```
1201  CTACTACGCGGTGCTCGACGCCCTGAACGAGGGCTCCGACGACGGTGGCGGCCCGTCCAACCCGCCGGTCTCGCCGCCGC  1280
       Y  Y  A  V  L  D  A  L  N  E  G  S  D  D  G  G  P  S  N  P  P  V  S  P  P  P

1281  CGGGTGGCGGTTCCGGGCAGATCCGGGGCGTGGCCTCCAACCGGTGCATCGACGTGCCGAACGGCAACACCGCCGACGGC  1360
       G  G  G  S  G  Q  I  R  G  V  A  S  N  R  C  I  D  V  P  N  G  N  T  A  D  G

1361  ACCCAGGTCCAGCTGTACGACTGCCACAGCGGTTCCAACCAGCAGTGGACCTACACCTCGTCCGGTGAGTTCCGCATCTT  1440
       T  Q  V  Q  L  Y  D  C  H  S  G  S  N  Q  Q  W  T  Y  T  S  S  G  E  F  R  I  F

1441  CGGCAACAAGTGCCTGGACGCGGGCGGCTCCAGCAACGGTGCGGTGGTCCAGATCTACAGCTGCTGGGGCGGCGCCAACC  1520
       G  N  K  C  L  D  A  G  G  S  S  N  G  A  V  V  Q  I  Y  S  C  W  G  G  A  N  Q

1521  AGAAGTGGGAGCTCCGGGCCGACGGCACCATCGTGGGCGTGCAGTCCGGGCTGTGCCTCGACGCGGTGGGTGGCGGCACC  1600
       K  W  E  L  R  A  D  G  T  I  V  G  V  Q  S  G  L  C  L  D  A  V  G  G  T

1601  GGCAACGGCACGCGGCTGCAGCTCTACTCCTGCTGGGGCGGCAACAACCAGAAGTGGTCCTACAACGCCTGATCCCCGGC  1680
       G  N  G  T  R  L  Q  L  Y  S  C  W  G  G  N  N  Q  K  W  S  Y  N  A  *

1681  TGATCGACCCTAGTTGAGGCCGTCTCCGGTACGGCACCGTCGGACCGGAGGCGGTCCCTTGTTCGTCCAGGACGGAAGGA  1760

1761  CCGGTCTGAGCAGGCGCGGCGATCGGACACCATGGTGGGAGGCACGAAAGCGGGAGGGGGTCGTATTCCGAGACTCCGGG  1840

1841  AAGTGGAGGTGTTCCTCCACCTGA  1864
```

FIGURE 14 (CONTINUED)

```
         10        20        30        40        50        60
AM50   MGVNAFPRPGARRFTGGLYRALAAATVSVVGVVTALTVTQPASAAASTLAEGAAQHNRYF
       | :|::||||||:    ||| |::|:::::::||:::  ||  ||:|||:::||| :|||
U08894 MPINVMPRPGARK------RALLAGAVGLLTAAAALVAPSPAVAAESTLGAAAAQSGRYF
         10        20        30        40        50

70        80        90        100       110       120
AM50   GVAIAANRLTDSVYTNIANREFNSVTAENEMKIDATEPQQGRFDFTQADRIYNWARQNGK
       |:|||::||:||:||:|||||||| |||||||||||||::|:|:|: ||||||| ||||
U08894 GTAIASGRLNDSTYTTIANREFNMVTAENEMKIDATEPNRGQFNFSSADRIYNWAVQNGK
         60        70        80        90        100       110

130       140       150       160       170       180
AM50   QVRGHTLAWHSQQPQWMQNLSGQALRQAMINHIQGVMSYYRGKIPIWDVVNEAFEDGNSG
       ||||||||||||||| ||| :||||||:||:|||::|:|||  ||||||||||||:|||||
U08894 QVRGHTLAWHSQQPGWMQSLSGSSLRQAMIDHINGVMAHYKGKIVQWDVVNEAFADGNSG
         120       130       140       150       160       170

190       200       210       220       230       240
AM50   RRCDSNLQRTGNDWIEVAFRTARQGDPSAKLCYNDYNIENWNAAKTQAVYNMVRDFKSRG
       |  ||||||||||||||||||||::||:||||||||||||||| ||||:|||||||||| ||
U08894 GRRDSNLQRTGNDWIEVAFRTARNADPNAKLCYNDYNIENWNAKTQGVYNMVRDFKQRG
         180       190       200       210       220       230

250       260       270       280       290       300
AM50   VPIDCVGFQSHFNSGNPYNPNFRTTLQQFAALGVDVEVTELDIENAPAQTYASVIRDCLA
       ||||||||||||||:|||:|||||||||::|||||||::||||||:|::  |||:|::||||
U08894 VPIDCVGFQSHFNSGSPYNSNFRTTLQNFAALGVDVAITELDIQGASPTTYANVVNDCLA
         240       250       260       270       280       290

310       320       330       340       350       360
AM50   VDRCTGITVWGVRDSDSWRSYQNPLLFDNNGNKKQAYYAVLDALNEGSDDGGGPSNPPVS
       |:|| ||||||||:||||| |:|||||:|||||:|| |||:||    :|||:|:
U08894 VSRCLGITVWGVRDTDSWRSDQTPLLFDGNGNKKAAYSAVLNAL-----NGGGTSE----
         300       310       320       330       340

370       380       390       400       410       420
AM50   PPPGGGSGQIRGVASNRCIDVPNGNTADGTQVQLYDCHSGSNQQWTYTSSGEFRIFGNKC
       |||:::::| |:||:|:||:|||||::|:||:|:||:|:|||||||||:| |:|::||||
U08894 PPPASDAGTIKGVGSGRCLDVPNASTSDGVQLQLWDCHGGTNQQWTYTDSQELRVYGNKC
         350       360       370       380       390       400

430       440       450       460       470       480
AM50   LDAGGSSNGAVVQIYSCWGGANQKWELRADGTIVGVQSGLCLDAVGGGTGNGTRLQLYSC
       |||:|::||: |||
U08894 LDAAGTGNGTKVQI
         410
```

FIGURE 15A

```
              10         20         30         40         50         60
AM50    MGVNAFPRPGARRFTGGLYRALAAATVSVVGVVTALTVTQPASAAASTLAEGAAQHNRYF
        ||  |:||:|:||  :   |   ||| :|:|:|::|||:::  |  ||:|||:::||| :|||
M64551  MGSYALPRSGVRRSIRVL---LAALVVGVLGTATALIAPPGAHAAESTLGAAAAQSGRYF
              10         20         30          40         50

70         80         90        100        110        120
AM50    GVAIAANRLTDSVYTNIANREFNSVTAENEMKIDATEPQQGRFDFTQADRIYNWARQNGK
        |:|||::||:||:||:|| ||||  ||||||||||||||:|:|:|:  |||:||||  ||||
M64551  GTAIASGRLSDSTYTSIAGREFNMVTAENEMKIDATEPQRGQFNFSSADRVYNWAVQNGK
              60         70         80         90        100        110

130        140        150        160        170        180
AM50    QVRGHTLAWHSQQPQWMQNLSGQALRQAMINHIQGVMSYYRGKIPIWDVVNEAFEDGNSG
        ||||||||||||| |||:|||::||||||:||:|||::|:|||  ||||||||:||:||
M64551  QVRGHTLAWHSQQPGWMQSLSGRPLRQAMIDHINGVMAHYKGKIVQWDVVNEAFADGSSG
             120        130        140        150        160        170

190        200        210        220        230        240
AM50    RRCDSNLQRTGNDWIEVAFRTARQGDPSAKLCYNDYNIENWNAAKTQAVYNMVRDFKSRG
        |  ||||||:||||||||||||||::||||||||||||:||: |||||:||||||||| ||
M64551  ARRDSNLQRSGNDWIEVAFRTARAADPSAKLCYNDYNVENWTWAKTQAMYNMVRDFKQRG
             180        190        200        210        220        230

250        260        270        280        290        300
AM50    VPIDCVGFQSHFNSGNPYNPNFRTTLQQFAALGVDVEVTELDIENAPAQTYASVIRDCLA
        |||||||||||||:|||:|||||||||:|||||||||::|||||::||| |||:|::|||
M64551  VPIDCVGFQSHFNSGSPYNSNFRTTLQNFAALGVDVAITELDIQGAPASTYANVTNDCLA
             240        250        260        270        280        290

310        320        330        340        350        360
AM50    VDRCTGITVWGVRDSDSWRSYQNPLLFDNNGNKKQAYYAVLDALNEGSDDGGGPSNPPVS
        |:||  ||||||||||||||:|:||||:|:||:||  ||||||      :||::|:||
M64551  VSRCLGITVWGVRDSDSWRSEQTPLLFNNDGSKKAAYTAVLDAL-----NGGDSSEPP--
             300        310        320        330        340        350

370        380        390        400        410        420
AM50    PPPGGGSGQIRGVASNRCIDVPNGNTADGTQVQLYDCHSGSNQQWTYTSSGEFRIFGNKC
         :::|||:||:|:||:|||:|||| ||:|||||:||||||| ||||: |::||:|::|:||
M64551  ----ADGGQIKGVGSGRCLDVPDASTSDGTQLQLWDCHSGTNQQWAATDAGELRVYGDKC
                  360        370        380        390        400

430        440        450        460        470        480
AM50    LDAGGSSNGAVVQIYSCWGGANQKWELRADGTIVGVQSGLCLDAVGGGTGNGTRLQLYSC
        |||:|:||| ||||||||||:|||||:||| |::||||||||||||:||:||| :|||:|
M64551  LDAAGTSNGSKVQIYSCWGGDNQKWRLNSDGSVVGVQSGLCLDAVGNGTANGTLIQLYTC
             410        420        430        440        450        460

490
AM50    WGGNNQKWSYNA
        :|:|||:|:
M64551  SNGSNQRWTRT
             470                                          FIGURE 15B
```

DNA SEQUENCES OF THE FUSIONS BETWEEN *MAN1* CORE/HINGE AND
AM35 GENE pALK945

MAN...T GGT CGC GAC ACC ACC...AM35       (SEQ ID NO: 11:)
      G   R   D   T   T                  (SEQ ID NO: 12:)
*man1* sequence      AM35 sequence pALK948

MAN...T GGT CGC GAC AAG CGC GAC ACC ACC...AM35   (SEQ ID NO: 13:)
      G   R   D   K   R   D   T   T      (SEQ ID NO: 14:)
          KEX2-linker
*man1* sequence          AM35 sequence pALK1021

MAN...T GGC CAG TGT GGA GGT GAC ACC ACC ATC ACC CAG AAC...AM35
      G   Q   C   G   G   D   T   T   I   T   Q   N
   *man1* sequence      AM35 sequence
                                   (SEQ ID NO: 15:)
                                   (SEQ ID NO: 16:)

pALK1022

MAN...T GGC CAG TGT GGA GGT CGC GAC AAG CGC GAC ACC ACC...AM35
      G   Q   C   G   G   R   D   K   R   D   T   T
                      KEX-linker
   *man1* sequence                 AM35 sequence
                                   (SEQ ID NO: 17:)
                                   (SEQ ID NO: 18:)

FIGURE 19

LANE

LANE

PRODUCTION AND SECRETION OF PROTEINS OF BACTERIAL ORIGIN IN FILAMENTOUS FUNGI

This application is a continuation of U.S. application Ser. No. 09/120,804, filed Jul. 23, 1998 (abandoned), which is a continuation of PCT Appl. No. PCT/FI97/00037, filed Jan. 24, 1997 (published in English) which is a continuation-in-part of U.S. Appl. No. 08/590,563 filed Jan. 26, 1996 (issued as U.S. Pat. No. 6,300,114) which is a continuation-in-part of U.S. application Ser. No. 08/468,812 filed Jun. 6, 1995 (issued as U.S. Pat. No. 5,935,836) which is a continuation-in-part of U.S. application Ser. No. 08/332,412 filed Oct. 31, 1994 (abandoned) which is a continuation-in-part of U.S. application Ser. No. 08/282,001 filed Jul. 29, 1994 (abandoned). PCT Application No. PCT/FI97/00037, filed Jan. 24, 1997 and U.S. application Ser. No. 08/590,563, filed Jan. 26, 1996 (issued as U.S. Pat. No. 6,300,114) are both incorporated herein by reference.

FIELD OF THE INVENTION

The present invention provides a method for producing proteins or enzymes of bacterial origin in filamentous fungi, such as *Aspergillus* and *Trichoderma*, by transforming said filamentous fungus hosts with an expression vector containing a DNA sequence encoding a secretable fungal protein or one or more functional domains of said protein. Also provided are expression vectors and hosts useful in said method. The transformed hosts produce preparations, especially enzyme preparations useful e.g. for modifying plant biomass properties, especially to reduce the lignin content in enzyme aided bleaching.

BACKGROUND OF THE INVENTION

Thus, the present invention is directed to the production of proteins or enzymes of bacterial origin in filamentous fungi, for example in *Aspergillus* and *Trichoderma*, by using a fusion to a secretable fungal protein or one or more functional domains of said protein to obtain improved secretion of said bacterial protein or enzyme. Preferably, the proteins originate from actinomycetes. The compositions of the invention are useful for e.g. modifying plant biomass properties, especially to reduce the lignin content in enzyme aided bleaching. The invention is also directed to the area of thermostable xylanases that are active at high temperatures and to a method for bleaching with the aid of the enzyme compositions of the invention.

The aim of kraft pulp bleaching is to remove the residual lignin that is left in pulp after kraft cooking. Traditionally, this has been done by using chlorine-containing chemicals. Because of environmental concerns and consumer demands, alternative bleaching technologies have been desired.

The first biotechnical approach to this problem was to attack the lignin directly with lignin degrading enzymes. However, the chemistry of enzymatic lignin degradation seems to be very complicated and difficult to control.

Lignin can be degraded, if the whole microorganism that produces ligninolytic enzymes is used. However, treatment times are relatively long. For example, treatment times may take days, and the microorganisms need supplemental nutrients to work. It can also be difficult to control the growth of other, undesired, microbes. The use of lignin degradation by isolated ligninolytic enzymes or by microorganisms is the subject of much research. (see, for example, Farrell, R. L. et al., *Lignocellulosics* 305-315 (1992); Jurasek, L., *Lignocellulosics* 317-325 (1992)).

In addition to cellulose and lignin, wood pulp contains hemicellulose. Another approach to reduce the lignin content of pulp is to attack hemicellulose—the third main component of wood. The hemicellulose in native hardwood is mainly xylan, while in softwood the hemicellulose is mainly glucomannans and some xylan. During kraft cooking, part of the xylan is dissolved into the cooking liquor. Towards the end of the cooking period when the alkali concentration decreases, part of the dissolved and modified xylan reprecipitates back onto the cellulose fibre.

In 1986, it was noticed that xylanase pretreatment of unbleached kraft pulp results in a lessened need for chemicals in the bleaching process (Viikari, L. et al., Proceedings of the 3rd Int. Conf. on Biotechnology in the Pulp Paper Ind., Stockholm (1986), pp. 67-69). Xylanase pretreatment of kraft pulp partially hydrolyses the xylan in kraft pulp. The mechanism of how hydrolysis of xylan results in better lignin removal is not fully understood. One frequently suggested possibility is that the pulp structure becomes more porous and this enables more efficient removal of lignin fragments in the subsequent bleaching and extraction stages. Also hydrolysis of the xylan located in the inner parts of the fibre and possibly linked to lignin may have a role. Later, in several laboratories, the xylanase pretreatment was reported to be useful in conjunction with bleaching sequences consisting of $Cl_2$, $ClO_2$, $H_2O_2$, $O_2$ and $O_3$. See reviews in Viikari, L. et al., *FEMS Microbiol. Rev.* 13: 335-350 (1994); Viikari, L. et al., in: Saddler, J. N., ed., *Bioconversion of Forest and Agricultural Plant Residues*, C-A-B International (1993), pp. 131-182; Grant, R., Pulp and Paper Int. (Sept. 1993), pp. 56-57; Senior & Hamilton, *J. Pulp & Paper:*111-114 (Sept. 1992); Bajpai & Bajpai, *Process Biochem.* 27:319-325 (1992); Onysko, A., *Biotech. Adv.* 11: 179-198 (1993); and Viikari, L. et al., *J. Paper and Timber* 73:384-389 (1991).

As a direct result of the better bleachability of the pulp after such a xylanase treatment, there is a reduction of the subsequent consumption of bleaching chemicals, which when chlorine containing chemicals are used, leads to a reduced formation of environmentally undesired organo-chlorine compounds. Also as a direct result of the better bleachability of pulp after a xylanase treatment, it is possible to produce a product with a higher final brightness where such brightness would otherwise be hard to achieve (such as totally chlorine free (TCF) bleaching using peroxide). Because of the substrate specificity of the xylanase enzyme, cellulose fibers are not harmed and the strength properties of the product are well within acceptable limits.

A xylanase that is active at an alkaline pH would decrease the need to acidify the pulp prior to xylanase treatment. In addition, the temperatures of many modern kraft cooking and bleaching processes are relatively high, well above the 50° C. that is suitable for many of the commercial bleaching enzymes. Accordingly, a need exists for thermostable xylanase preparations that are stable at alkaline pH values for use in wood pulp bleaching processes.

It is known that actinomycetes, e.g. (*Microtetraspora flexuosa* ATCC35864 and *Thermomonospora fusca* KW3, produce thermostable and alkaline stable xylanases (U.S. Pat. No. 5,437,992 and EP 473 545. The cloning of xylanases has been reported from several bacteria (e.g. Ghangas, G.S. et al., *J. Bacteriol.* 171:2963-2969 (1989); Lin, L. -L., Thomson, J. A., *Mol. Gen. Genet.* 228:55-61 (1991); Shareck, F. et al., *Gene* 107:75-82 (1991); Scheirlinck, T. et al., *Appl Microbiol Biotechnol.* 33:534-541 (1990); Whitehead, T. R., Lee, D. A., *Curr. Microbiol.* 23:15-19 (1991)); and also from *Actinomadura* sp. FC7 (Ethier, J. -F. et al., in: *Industrial Microorganisms: Basic and Applied Molecular Genetics*, R. Baltz et al., Eds, (Proc. 5th ASM Conf. Gen. Mol. Biol. Indust. Microorg., Oct. 11-15, 1992, Bloomington, Ind., poster C25)). It has been proposed by some researchers that the former genus *Actinomadura* should be divided into two genera, *Actinomadura* and *Microtetraspora*, the latter including, e.g. the former *A. flexuosa* (Kroppenstedt et al., *System. Appl. Microbiol.* 13: 148-160 (1990).

The use of hemicellulose hydrolyzing enzymes in different bleaching sequences is discussed in WO 89/08738, EP 383 999, WO 91/02791, EP 395 792, EP 386 888, EP 473 545, EP 489 104 and WO 91/05908, WO 95/34662, WO 95/18219, WO 95/27779, WO 95/34662, WO 95/18219, WO 92/04664 and WO 92/03540. The use of hemicellulolytic enzymes for improved water removal from mechanical pulp is discussed in EP 262 040, EP 334 739 and EP 351 655, DE 4,000,558, WO 92/04664, WO 92/03540, WO 94/21785 and EP 513 140. When the hydrolysis of biomass to liquid fuels or chemicals is considered, the conversion of both cellulose and hemicellulose is essential to obtain a high yield (Viikari et al., "Hemicellulases for Industrial Applications," In: *Bioconversion of Forest and Agricultural Wastes*, Saddler, J., ed., CAB International, USA (1993)). Also, in the feed industry, there is a need to use a suitable combination of enzyme activities to degrade the high β-glucan and hemicellulose containing substrate.

The efficient and cost-effective production of thermostable xylanases is a problem, because thermostable xylanases originate mainly from relatively unstudied bacteria, which often produce only minimal or very small amounts of xylanase. Further, there is little or no experience of cultivating these microbes in a fermentor or no fermentation processes available. Furthermore, these microbes may be unsuitable for industrial scale production. On the other hand, filamentous fungi like *Aspergillus* and *Trichoderma* are known to produce large quantities of proteins, on an industrial scale. In particular, these fungi have been shown to be suitable for production of homologous or heterologous proteins of fungal origin.

There are very few reports related to the production of proteins or enzymes of bacterial origin in filamentous fungi: the production of endoglucanase from *Cellulomonas fimi* (Gwynne et al., *Bio/Technology* 5: 713-719 (1987); and β-glucuronidase from *E. coli* (Punt et al., *J. Biotechnol.* 17: 19-34 (1991) have been reported in *A. nidulans*. Of these enzymes, endoglucanase was secreted into the culture medium by *Aspergillus nidulans* in the range of 10-15 mg protein per liter. β-glucuronidase was only detectable intracellularly.

Many of the studies on heterologous gene expression have concerned mammalian genes (van den Hondel et al., Heterologous gene expression in filamentous fungi, Ed. Bennett and Lasure. *More Gene Manipulations in Fungi* Academic Press, San Diego, U.S.A., pp. 396-428 (1991). So far, the initial yields of eucaryotic enzymes in filamentous fungi have been in a range of tens of mg per liter in shake flask cultivations. In the International patent publication WO 90/15860 secretion of chymosin by *A. niger* var. awamori was described using a fusion to the homologous glucoamylase gene. Nyyssönen et al., *Bio/Technology* 11: 591-595 (1993) describes the production of antibody fragments in *Trichoderma reesei*. The best yield of antibody fragments when produced as a fusion to the cellobiohydrolase 1 gene of *T. reesei* was in the range of 40 mg per liter in a shake flask cultivation.

So far the inventors of the present application are not aware of any reports of the production of proteins of bacterial origin in *Trichoderma*.

SUMMARY OF THE INVENTION

The invention is directed inter alia, to a method of producing, i.e. improved expressing and secreting proteins or enzymes originating from bacteria, especially from actinomycete. The invention, however, is not strictly limited to higher secretion levels. Lesser or greater levels of expression are acceptable. The main purpose of the invention is to provide an alternative method for producing enzymes originating from actinomycete in filamentous fungi.

The characteristics of the present invention are as set forth in the claims.

The present invention is related to a recombinant expression vector for production of bacterial proteins or enzymes, especially xylanases and cellulases in a filamentous fungal host, especially in *Aspergillus* and *Trichoderma*, most preferably in *T. reesei*. Said vector comprises a promoter operably linked to a DNA sequence of a filamentous fungus secretable protein or one or more functional domains of said protein, which in turn frames the DNA sequence, e.g. SEQ ID NO: 1: or SEQ ID NO: 3:, or equivalents thereof, which encode a bacterial protein, preferably an actinomycetous protein, most preferably *Actinomadura flexuosa* 35 kD (AM35) or 50 kD (AM50) xylanase, i.e. SEQ ID NO: 2: and SEQ ID NO: 3: and equivalents thereof, as well as *Thermomonospora fusca* cellulases, especially the *T. fusca* endocellulase E5.

Also provided are peptide sequences of *A. flexuosa* 35 kDa and 50 kDa protein used for identifying and characterizing the protein sequences. Said peptides are assigned SEQ ID NO: 6:, SEQ ID NO: 7:, SEQ ID NO: 8:, SEQ ID NO: 9: and SEQ ID NO: 10:.

The preferred promoters of the present invention are promoters of a filamentous fungus secretable protein, most preferably a *T. reesei* cbh1 promoter or a *A. niger* glucoamylase promoter.

Examples of recombinant expression vectors are the plasmids pALK945, pALK948, pALK1021 and pALK1022, which are constructed as shown in FIG. 17 and contain SEQ ID NO: 11:, SEQ ID NO: 13:, SEQ ID NO: 15: and SEQ ID NO: 17:, respectively and which encode the proteins comprising SEQ ID NO: 12:, SEQ ID NO: 14:, SEQ ID NO: 16:, and SEQ ID NO: 18: or equivalents thereof.

All the proteins comprising SEQ ID NO: 12:, SEQ ID NO: 14:, SEQ ID NO: 16:, and SEQ ID NO: 18: or equivalents thereof have a N-terminal DNA sequence SEQ ID NO: 5:, which is identical with the N-terminal sequence of the wild type *A. flexuosa* xylanase (D-T-T-I-T-Q).

The present invention further provides preparations containing one or more proteins or enzymes, preferably xylanases or cellulases originating from bacteria, especially from actinomycetes in an essentially cell-free culture medium, which can be subjected to suitable down-stream processing methods.

The preparations containing enzymes, especially xylanases or cellulases originating from actinomycetes are obtainable by cultivating hosts transformed with the expression vectors of the present invention. These preparations are useful e.g. for enzyme-aided bleaching, because the enzymes are stable at processing temperatures, when the processing temperatures are in the ranges 50-90° C., preferably 60-85° C., most preferably 70-80° C.

Especially, said preparations are useful for treating paper making pulp and for enzymatical treating of plant biomass.

It is therefore the main object of this invention to produce more efficiently protein or enzymes of bacterial origin in filamentous fungi such as *Aspergillus* or *Trichoderma*. Preferably, the host is *Trichoderma* and the proteins originate from actinomycetes.

FIGURES

FIG. 1 shows the effect of pH on *Actinomadura flexuosa* DSM43186 xylanase activity (culture supernatant) at 50° C.

FIGS. 2A, 2B and 2C show the effect of temperature on *A. flexuosa* DSM43186 xylanase activity (culture supernatant) at pH values 6.9, 7.8 and 9.0 and at time points of 0, 30, 60 and 120 minutes. The highest xylanase activity of the whole experiment is described as 100% and all other activity values are proportional to it.

FIG. 2A shows the activities in a temperature of 60° C.
FIG. 2B shows the activities in a temperature of 70° C.
FIG. 2C shows the activities in a temperature of 80° C.

Figure 3:
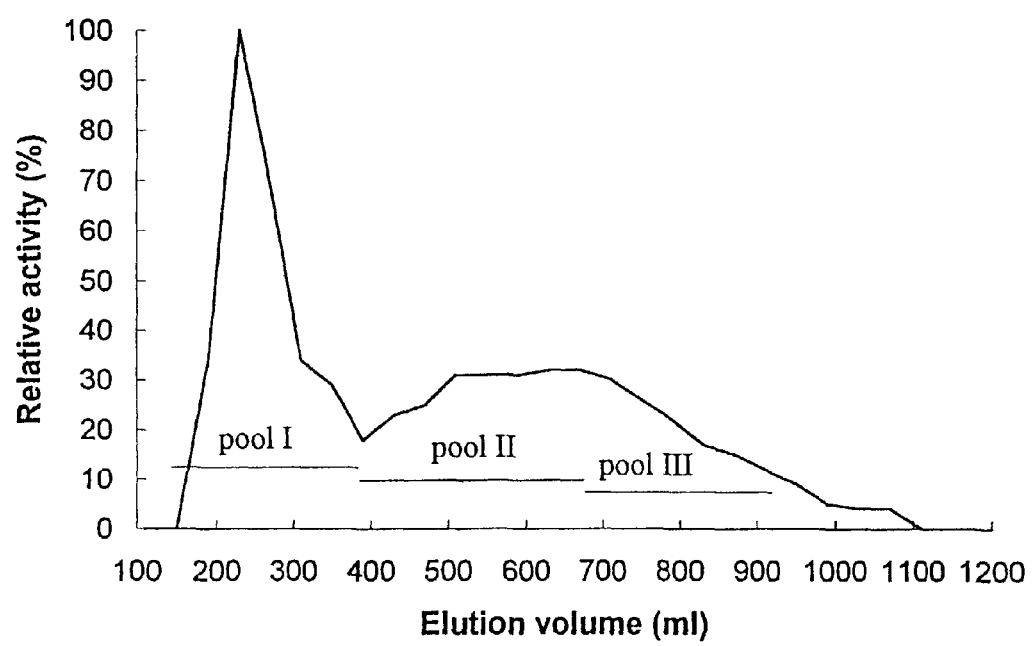
FIG. 3 shows the DEAE Sepharose CL-6B chromatography elution profile of *A. flexuosa* DSM43186 xylanases.
Figure 4A:
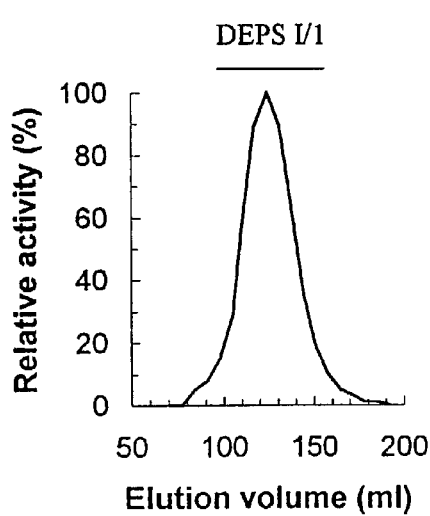
FIG. 4A shows the Phenyl Sepharose CL-4B chromatography elution profile of DEAE pool I of FIG. 3. The fractions that were combined to provide sample DEPS I/1 are indicated.
Figure 4B:
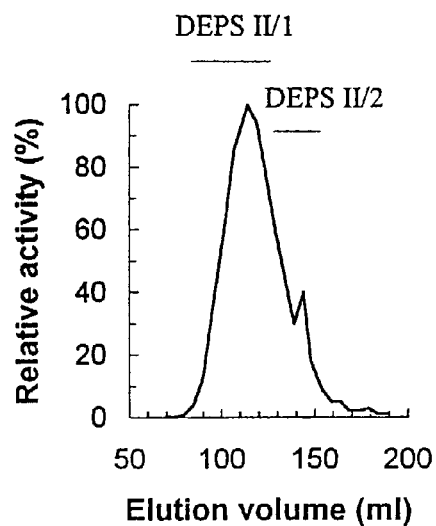
FIG. 4B shows the Phenyl Sepharose CL4B chromatography elution profile of DEAE pool II of FIG. 3. The fractions that were combined to provide sample DEPS II/1 and DEPS II/2 are indicated.
Figure 4C:
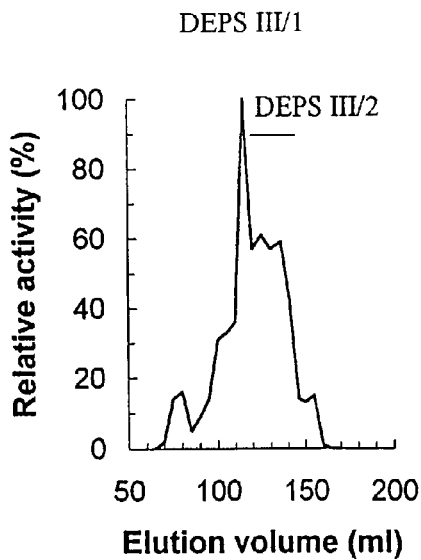
FIG. 4C shows the Phenyl Sepharose CL-4B chromatography elution profile of DEAE pool III of FIG. 3. The fractions that were combined to provide sample DEPS III/1 and DEPS III/2 are indicated.
Figure 5A:
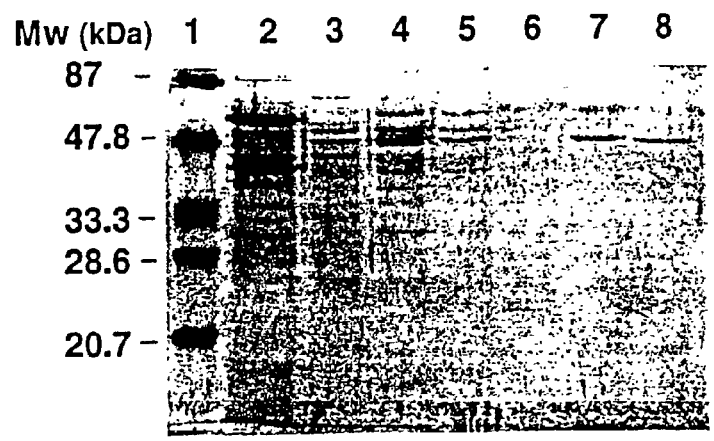

FIG. 5A shows the Coomassie Brilliant Blue protein staining pattern of the various chromatographic pools. Lane 1: molecular weight markers; lane 2: medium; lane 3: DEPS (Pool I/1); lanes 4 and 5: DEPS (Pool II/1 and II/2, respectively); lane 6: empty; lanes 7 and 8: DEPS (Pool III/1 and III/2, respectively). DEPS: Fractions after the DEAE chromatography shown in FIG. 3 and the Phenyl Sepharose chromatography shown in FIGS. 4A-4C.

Figure 5B:
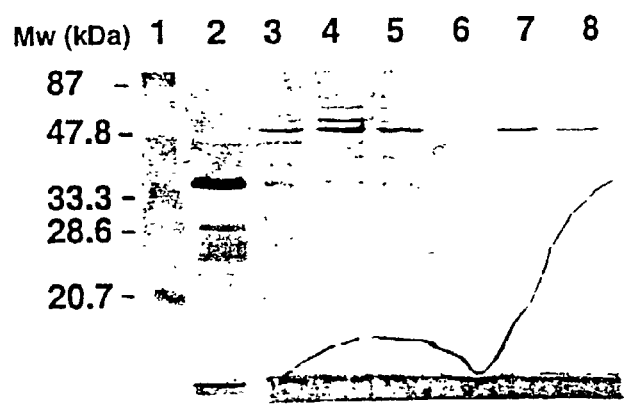

FIG. 5B shows the Western blot analysis of the various chromatographic pools stained in FIG. 5A. Polyclonal antiserum raised against the *Thermomonospora fusca* XynA xylanase was used for detection. Lane 1: molecular weight markers; lane 2: medium; lane 3: DEPS (Pool I/1); lanes 4 and 5: DEPS (Pool II/1 and II/2, respectively); lane 6: empty; lanes 7 and 8: DEPS (Pool II/1 and III/2, respectively). DEPS: Fractions after the DEAE chromatography shown in FIG. 3 and the Phenyl Sepharose chromatography shown in FIGS. 4A-4C.

Figure 6A:
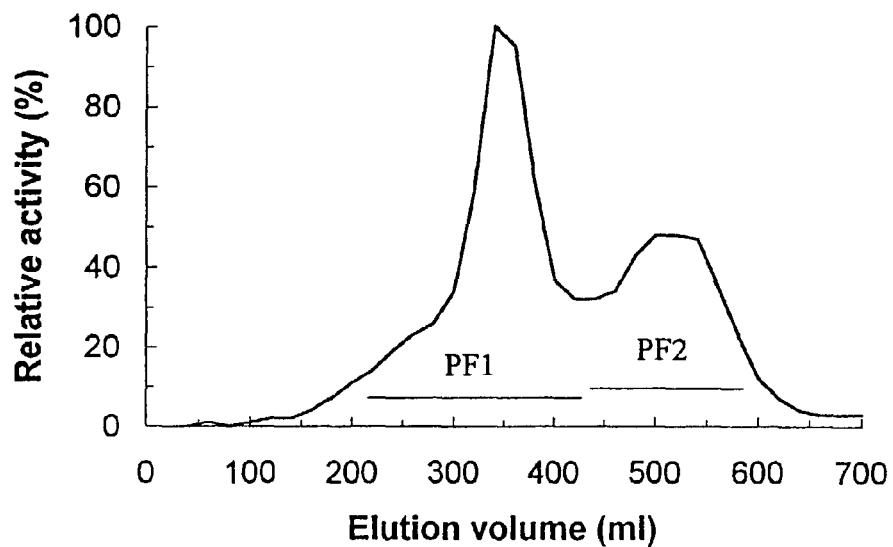

FIG. 6A shows the Phenyl Sepharose FF chromatography elution profile of DEAE flow through permeate. The tubes that were combined to provide sample PF1 and PF2 are indicated.

Figure 6B:
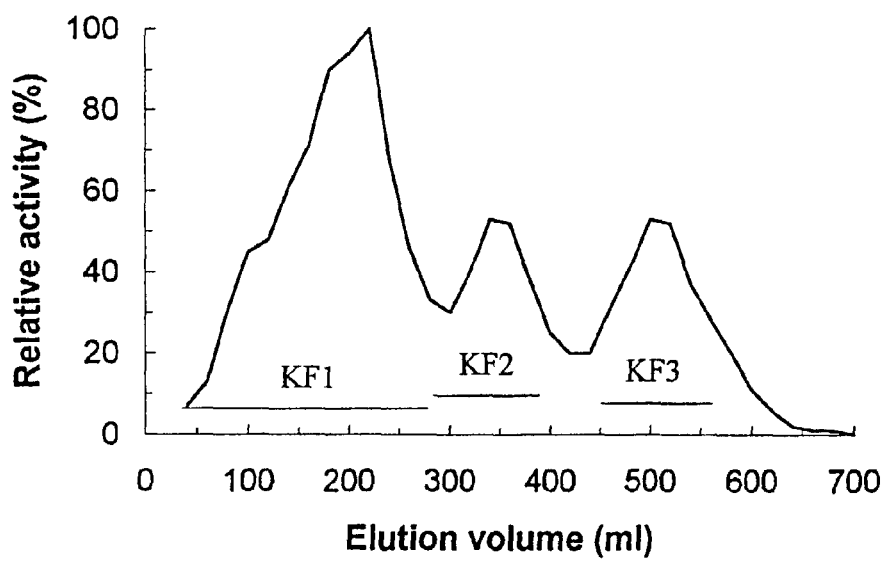

FIG. 6B shows the Phenyl Sepharose FF chromatography elution profile of DEAE flow-through concentrate. The tubes that were combined to provide sample KF1, KF2 and KF3 are indicated.

Figure 7A:
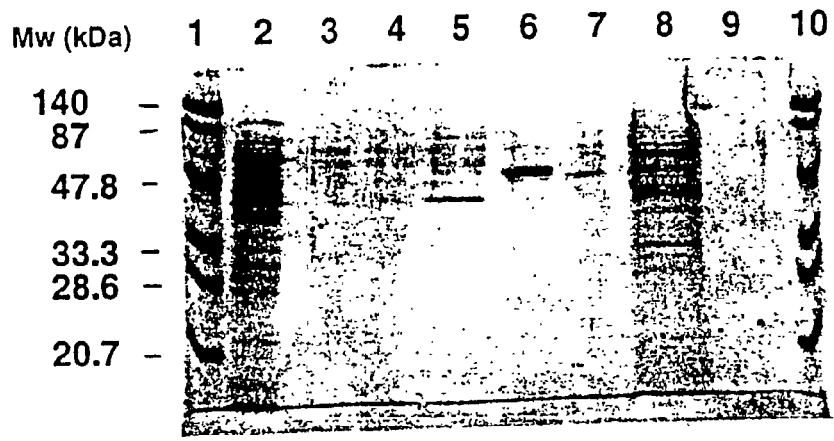

FIG. 7A shows the Coomassie Blue protein staining pattern of the various chromatographic pools. Abbreviations are as in FIGS. 6A and 6B. Lanes 1 and 10: molecular weight markers; lane 2: medium; lane 3: PF1; lane 4: PF2; lane 5: KF1; lane 6: KF2; lane 7: KF3; Lane 8: DEAE flow-through concentrate; Lane 9: Empty.

Figure 7B:

FIG. 7B shows the Western blot analysis of the various chromatographic pools stained for protein in FIG. 7A. Polyclonal antiserum raised against the *T. fusca* XynA xylanase was used for detection. Abbreviations are as in FIGS. 6A and 6B. Lanes 1 and 10: molecular weight markers; lane 2: medium; lane 3: PF1; lane 4: PF2; lane 5: KF1; lane 6: KF2; lane 7: KF3. Lane 8: DEAE flow-through concentrate; Lane 9: empty.

Figure 8:
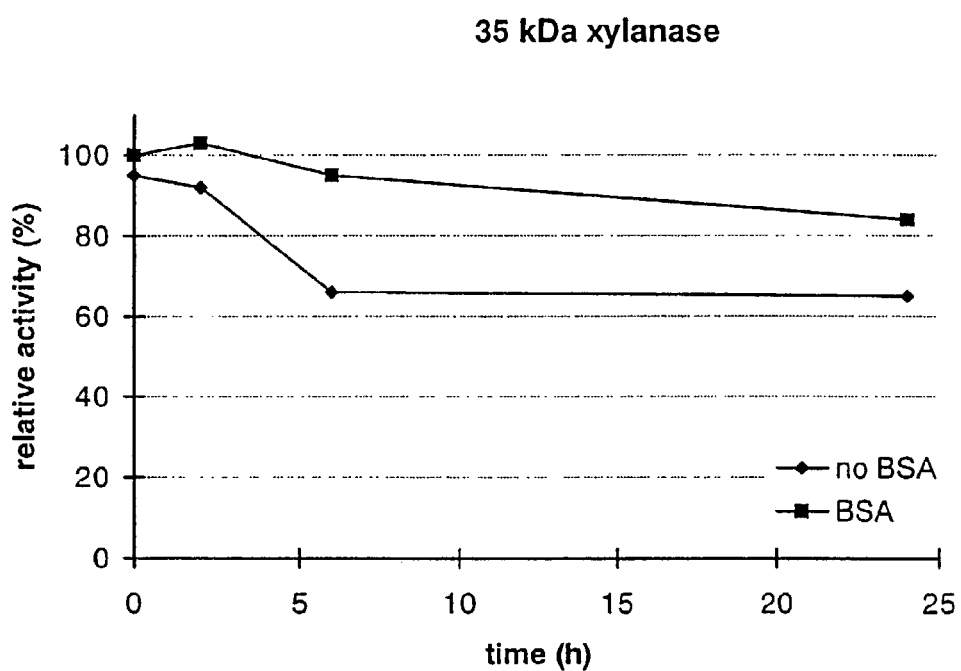

FIG. 8 shows the thermostability of purified *A. flexuosa* 35 kDa xylanase (AM35) at 70° C., pH 6 with and without added bovine serum albumin (BSA). The enzyme sample was incubated in McIlvain's buffer +/−BSA (100 µg/ml). Samples were collected after 0, 2, 6, and 24 hours of incubation and enzyme activity assay was done at pH 6.5, 60° C.

Figure 9:
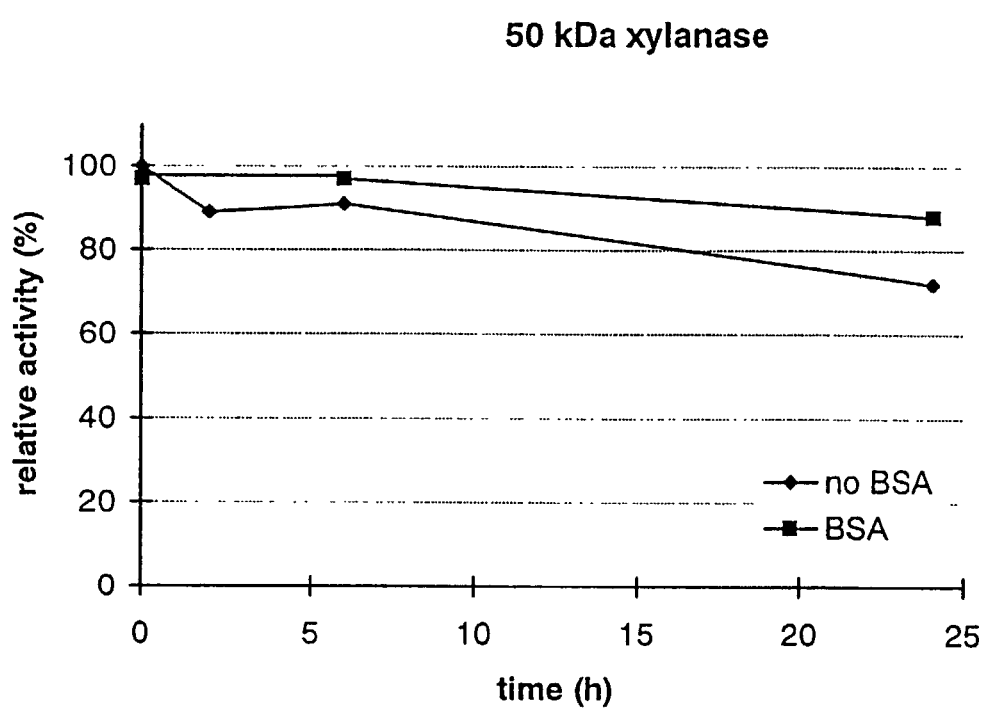

FIG. 9 shows the thermostability of purified *A. flexuosa* 50 kDa xylanase (AM50) at 70° C., pH 6 with and without added BSA. The enzyme sample was incubated in McIlvain's buffer +/−BSA (100 µg/ml). Samples were collected after 0, 2, 6 and 24 hours of incubation and enzyme activity assay was done at pH 6.5, 60° C.

Figure 10A:
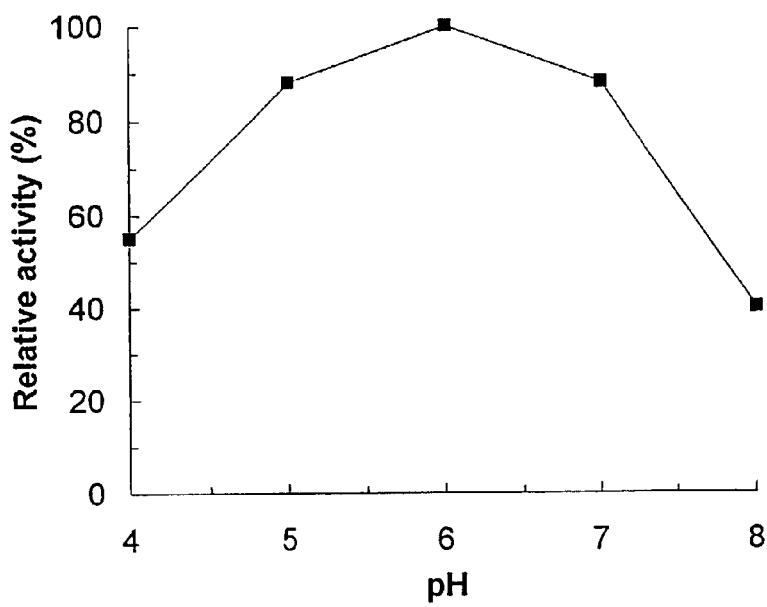

FIG. 10A shows the effect of pH on the activity of the 35 kDa xylanase at 80° C.

Figure 10B:
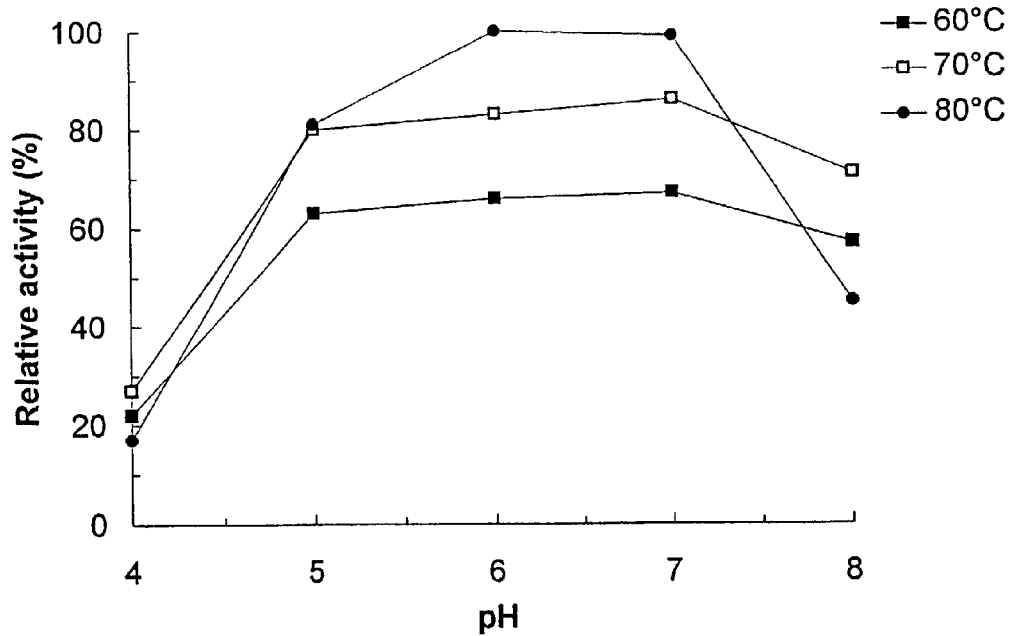

FIG. 10B shows the effect of pH on the activity of the 50 kDa xylanase at 60° C., (closed squares), 70° C. (open squares) and 80° C. (closed circles).

Figure 10C:
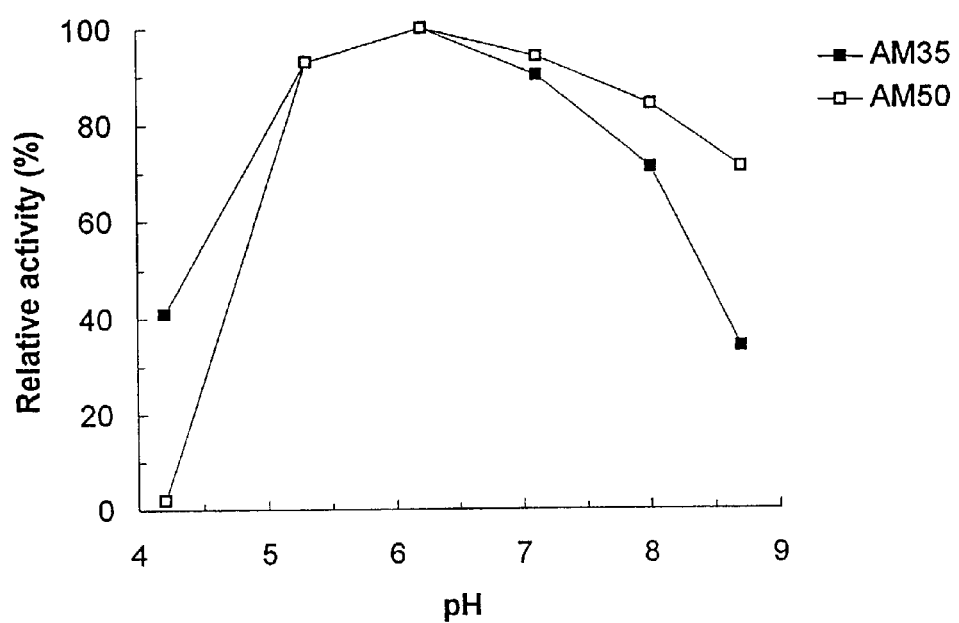

FIG. 10C shows the effect of pH on the activity of the 35 kDa (closed squares) and the 50 kDa (open squares) xylanases at 60° C. with 60 minutes incubations.

Figure 11:
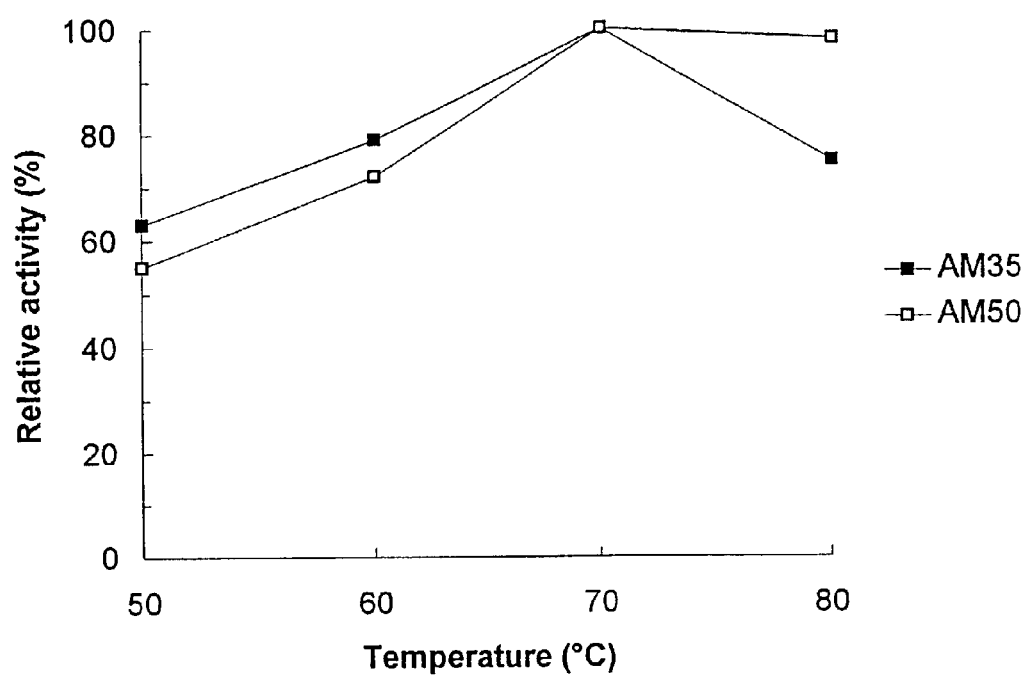

FIG. 11 shows the effect of temperature on the activity of the 35 kDa (closed squares) and the 50 kDa (open squares) at pH 7 with 60 minutes incubations.

Figure 12:
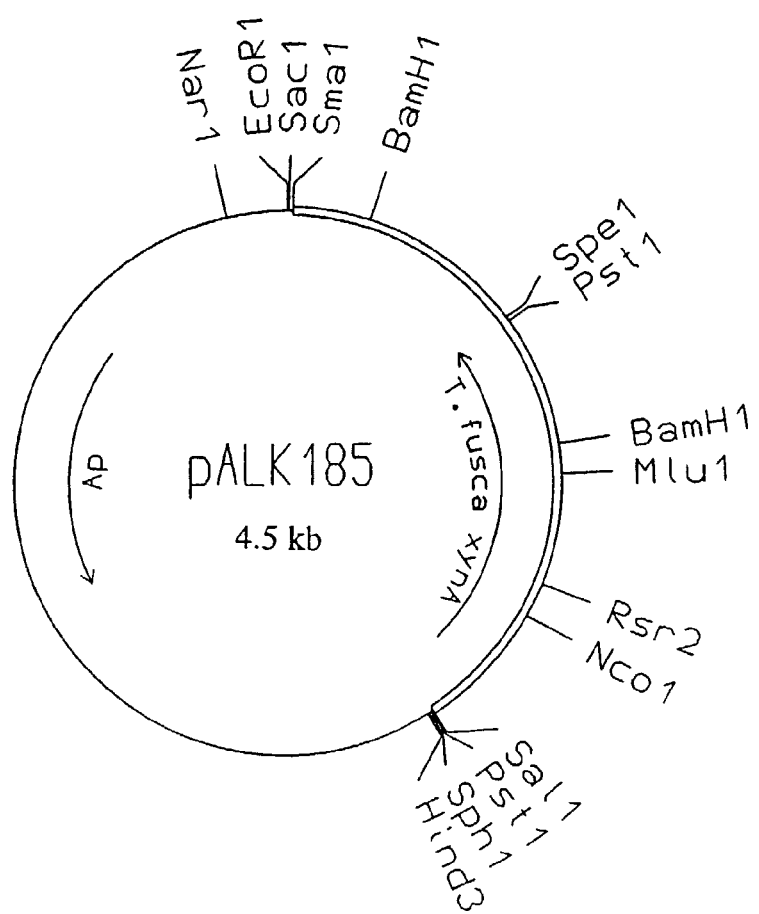

FIG. 12 is a map of plasmid pALK185 (4.5 kb), containing *T. fusca* xylanase gene (xynA).

FIG. 13 shows the DNA sequence and the amino acid sequence of 1375 bps of *A. flexuosa* DSM43186 35 kDa xylanase.

FIG. 14 shows the DNA sequence and amino acid sequence of 1864 bps of *A. flexuosa* DSM43186 50 kDa xylanase.

FIG. 15A shows a homology comparison at the amino acid level between the AM50-peptide derived from the 1864 bps insert and the *Actinomadura* sp. FC7 xylanase II (accession no. U08894) gene. The figure shows that there was 70.7% identity in a 434 amino acid overlap.

FIG. 15B shows a homology comparison at the amino acid level between the AM50-peptide derived from the 1864 bps insert and the *Streptomyces lividans* xylanase A (xlnA) gene (accession no. M64551). The figure shows that there was 70.3% identity in a 489 amino acid overlap.

Figure 16:
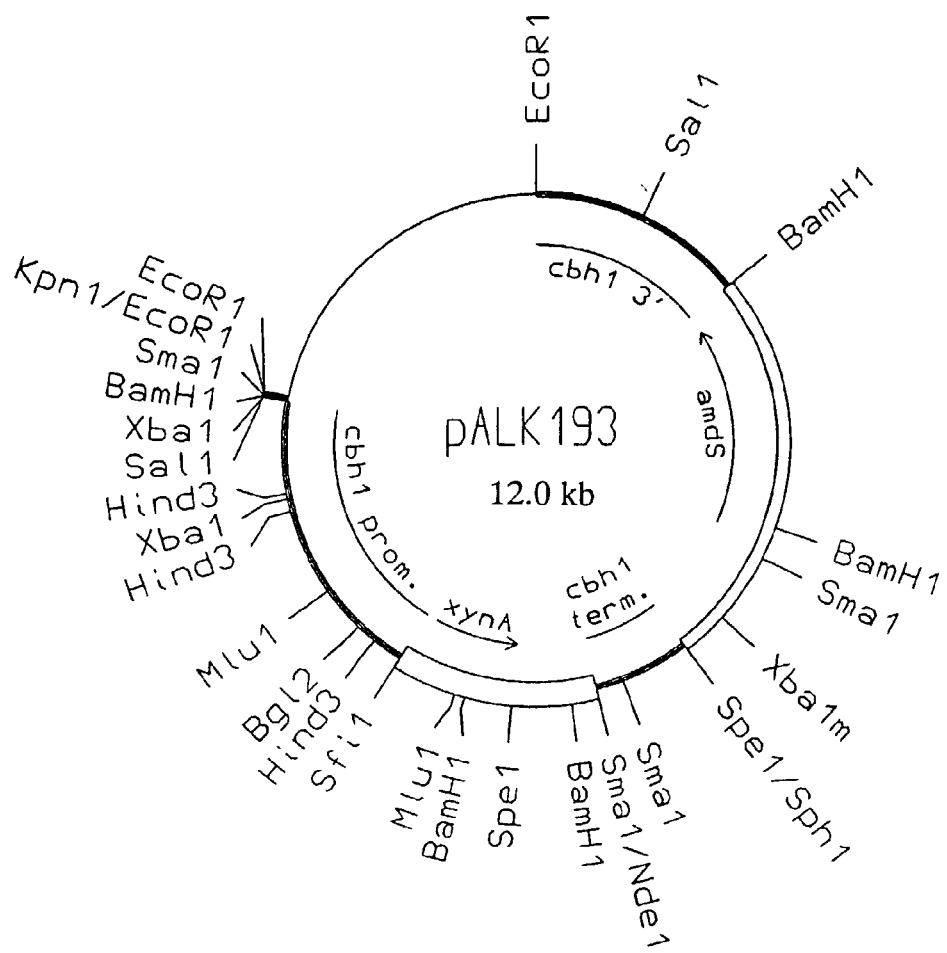

FIG. 16 shows the expression cassette pALK193 (12 kb) containing the expression cassette for production of *T. fusca* xylanase XynA in *T. reesei*.

Figure 17:
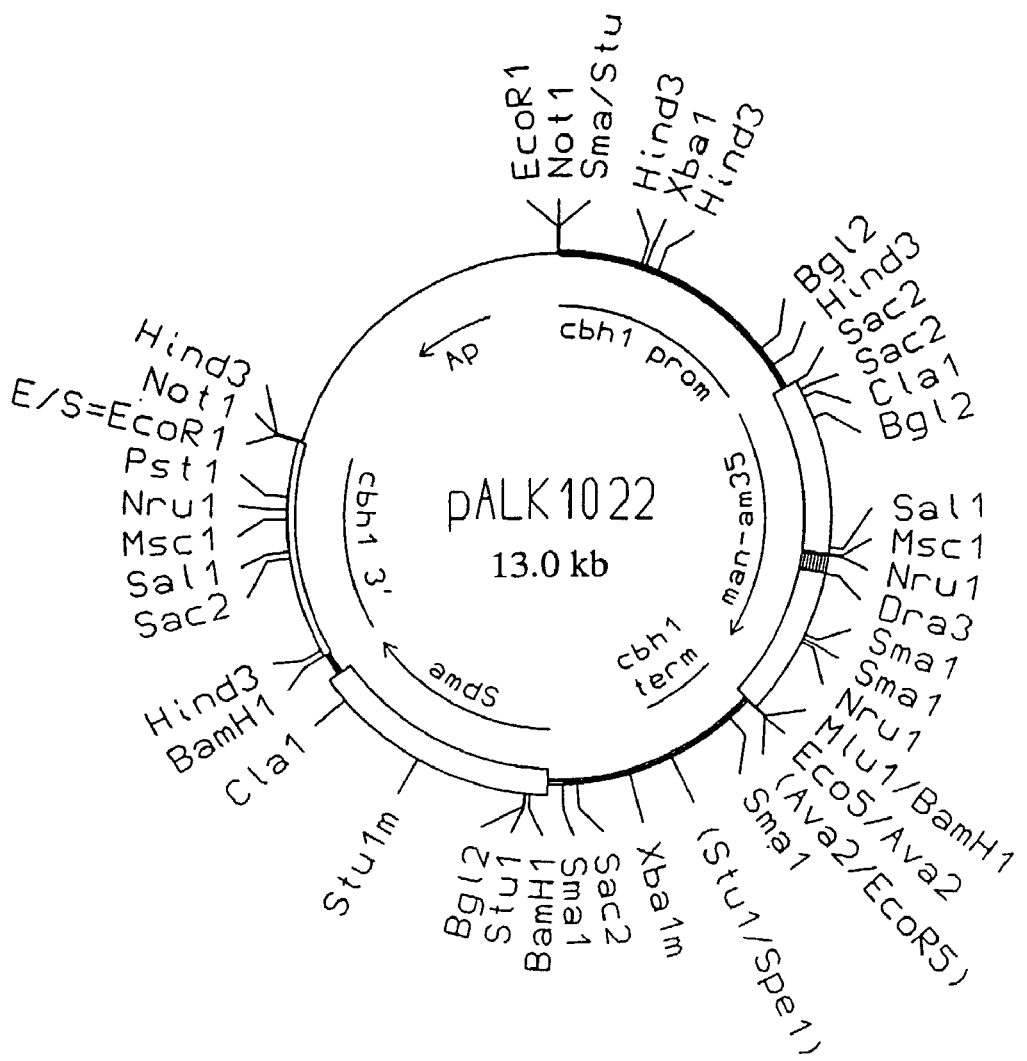

FIG. 17 is a map of plasmid pALK1022 (13 kb) containing the expression cassette for production of *A. flexuosa* 35 kDa xylanase in *T. reesei*.

Figure 18:
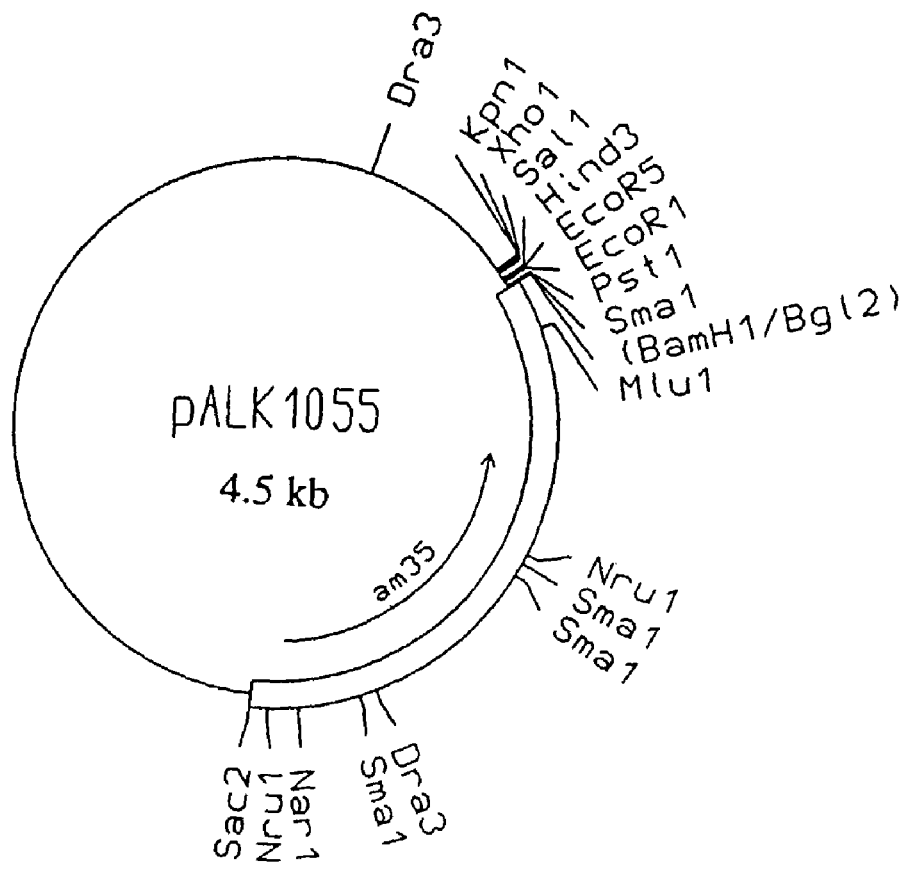

FIG. 18 is a map of plasmid pALK1055 (4.5 kb) containing the gene for *A. flexuosa* 35 kDa xylanase.

FIG. 19 shows the DNA sequence SEQ ID NO: 11:, SEQ ID NO: 13:, SEQ ID NO: 15: and SEQ ID NO: 17 as well as the corresponding amino acid sequences SEQ ID NO: 12:, SEQ ID NO: 14:, SEQ ID NO: 16: and SEQ ID NO: 18:, which comprise the fusions between the man1 core/hinge and the am35 gene for pALK945, pALK948, pALK1021 and pALK1022.

Figure 20:
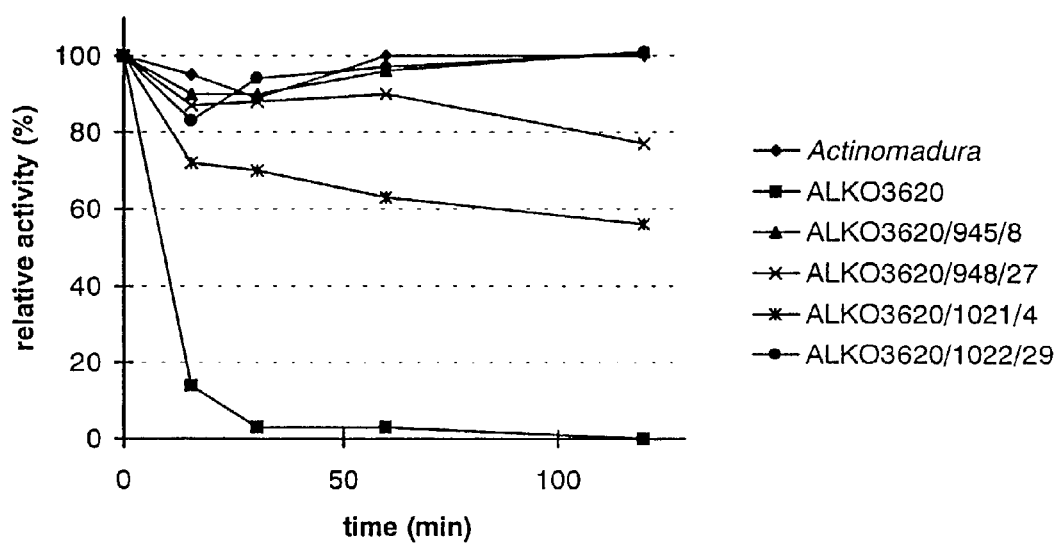

FIG. 20 shows the thermal stability of xylanase activity from culture supernatants of a *A. flexuosa* DSM43186 and chosen *T. reesei* transformants producing *A. flexuosa* 35 kDa xylanase. Samples from the culture supernatants were incubated at 70° C., pH 7 in McIlvain's buffer. (BSA was added to 100 µg/ml) for 0, 15, 30, 60 and 120 minutes after which xylanase activities from the sample were determined at 70° C., pH 7 (5 minutes incubation).

Figure 21:
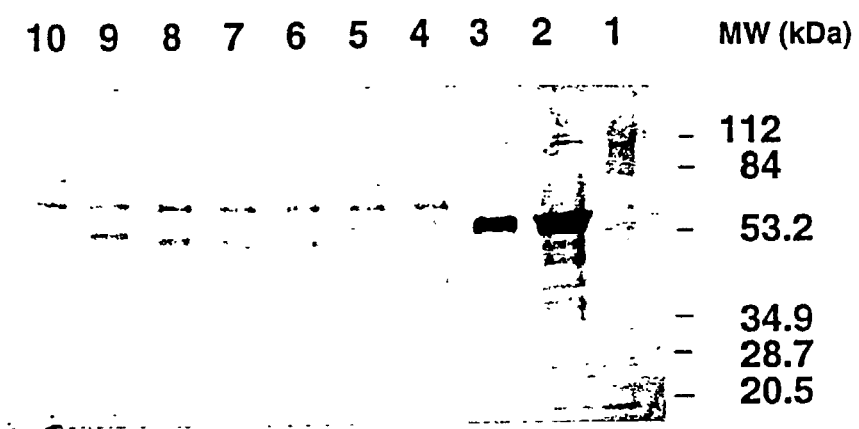

FIG. 21 shows a Western blot analysis of culture supernatants from transformants producing *A. flexuosa* AM35 xylanase. Polyclonal antiserum raised against the purified β-mannanase (pI 5.4) of *T. reesei* RutC30 was used for detection. Lane 1: prestained low molecular weight marker (Bio-Rad, U.S.A.); Lanes 2-3: purified 53 kDa β-mannanase protein sample; Lane 4: culture medium of MANI core producing strain, ALKO 3620/pALK1010/24. Lane 5: culture medium of the transformation host strain ALKO3620; Lanes 6-10: Culture media of the transformants ALKO3620/pALK945/8, ALKO3620/pALK945/6, ALKO3620/pALK948/7, ALK03620/pALK1022/29 and ALKO3620/pALK1021/4, respectively.

Figure 22:
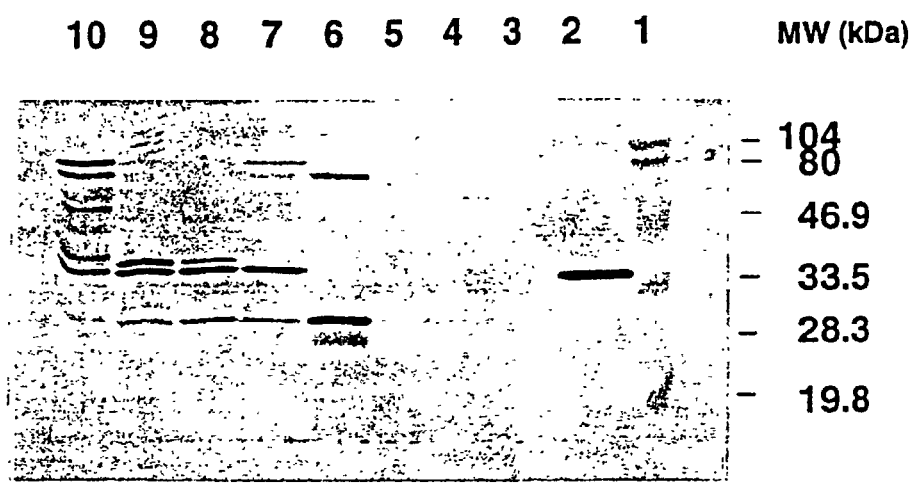

FIG. 22 shows a Western blot analysis of culture supernatants from transformants producing *A. flexuosa* xylanase. Polyclonal antiserum raised against the purified 35 kDa xylanase of *A. flexuosa* was used for detection. Lane 1: prestained low molecular weight marker (Bio-Rad, U.S.A.); Lane 2: purified 35 kDa xylanase of *A. flexuosa* DSM43186; Lane 3:53 kDa β-mannanase protein sample; Lane 4: culture medium of the MANI core producing strain, ALKO3620/pALK1010/24; Lane 5: culture medium of the transformation host ALKO3620; Lanes 6-10: culture media of the transformants ALKO3620/pALK945/8, ALKO3620/pALK945/6, ALKO3620/pALK948/27, ALKO3620/pALK1022/29 and ALKO3620/pALK1021/4, respectively.

Figure 23A:
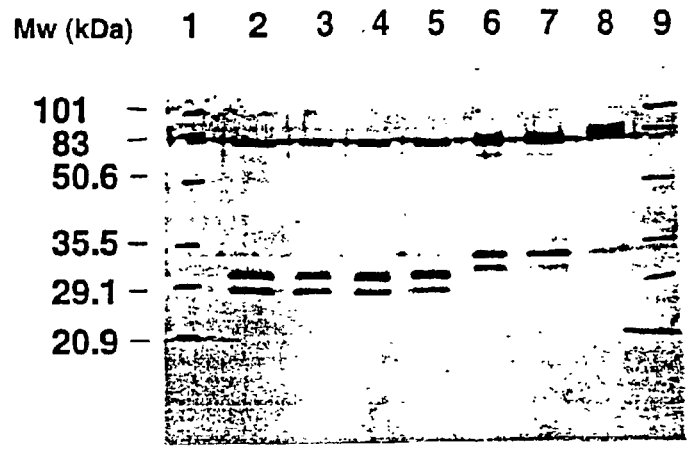

FIG. 23A: Western-blot of growth medium samples from a Fed-batch fermentation of ALK03620/pALK945/8. Polyclonal antibody raised against the purified *A. flexuosa* 35 kDa xylanase. Lane 1 and 9: prestained molecular mass standards (LMW, Bio-Rad); Lane 3 to 8: growth medium samples after 7, 6, 5, 4, 3 and 2 days fermentation times, respectively; Lane 2: final sample after 7.3 days fermentation.

Figure 23B:
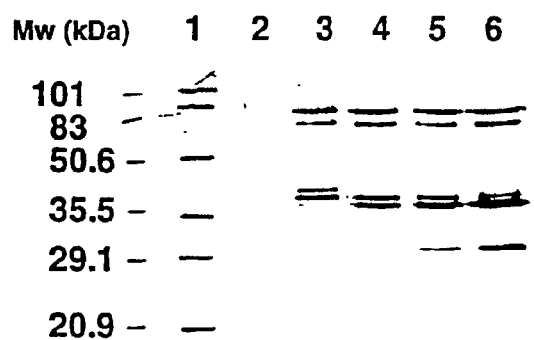

FIG. 23B: Western-blot of growth medium samples from a laboratory fermentation of ALKO3620/pALK945/6. Polyclonal antibody raised against the purified *A. flexuosa* 35 kDa xylanase. Lane 1: prestained molecular mass standards (LMW, Bio-Rad); Lane 2 to 6: growth medium samples after 1, 2, 3, 4 and 5 days fermentation times, respectively.

Figure 24:
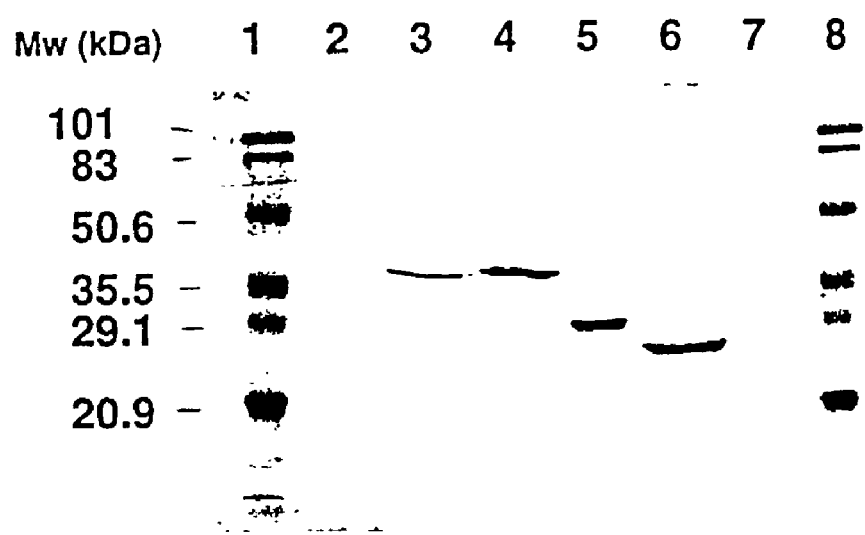
Figure 25A:
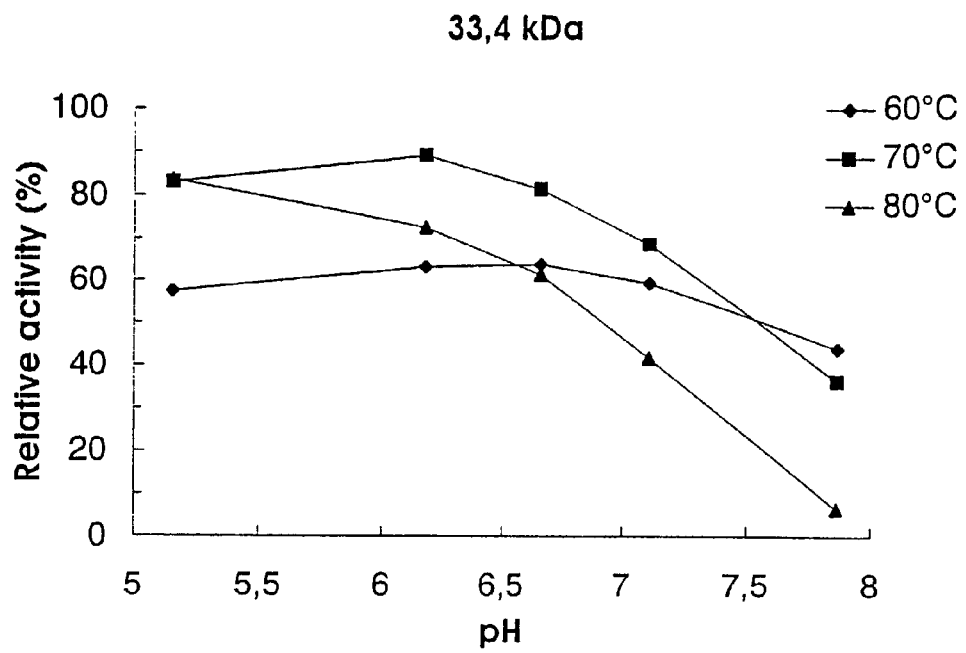
Figure 25B:
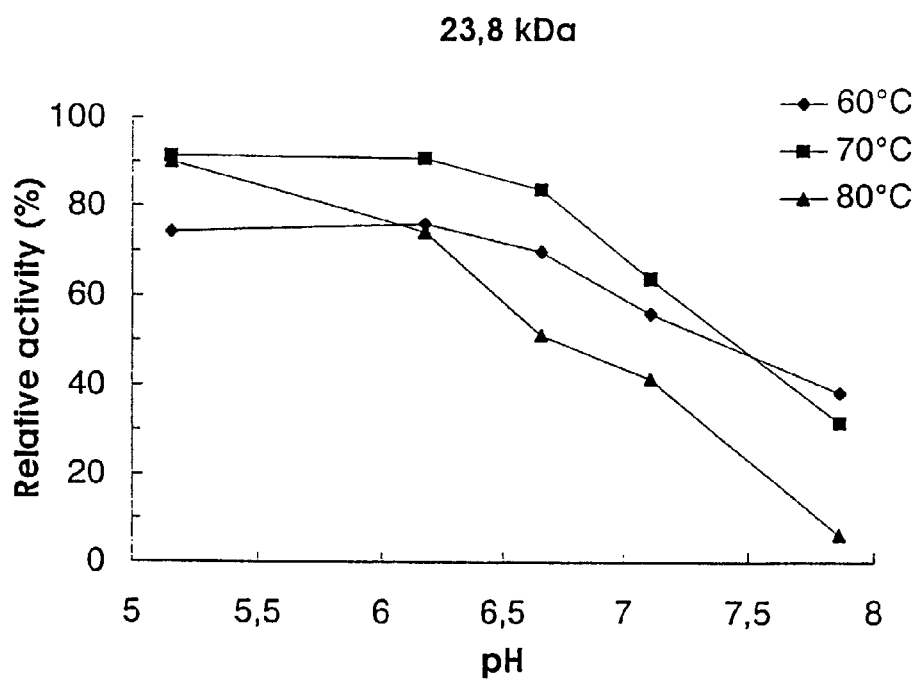
Figure 25C:
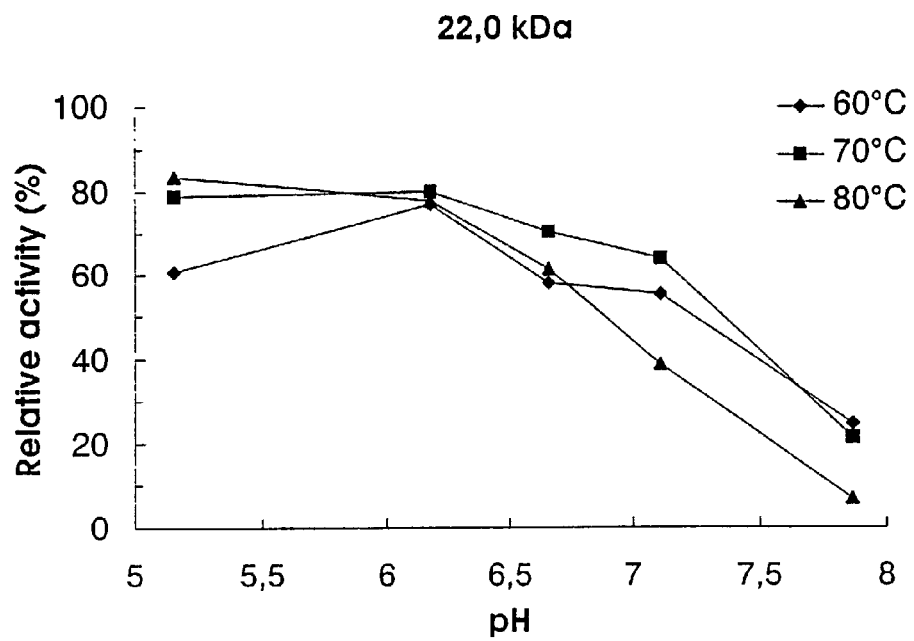
Figure 25D:
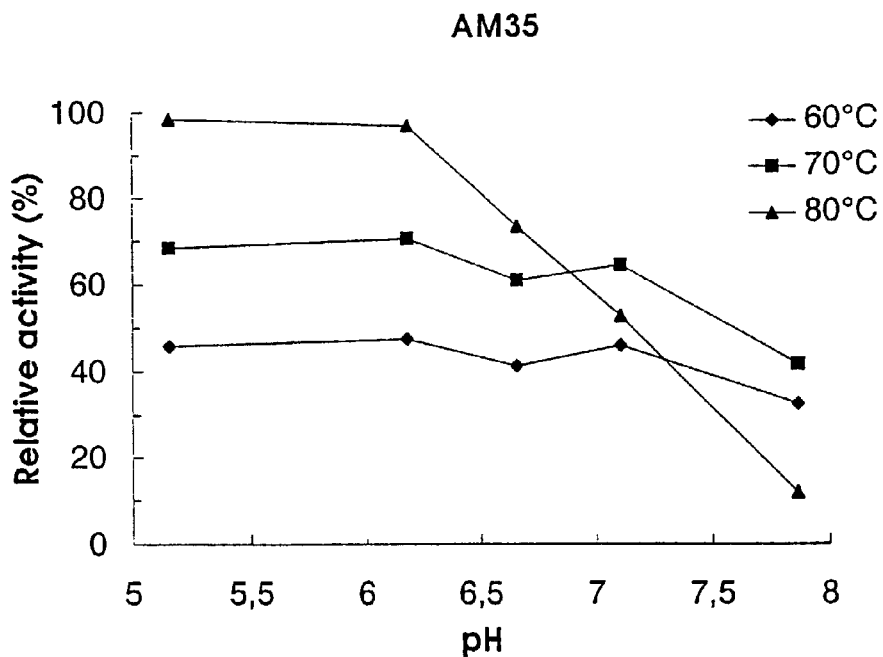

FIG. 24: SDS-PAGE of purified recombinant *A. flexuosa* 35 kDa xylanases and wild-type *A. flexuosa* 35 kDa xylanase. Lanes 1 and 8: Prestained molecular mass standards (Bio-Rad); Lane 3: purified wild-type 35 kDa xylanase; Lane 4: purified 33.4 kDa xylanase; Lane 5: purified 23.8 kDa xylanase; Lane 6: purified 22 kDa xylanase; Lane 2 and 7: empty.

FIG. 25: Temperature and pH dependence of purified recombinant and wild-type *A. flexuosa* 35 kDa xylanases. Incubations were performed at temperatures and pH values indicated for 60 min with 1% (w/v) birch xylan (Roth 7500) as substrate.

DEPOSITS

Plasmid pALK923, pALK938, pALK939, pALK940, pALK941 and pALK1056 were deposited at the Deutsche Sammlung von Mikroorganismen und Zellkulturen GmbH, Mascheroder Weg 1 b, D-38124 Braunschweig, Germany assigned accession numbers DSM9322, DSM9899, DSM9900, DSM9901, DSM9902 and DSM9903, respectively. pALK923 was deposited on Jul. 27, 1994, and pALK938-941 and pALK1056 were deposited on Apr. 3, 1995.

Plasmids pALK927 and pALK928 were deposited at the DSM on Sep. 27, 1994, and assigned accession numbers DSM9447 and DSM9448, respectively.

DETAILED DESCRIPTION OF THE PREFERRED EMBODIMENTS

I. Definitions

In the description that follows, a number of terms used in recombinant DNA technology are extensively utilized. In order to provide a clearer and consistent understanding of the specification and claims, including the scope to be given such terms, the following definitions are provided.

Cloning vehicle. A plasmid or phage DNA or other DNA sequence (such as a linear DNA) which provides an appropriate nucleic acid environment for the transfer of a gene of interest into a host cell. The cloning vehicles of the invention may be designed to replicate autonomously in prokaryotic and eukaryotic hosts. In fungal hosts such as *Trichoderma*, the cloning vehicles generally do not autonomously replicate and instead, merely provide a vehicle for the transport of the gene of interest into the *Trichoderma* host for subsequent insertion into the *Trichoderma* genome. The cloning vehicle may be further characterized by one or a small number of endonuclease recognition sites at which such DNA sequences may be cut in a determinable fashion without loss of an essential biological function of the vehicle, and into which DNA may be spliced in order to bring about replication and cloning of such DNA. The cloning vehicle may further contain a marker suitable for use in the identification of cells transformed with the cloning vehicle. Suitable marker genes are for example antibiotic resistance providing marker genes, but other useful markers exist as well, e.g. biocide resistance providing genes as well as heavy metals, such as copper resistance providing genes. Alternatively, such markers may be provided on a cloning vehicle which is separate from that supplying the gene of interest using the so called cotransformation system. The word "vector" is sometimes used for "cloning vehicle."

Expression vehicle. An expression vehicle or vector is similar to a cloning vehicle but it is capable of expressing a gene of interest, after transformation into a desired host. When a fungal host is used, the gene of interest is preferably provided to a fungal host as part of a cloning or expression vehicle that integrates into the fungal chromosome. Sequences which derive from the cloning vehicle or expression vehicle may also be integrated with the gene of interest during the integration process. For example, in *T. reesei*, the gene of interest can be directed to the cbh1 locus.

The gene of interest may preferably be placed under the control of (i.e., operably linked to) certain control sequences such as promoter sequences provided by the vector (which integrate with the gene of interest). If desired, such control sequences may be provided by the host's chromosome as a result of the locus of insertion.

Expression control sequences on an expression vector will vary depending on whether the vector is designed to express a certain gene in a prokaryotic or eukaryotic host (for example, a shuttle vector, may provide a gene for selection in different microbial hosts) and may additionally contain transcriptional elements such as, enhancer elements, termination sequences, and/or translational initiation and termination sites.

Homologous. By an enzyme "homologous" to a host of the invention is meant that an untransformed strain of the same species as the host species naturally produces some amount of the native protein; by a gene "homologous" to a host of the invention is meant a gene found in the genome of an untransformed strain of the same species as the host species. By an enzyme "heterologous" to a host of the invention is meant that an untransformed strain of the same species as the host species does not naturally produce some amount of the native protein; by a gene "heterologous" to a host of the invention is meant a gene not found in the genome of an untransformed strain of the same species as the host species.

Xylanase. As used herein, a xylanase is a hemicellulase that cuts the β-1,4 bonds within the xylosic chain of xylan, (xylan is a polymer of D-xylose residues that are joined through β-1,4 linkages). Xylanase activity is synonymous with xylanolytic activity. More specifically xylanolytic activity means the an activity similar with or identical to the xylanolytic activity of *A. flexuosa* 35 kDa (AM35) and *A. flexuosa* 50 kDa (AM5O), the characteristics, e.g. the thermostability are more specifically described and defined in the detailed description and examples.

By an amino acid sequence that is an "equivalent" of a specific amino acid sequence is meant an amino acid sequence that is not identical to the specific amino acid sequence, but rather contains at least some amino acid changes (deletion, substitutions, inversions, insertions, etc.) that do not essentially affect the biological activity of the protein as compared to a similar activity of the specific amino acid sequence, when used for a desired purpose. Preferably, an "equivalent" amino acid sequence contains at least 85%-99% identity at the amino acid level to the specific amino acid sequence, most preferably at least 90% and in an especially highly preferable embodiment, at least 95% identity, at the amino acid level. In the case of larger deletions, e.g. the removal of the tail region, the comparison is performed to the amino acid sequence of the corresponding area in the original sequence.

Functional Domains. The term in relation to a secretable fungal protein includes e.g. the secretion signal (signal sequence or signal sequence and prosequence of the secretable protein or part of the protein), which contains sequences that permit the proteins or fusion constructions to be secreted. In other words, the term "functional domain" also means a region of a DNA sequence that encodes a specific region of a protein. In this invention the term "functional domain" includes, in addition to the regions of the DNA sequence encoding the amino acid sequence responsible for the catalytic or enzymatic function, other specific domains with other functions, e.g., a binding function. The binding function is responsible for the binding of xylan or cellulose to the respective protein. The specific domain can also be a folding domain, which is responsible for the tertiary structure of the protein, e.g., it encodes an α-helical or β-sheet structure of a protein or a combination thereof. The functional domain can also be responsible for the immunological activity of the protein. Thus, the "functional domain" might comprise a secretion signal or the core sequence or a sequence responsible for the folding of the protein as set forth above. Said functional domains can be totally separate from each other and are responsible for the "biological" activity of the protein. By the "biological" activity of a xylanase amino acid sequence of the invention is meant the enzymatic, functional, folding or binding activity or a combination of said activities.

Preparation or enzyme preparation. By "preparation or enzyme preparation" is meant a composition containing proteins or enzymes which are present in the culture medium and from which the host cells have been removed after the cultivation or fermentation has been completed. The preparation or enzyme preparation can be further processed by downstream-processing methods, which are appropriate for the application of the protein or enzyme. The proteins or enzymes can be either partially or completely isolated and purified. For bulk use the preparation or enzyme preparation is usually subjected to filtration and/or centrifugation to remove the host cells from the spent culture medium. Thus the term "preparation or enzyme preparation" in the present invention means crude enzyme preparations for bulk use, but also proteins or enzymes, which can be highly purified for special reasons.

By a host that is "substantially incapable" of synthesizing one or more enzymes is meant a host in which the activity of one or more of the listed enzymes is depressed, repressed, deficient, or absent when compared to the wild-type.

Enzyme-aided bleaching. By "enzyme-aided bleaching" is meant the extraction of residual lignin from paper making pulp after the action of hemicellulose degrading enzymes with or without lignin degrading enzymes. The removal or extraction of lignin may be restricted by hemicelluloses either physically (through reprecipitation onto the fibre surface during cooking) or chemically (through lignin-carbohydrate complexes). The hemicellulase activity partially degrades the hemicellulose, which enhances the extractability of lignins by conventional bleaching chemicals (like chlorine, chlorine dioxide, peroxide, etc.) (Viikari et al., "Bleaching with Enzymes" in *Biotechnology in the Pulp and Paper Industry*, Proc. 3rd Int. Conf., Stockholm, pp. 67-69 (1986); Viikari et al., "Applications of Enzymes in Bleaching" in *Proc. 4th Int. Symp. Wood and Pulping Chemistry*, Paris, Vol. 1, pp. 151-154 (1987); Kantelinen et al., "Hemicellulases and their Potential Role in Bleaching" in *International Pulp Bleaching Conference, Tappi Proceedings*, pp. 1-9 (1988)). The advantage of this improved bleachability is a lower consumption of bleaching chemicals and lower environmental loads or higher final brightness values. In the past, this has often been referred to as biobleaching.

II. Genetic Engineering of the Hosts of the Invention

The problem of producing bacterial proteins, preferably xylanases in a cost-effective manner in a large scale is solved by producing the proteins in filamentous fungi, e.g. *Aspergillus* or *Trichoderma*. The process for efficiently producing bacterial proteins in filamentous fungi is facilitated through the cloning of genetic sequences that encode the desired bacterial protein activity and through the expression of such genetic sequences in filamentous fungi. As used herein, the term "genetic sequences" is intended to refer to a nucleic acid molecule (preferably DNA). Genetic sequences that encode the desired proteins are derived from a variety of bacterial sources. These sources include actinomycetous DNA, cDNA, synthetic DNA and combinations thereof, preferably actinomycetous DNA, cDNA, synthetic DNA and combinations thereof encoding xylanase, most preferably *Actinomadura* genomic DNA, cDNA, synthetic DNA and combinations thereof. Vector systems may be used to produce hosts for the production of the enzyme preparations of the invention. Such vector construction (a) may further provide a separate vector construction (b) which encodes at least one desired gene to be integrated to the genome of the host and (c) a selectable marker coupled to (a) or (b). Alternatively, a separate vector may be used for the marker.

A nucleic acid molecule, such as DNA, is said to be "capable of expressing" a polypeptide if it contains expression control sequences which contain transcriptional regulatory information and such sequences are "operably linked" to the nucleotide sequence which encodes the polypeptide.

An operable linkage is a linkage in which a sequence is connected to a regulatory sequence (or sequences) in such a way as to place expression of the sequence under the influence or control of the regulatory sequence. Two DNA sequences (such as a protein encoding sequence and a promoter region sequence linked to the 5' end of the encoding sequence) are said to be operably linked if induction of promoter function results in the transcription of the protein encoding sequence MRNA and if the nature of the linkage between the two DNA sequences does not (1) result in the introduction of a frame-shift mutation, (2) interfere with the ability of the expression regulatory sequences to direct the expression of the mRNA, antisense RNA, or protein, or (3) interfere with the ability of the template to be transcribed by the promoter region sequence. Thus, a promoter region would be operably linked to a DNA sequence if the promoter were capable of effecting transcription of that DNA sequence.

The precise nature of the regulatory regions needed for gene expression may vary between species or cell types, but shall in general include, as necessary, 5' non-transcribing and 5' non-translating (non-coding) sequences involved with initiation of transcription and translation respectively.

Expression of the protein in the transformed hosts requires the use of regulatory regions functional in such hosts. A wide variety of transcriptional and translational regulatory sequences can be employed. In eukaryotes, where transcription is not linked to translation, such control regions may or may not provide an initiator methionine (AUG) codon, depending on whether the cloned sequence contains such a methionine. Such regions will, in general, include a promoter region sufficient to direct the initiation of RNA synthesis in the host cell.

As is widely known, translation of eukaryotic mRNA is initiated at the codon which encodes the first methionine. For this reason, it is preferable to ensure that the linkage between a eukaryotic promoter and a DNA sequence which encodes the protein, or a functional derivative thereof, does not contain any intervening codons which are capable of encoding a methionine. The presence of such codons results either in a formation of a fusion protein (if the AUG codon is in the same reading frame as the protein encoding DNA sequence) or a frame-shift mutation (if the AUG codon is not in the same reading frame as the protein encoding sequence).

In a preferred embodiment, a desired protein is secreted into the surrounding medium due to the presence of a secretion signal sequence. If a desired protein does not possess its own signal sequence, or if such signal sequence does not function well in the host, then the protein's coding sequence may be operably linked to a signal sequence homologous or heterologous to the host. The desired coding sequence may be linked to any signal sequence which will allow secretion of the protein from the host. Such signal sequences may be designed with or without specific protease sites such that the signal peptide sequence is amenable to subsequent removal. Alternatively, a host that leaks the protein into the medium may be used, for example a host with a mutation in its membrane.

If desired, the non-transcribed and/or non-translated regions 3' to the sequence coding for a protein can be obtained by the above-described cloning methods. The 3'-non-transcribed region may be retained for its transcriptional termination regulatory sequence elements; the 3'-non-translated region may be retained for its translational termination regulatory sequence elements, or for those elements which direct polyadenylation in eukaryotic cells.

The vectors of the invention may further comprise other operably linked regulatory elements such as enhancer sequences.

In a preferred embodiment, genetically stable transformants are constructed whereby a desired protein's DNA is integrated into the host chromosome. The coding sequence for the desired protein may be from any source. Such integration may occur de novo within the cell or, in a most preferred embodiment, be assisted by transformation with a vector which functionally inserts itself into the host chromosome, for example, DNA elements which promote integration of DNA sequences in chromosomes.

Cells that have stably integrated the introduced DNA into their chromosomes are selected by also introducing one or more markers which allow for selection of host cells which contain the expression vector in the chromosome, for example the marker may provide biocide resistance, e.g., resistance to antibiotics, or heavy metals, such as copper, or the like. The selectable marker gene can either be directly linked to the DNA gene sequences to be expressed, or introduced into the same cell by co-transfection.

Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Once the vector or DNA sequence containing the construct(s) is prepared for expression, the DNA construct(s) is introduced into an appropriate host cell by any of a variety of suitable means, including transformation as described above. After the introduction of the vector, recipient cells are grown in a selective medium, which selects for the growth of transformed cells. Expression of the cloned gene sequence(s) results in the production of the desired protein, or in the production of a fragment of this protein. This expression can take place in a continuous manner in the transformed cells, or in a controlled manner.

Accordingly, the bacterial protein encoding sequences may be operably linked to any desired vector and transformed into a selected filamentous fungi host, preferably *Trichoderma* host, so as to provide for expression of such proteins in that host.

To facilitate secretion of the bacterial protein, the bacterial protein encoding sequences may be fused in frame to other sequences so as to construct DNA encoding a fusion protein. For example, a recombinant vector encoding a xylanase gene from bacterial origin is fused with the sequence of a *Trichoderma* cellulase or hemicellulase, or one or more functional domains of said cellulase or hemicellulase as described in U.S. Pat. No. 5,298,405, WO 93/24622 and in Stálbrand et al., *Appl. Environ. Microbiol.* 61:1090-1097 (1995), each incorporated herein by reference. Especially, the enzyme is selected from the group consisting of cellobiohydrolases (CBHI and CBHII), endoglucanases (EGI and EGII), xylanases (XYLI and XYLII) and mannanase (MANI), or a domain thereof, such as the functional domain signal, preprosequence or the core sequence. MANI has the same domain structure as that of the cellulases: a core domain, containing the active site, a hinge domain containing a serine-threonine rich region, and a tail, containing the binding domain.

If a xylanase gene of bacterial origin is fused in frame to an *Aspergillus* sequence, the sequence is selected from the group consisting of secretable proteins like *A. niger* or *A. niger* var. awamori glucoamylase or one or more functional domains of said secretable proteins.

Fusion peptides can be constructed that contain an N-terminal mannanase or cellobiohydrolase or endoglucanase core domain or the core and the hinge domains from the same, fused to the *Actinomadura* xylanase sequence. The result is a protein that contains N-terminal mannanase or cellobiohydrolase or endoglucanase core or core and hinge regions, and a C-terminal *Actinomadura* xylanase. The fusion protein contains both the mannanase or cellobiohydrolase or endoglucanase and xylanase activities of the various domains as provided in the fusion construct. A further alternative is to use a gene coding for a modified or inactive mannanase or cellobiohydrolase or endoglucanase core domain or the core and hinge domains from the same, fused to *Actinomadura* xylanase sequences. The resulting fusion protein then contains the modified or inactive enzyme domain fused to a desired bacterial sequence.

It should be noted, however, that the whole core region may not be necessary to obtain secretion of the desired fusion protein. A shorter fragment of this domain may also be used, particularly a fragment of the domain containing secretory signals for the protein of interest or a sequence of a specific domain.

Fusion proteins can also be constructed such that the mannanase or cellobiohydrolase or endoglucanase tail or a desired fragment thereof, is included, placed before the *Actinomadura* xylanase sequence, especially so as to allow use of a nonspecific protease site in the tail as a protease site for the recovery of the xylanase sequence from the expressed fusion protein. Alternatively, fusion proteins can be constructed that provide for a protease site in a linker that is placed before the *Actinomadura xylanase*, with or without tail sequences.

Accordingly, this invention results in the production and secretion of bacterial enzymes in filamentous fungi. The bacterial protein or enzyme is encoded as a fusion to a gene of a secretable fungal protein, thereby resulting in a high level of expression and secretion. The improvement in secretion of bacterial enzymes is more than ten-fold compared to the production and secretion of bacterial proteins without a fusion of the bacterial protein encoding gene to a fungal gene encoding a secretable protein. When a mammalian protein like chymosin is produced as a fusion protein in *Aspergillus*, the level of production has been only 10-20% of the production levels of this invention (WO 90/15860). Similarly, the production level of immunoglobulins in *Trichoderma* has been only 10-20% of the production levels of this invention (WO 92/01797).

There are very few reports related to the production of proteins or enzymes of bacterial origin in filamentous fungi: the production of endoglucanase from *Cellulomonas fimi* (Gwynne et al., *Bio/Technology* 5: 713-719 (1987); and β-glucuronidase from *E. coli* (Punt et al., *J. Biotechnol.* 17. 19-34(1991) have been reported in *A. nidulans*. Of these enzymes, endoglucanase was secreted into the culture medium in the range of 10-15 mg protein per liter. β-glucuronidase was only detectable intracellularly.

Many of the studies on heterologous gene expression have concerned mammalian genes (van den Hondel et al., Heterologous gene expression in filamentous fungi, Ed. Bennett and Lasure. *More Gene Manipulations in Fungi* Academic Press, San Diego, U.S.A., pp. 396-428 (1991). So far, the initial yields of eucaryotic enzymes in filamentous fungi have been in a range of tens of mg per liter in shake flask cultivations. In the International patent publication WO 90/15860 secretion of chymosin by *A. niger* var. awamori was described using a fusion to the homologous glucoamylase gene. Nyyssönen et al., *Bio/Technology* 11: 591-595 (1993) describes the production of antibody fragments in *Trichoderma reesei*. The best yield of antibody fragments when produced as a fusion to the cellobiohydrolase 1 gene of *T. reesei* in the range of 40 mg per liter in a shake flask cultivation.

III. The Enzyme Preparations of the Invention

According to the invention, there is provided a method for producing enzymes of bacterial origin. These enzymes are synthesized as fusion proteins. The carrier protein in the fusion is a fungal protein or one or more functional domains of said protein that is readily secreted from the host.

The enzyme compositions of the invention satisfy, e.g. requirements of specific needs in various applications in the pulp and paper industry. These applications include, e.g. enzyme-enhanced bleaching of paper making pulp, enzymatic fiberization during beating, enzymatic increase of drainage rates and ink removal of secondary fibre as well as enzymatic pitch removal.

The invention is applied to produce enzyme preparation partially or completely deficient in cellulolytic activity (that is, in the ability to degrade cellulose) and enriched in xylanases desirable for enzyme-enhanced bleaching of chemical pulp. By deficient in cellulolytic activity is meant a reduced, lowered, depressed, or repressed capacity to degrade cellulose. Such cellulolytic deficient preparations, and the making of same by recombinant DNA methods, are described in U.S. Pat. No. 5,298,405, incorporated herein by reference. As described herein, xylanases may be provided directly by the hosts of the invention (the hosts themselves are placed in the wood processing medium). Alternatively, used medium from the growth of the hosts, or purified enzymes therefrom, can be used. Further, if desired activities are present in more than one recombinant host, such preparations may be isolated from the appropriate hosts and combined prior to use in the method of the invention.

To obtain the enzyme preparations of the invention, the recombinant hosts described above having the desired properties (that is, for example, hosts capable of expressing large quantities of the desired xylanase enzymes and optionally, those which are substantially incapable of secreting one or more cellulase enzymes) are cultivated under suitable conditions, the desired protein or enzymes are secreted from the hosts into the culture medium, and the enzyme preparation is recovered from said culture medium by methods known in the art.

The enzyme preparation is the culture medium with or without the native or transformed host cells, or is recovered from the same by the application of methods well known in the art. However, because the xylanase enzymes are secreted into the culture media and display activity in the ambient conditions of the hemicellulolytic liquor, it is an advantage of the invention that the enzyme preparations of the invention may be utilized directly from the culture medium with no further purification. If desired, such preparations may be lyophilized or the enzymatic activity otherwise concentrated and/or stabilized for storage. The enzyme preparations of the invention are very economical to provide and use because (1) the enzymes may be used in a crude form; isolation of a specific enzyme from the culture fluid is unnecessary and (2) because the enzymes are secreted into the culture medium, only the culture medium need be recovered to obtain the desired enzyme preparation; there is no need to extract an enzyme from the hosts.

If desired, an expressed protein may be further purified in accordance with conventional conditions, such as extraction, precipitation, chromatography, affinity chromatography, electrophoresis, or the like.

IV. Identification and Isolation of *Actinomadura flexuosa* Xylanases

Two xylanases have been identified, purified and cloned from *Actinomadura flexuosa*. Both of these xylanases have a pH optimum and thermostability that are desirable for the enzyme-aided bleaching of wood pulp. One of these xylanases has a molecular weight of about 35 kDa (AM35) and the other has a molecular weight of about 50 kDa (AM50).

The optimal temperature range for *A. flexuosa* xylanases in crude preparations is 70-80° C. at pH 6-7. At pH 8, the optimum temperature range of this xylanase preparation is 60-70° C. This is useful in kraft pulp bleaching because after kraft cooking, the pH of the pulp is alkaline.

In purified preparations, AM35 retains 80% of its activity, and AM50 retains 90% of its activity after 24 hours when incubated in the presence of BSA at pH 6.0 and 70° C. At 80° C., both AM35 and AM50 are most active at pH 6 but both exhibit a broad activity plateau between pH 5-pH 7, wherein about 80% of the activity is retained.

For the isolation of AM35 and AM50, the host *A. flexuosa* is available as depository accession number DSM43 186 from Deutsche Sammlung von Mikroorganismen und Zellkulturen GmbH, Mascheroder Weg lb, D-38124 Braunschweig, Germany. Both forms can be purified by passage through a series of chromatographic columns. A first purification step by DEAE Sepharose CL-4B retains about half of the xylanase activity when the sample is applied at pH 8.6-9 in 12.5 mM $Na_2HPO_4$; the other half-is found in the flow through.

Elution of the bound xylanase activity with a salt gradient results in an elution of a sharp, earlier eluting peak of activity and a broad, later eluting peak of activity. The sharp, earlier eluting peak retains its homogeneity when subjected to phenyl Sepharose CL4B chromatography. Samples taken from the later, broad peak of activity separate into at least two peaks when subjected to Phenyl Sepharose CL-4B chromatography. There is only weak cross-reactivity of these later eluting xylanases with a polyclonal antibody directed against *Thermomonospora fusca* xylanase.

By SDS-PAGE, the molecular weight of the xylanase in these pools from the DEAE retentate was about 50 kDa, while the molecular weights of the xylanases in the DEAE flow through was 30, 35, 40 and 50 kDa. Thus, *A. flexuosa* contains four to five xylanase protein bands.

V. Enzyme-aided Bleaching using the *Actinomadura flexuosa* Xylanases

The present invention comprehends a method for enzymatically treating plant biomass under conditions of high temperature of 50-90° C. and pH 5-8, and especially 60-85° C., pH 6-7 and most preferably 70-80° C. and pH 7.0 for one to two hours. In a preferred embodiment, plant biomass is treated with xylanases that are able to hydrolyze xylan chains in wood pulp at neutral or moderately alkaline pH and high temperature. Alternatively, enzyme treatment can be combined to chelating stages (metal removal stages) in which high temperatures but low pH values (4-6) are typically used.

Wood pulp is a composite material consisting primarily of a matrix of cellulose, hemicellulose, and lignin. A common procedure for wood pulp production is chemical pulping. One typical mode of chemical pulping is alkaline sulphate cooking, so called kraft cooking. Under the process conditions (high temperatures and high alkalinity), the cooking chemicals extract lignin out of the pulp. However, not all of the lignin is removed during cooking, but part of it, (about 5%), remains in the pulp. This residual lignin has to be removed in order to get pulp suitable for paper production.

Many processes have been developed for the removal of residual lignin. Typically, the wood pulp is treated with chlorine or other toxic chemicals in order to remove the lignin component and provide a bleached pulp. However, the toxic by-products of this chemical treatment have a negative impact upon the health and stability of the environment into which they are released. Consequently, there is a great need for developing alternative, more environmentally protective techniques for pulp bleaching. Treatment of the cooked pulp with enzymes that partially degrade hemicellulose, e.g., xylan, in the pulp, modifies the pulp so that the lignin becomes easier to extract or remove. This leads to improved bleachability which in turn gives the advantages of lower bleaching chemical consumption and lower environmental loads and/or higher final brightness.

Under the method of the present invention, an enzyme-aided bleaching technique is developed whereby thermostable and neutral xylanases can be used in such conditions that the need to adjust the pH and temperature after the cooking step is decreased or eliminated.

In a preferred embodiment, the process of the invention is carried out in vitro in wood pulp. The process involves placing the enzyme preparation, culture medium, or concentrated mixture containing xylanase into contact with the wood pulp. Routine calculations enable those in the art to determine the dosage of the xylanase enzyme used, treatment pH and temperature and other parameter variables.

The method of the present invention may be applied alone or as a supplement to other treatments that improve the removal of lignin from wood pulp. In a preferred embodiment, the present invention is used to enhance the bleachability of wood pulps, especially chemical pulps.

In a preferred embodiment, the xylanases used in the methods of the invention are preferably those of *A. flexuosa*, and especially the 35 kDa and/or 50 kDa xylanases of *A. flexuosa*. Especially, culture medium that contains the enzymes secreted as a result of the growth of the cells are useful in the methods of the invention, as are the culture medium that can be provided by a recombinant host that has been transformed with the xylanase encoding genes of the invention.

VI. Preferred and Further Embodiments and Applicability of the Invention

The invention describes an improved method of expressing and secreting proteins or enzymes originating from bacteria, especially from actinomycetes in filamentous fungi by using fusion protein techniques. More than 50-fold greater production and secretion levels than those observed in the original actinomycete strains have been obtained. The production and secretion levels were more than 10-fold higher than those previously observed when producing heterologous (mammalian or bacterial) enzymes in filamentous fungi. The invention, however, is not strictly limited to higher secretion levels. Lesser or greater levels of expression are acceptable. The main purpose of the invention is to provide an alternative method for producing enzymes originating from bacteria, especially actinomycete in filamentous fungi.

Thus, the invention is related to a recombinant expression vector for production of bacterial proteins in a filamentous fungal host. Said vector comprises a promoter operably linked to a DNA sequence of a filamentous fungus secretable protein or one or more functional domains of said protein, which is fused in frame with a DNA sequence encoding a bacterial protein.

Generally, the filamentous fungus secretable protein encoding DNA sequence encodes an enzyme, such as cellulases or hemicellulases. The enzymes can be homologous or heterologous to the secreting filamentous fungus, e.g. *Aspergillus* or *Trichoderma*. In the most preferred embodiments of the invention the DNA sequence encoding the filamentous fungus secretable protein is an enzyme, which is known to be secreted in significant amounts in *T. reesei*.

Useful proteins or enzymes to provide the objectives of the invention are for example *Aspergillus* glucoamylase, *Aspergillus* α-amylase, *Trichoderma* cellulase, *Trichoderma* hemicellulase, *Trichoderma* glucoamylase, *Hormoconis* glucoamylase, *Chaetomium* xylanase, and *Melanocarpus* cellulase, but the most preferred filamentous fungus secretable proteins are the following enzymes, which are homologous to *Trichoderma*, i.e. cellobiohydrolases (CBHI and CBHII), endoglucanases (EGI and EGII), xylanases (XYLI and XYLII) and mannanase (MANI).

The amino acid and DNA sequences of the enzymes mentioned above are well known from literature and some are described in the examples of the present invention below.

The DNA and amino acid sequences for *Hormoconis resinae* glucoamylase are described in Joutsjoki et al., *Curr. Genet.* 24:223-228 (1993); *Chaetomium* xylanase is described in International Patent Application PCT/FI96/00671; and *Melanocarpus* cellulase in International Patent Application PCT/FI96/00550, which citations hereby are incorporated by reference into the description of the invention. The skilled person can by using said sequences construct a multitude of alternative useful expression vectors according to the principals set forth in this application.

Because the main objective of the invention is the production of enzymes originating from bacteria or actinomycete, the recombinant expression vector of the present invention comprises a DNA sequence encoding an enzyme originating from a bacterium, preferably a xylanase or cellulase originating from an actinomycete.

Examples of such useful DNA sequences are those obtainable from *A. flexuosa* the DNA sequence SEQ ID NO: 1: encoding the amino acid sequence of SEQ ID NO: 2: or the DNA sequence SEQ ID NO: 3: encoding the amino acid sequence of SEQ ID NO: 4: or any equivalents of said amino acid sequences, wherein said equivalents have an xylanolytic activity similar to that of SEQ ID NO: 2: and SEQ ID No: 4:. Also some peptides of the *A. flexuosa* xylanases assigned SEQ ID NO: 12:, SEQ ID NO: 14:, SEQ ID NO: 16:, and SEQ ID NO: 18: are described below in the examples.

Useful DNA sequences can be found e.g. in the plasmids pALK923 (DSM9322), pALK938 (DSM9899), pALK939 (DSM9900, pALK940 (DSM9901), pALK941 (DSM9902) and pALK1056 (DSM9903) that encode the *Actinomadura flexuosa* AM35 xylanase and plasmids pALK927 (DSM9447) and plasmid pALK928 (DSM9448) that encode the *Actinomadura flexuosa* AM50 xylanase.

The recombinant expression vector of the present invention can alternatively contain a DNA sequence, which encodes *Thermomonospora fusca* cellulases, especially the T. fusca endocellulase EV (Lao et al., *J. Bacteriol.* 173: 3397-3407 (1991)).

The preferred promoters in the recombinant DNA expression vectors of the present invention are those of a filamentous fungus secretable protein, most preferably a *T. reesei* cbh1 promoter or *A. niger* glucoamylase promoter.

Examples of preferred recombinant expression vector are the plasmids pALK945, pALK948, pALK1021 and pALK1022. The plasmid pALK1022 is shown in FIG. 17. The constructs of the three other plasmids are essentially the same that of plasmid pALK1022 with the exception that the linker sequences are as those described in detail in the examples, e.g. SEQ ID NO: 11:, SEQ ID NO: 13:, SEQ ID NO: 15: and SEQ ID NO: 17:. Said expression vectors are used to transform filamentous fungi, such as *Aspergillus* and *Trichoderma*, most preferably *T. reesei*.

Hosts transformed with said expression vectors produce xylanases which all have the N-terminal amino acid sequence SEQ ID NO: 5:, which is identical with the N-terminal sequence (D-T-T-I-T-Q) of wild type *A. flexuosa* xylanase.

The transformed hosts are capable of expressing and secreting one or more proteins or enzymes, preferably xylanases or cellulases originating from bacteria or actinomycete into the culture medium during the cultivation or fermentation.

After the cultivation and removal of the host cells by filtration, centrifugation etc., the culture medium as such or concentrated provides a useful protein or enzyme preparation, which can be subjected to further down-stream processing methods for improved stability and storability. Alternatively, the preparation can be subjected to isolation and purification to obtain the desired protein or enzyme originating from bacteria or actinomycete in more purified form.

Examples of useful down-stream processes of the spent culture medium are e.g. filtration, ultrafiltration, precipitation, centrifugation, drying, evaporation, immobilization, granulation etc.

The preparation containing enzymes, especially xylanases and cellulases originating from actinomycetes and which are obtainable by cultivating hosts transformed with the expression vectors of the present invention are useful e.g. for enzyme-aided bleaching in because the enzymes are stable at processing temperatures, when the processing temperatures are in the ranges 50-90° C., preferably 60-85° C., most preferably 70-80° C.

Said preparations are also useful for treating paper pulp and for enzymatical treating of plant biomass.

Thus, the present invention provides an alternative and improved method for producing enzyme containing preparation of bacterial, more preferably of actinomycetous origin in a filamentous fungal host by first constructing recombinant expression vectors, in which a promoter is operably linked to a DNA sequence of a filamentous fungus secretable protein or one or more functional domains of said protein, which in turn contain, fused in frame, a DNA sequence encoding a bacterial protein; then transforming a filamentous fungal host with the thus constructed vectors and cultivating said transformed hosts in a culture medium and under culture conditions, which are optimal for the secretion of the enzyme. After the cultivation the host cells are separated from the culture medium, which can be used as an enzyme preparation as such or in concentrated form or after subjected to suitable down-stream processing methods.

The invention is described in more detail in the following examples, These examples show only a few concrete applications of the invention. It is self evident for one skilled in the art to create several similar applications. Hence the examples should not be interpreted to narrow the scope of the invention only to clarify the use of the invention.

EXAMPLES

Example 1

*Actinomadura flexuosa* DSM43186 Shake Flask and Fermentor Cultivations

The strain *A. flexuosa* DSM43186 was streaked on rolled oats mineral medium plate (Deutsche Sammlung von Mikroorganismen und Zellkulturen GmbH [German collection of microorganisms and cell cultures], *DSM Catalogue of strains*, 3rd ed., Braunschweig, Germany (1983); 1 liter contains 20 g agar, 20 g rolled oats, 1 ml trace element solution containing 100 mg $FeSO_4 \times 7$ $H_2O$, 100 mg $MnCl_2 \times 4$ $H_2O$, 100 mg $ZnSO_4 \times 7$ $H_2O/100$ ml; pH 9.0) and incubated at 50° C. until sporulating. A sporulating colony was inoculated in 10 ml of XPYB medium (Greiner-Mai, E. et al., *System. Appl. Microbiol.* 9:97-109 (1987); Holtz, C. et al., *Antonie van Leeuwenhoek* 59:1-7 (1991)); 1 liter contains 5 g oats spelt xylan, 5 g peptone from casein, 5 g yeast extract, 5 g beef extract, 0.74 g $CaCl_2 \times 2\ H_2O$; pH 9.0) and was incubated at 55° C. in a rotary shaker (250 rpm) for two to three days. An inoculum of 5 ml was then transferred to 250 ml of the same medium and incubated at the same conditions for three days. Xylanase activity obtained was 17 nkat/ml.

The procedure for two 1 L fermentations (Biostat M, B. Braun, Germany) was prepared as above. 10% (v/v) inoculum was used for the fermentations. The pH was maintained at pH 7.8±0.2 by addition of ammonia (12.5% (v/v)) and phosphoric acid (17% (v/v)), the fermentation temperature was 50° C. The fermentor was stirred at 400 rpm and the air flow was 1 L/min. Xylanase activities obtained were 32 and 58 nkat/ml (measured at pH 6.0 and 60° C. with 5 minutes incubation time). The culture media of the cultivations were used in protein purification and bleaching experiments.

Xylanase activities throughout the examples were measured according to Bailey, M. J. et al., *J. Biotechnol.* 23:257-270 (1992) using 1% (w/v) birch xylan (Roth no. 7500) as a substrate. The assay conditions were, if not otherwise stated, pH 5.3 and 50° C. with an incubation time of 5 minutes. One xylanase unit (1 nkat) is defined as the amount of enzyme that produces reducing carbohydrates having a reducing power corresponding to one nmole of xylose in one second from birch xylan under assay conditions. The International Unit (IU) is defined as the amount of enzyme that produces one micromole of measured end-product in one minute from the polymeric substrate, then 1 IU=16.67 nkat.

Example 2

Figure 1:
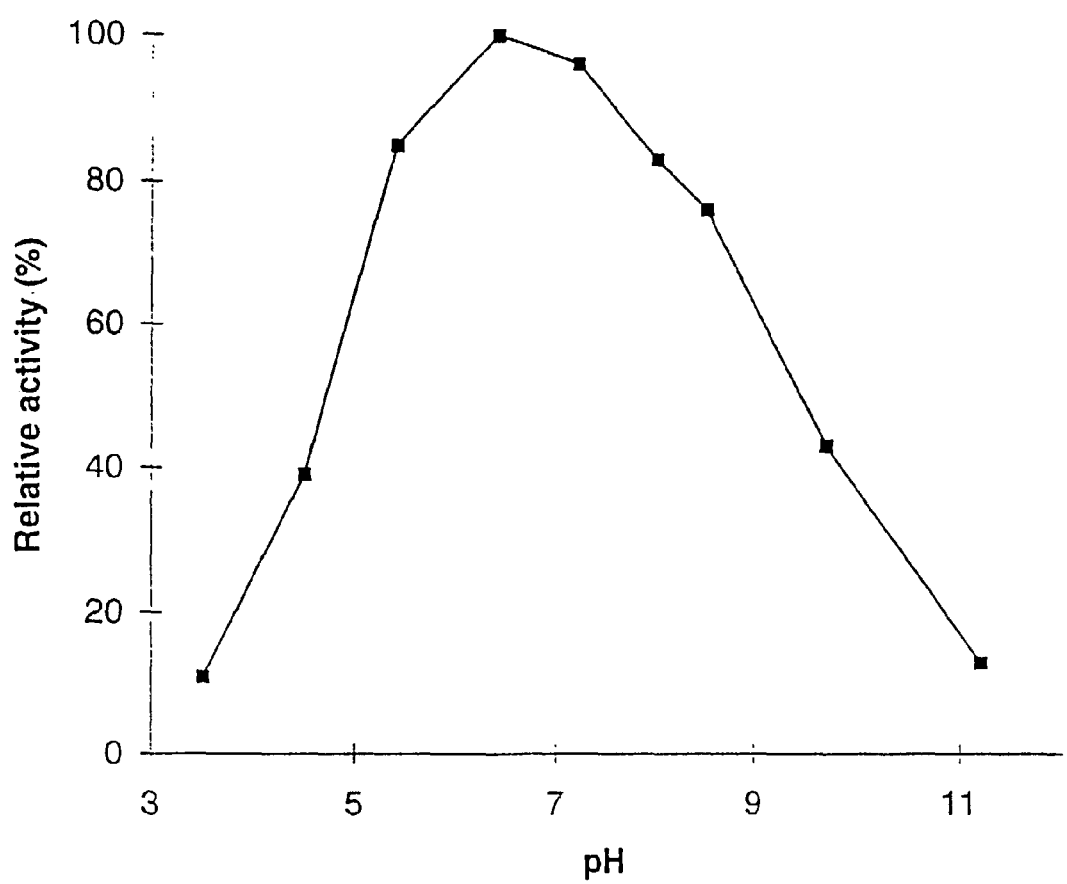

Determination of the pH and Temperature Dependencies of *Actinomadura flexuosa* Xylanase Activity from the Culture Medium To determine the pH dependency for the *A. flexuosa* xylanase activity, samples of the culture medium from the shake flask cultivation (Example 1) were diluted in 50 mM McIlvains buffers (50 mM citric acid-100 mM $Na_2HPO_4$) of pH-range 3.0-11.0. The final pH values of the enzyme buffer mixtures were 3.5, 4.5, 5.4, 6.4, 7.2, 8.0, 8.5, 9.7 and 11.2. Xylanase activity was measured at each pH at 50° C., 5 min reaction. The xylanase activity exhibited 80-100% of its maximum activity in the pH range of about 5.4-8.0, showing maximum activity at about pH 6.4 (FIG. 1).

Figure 2A:
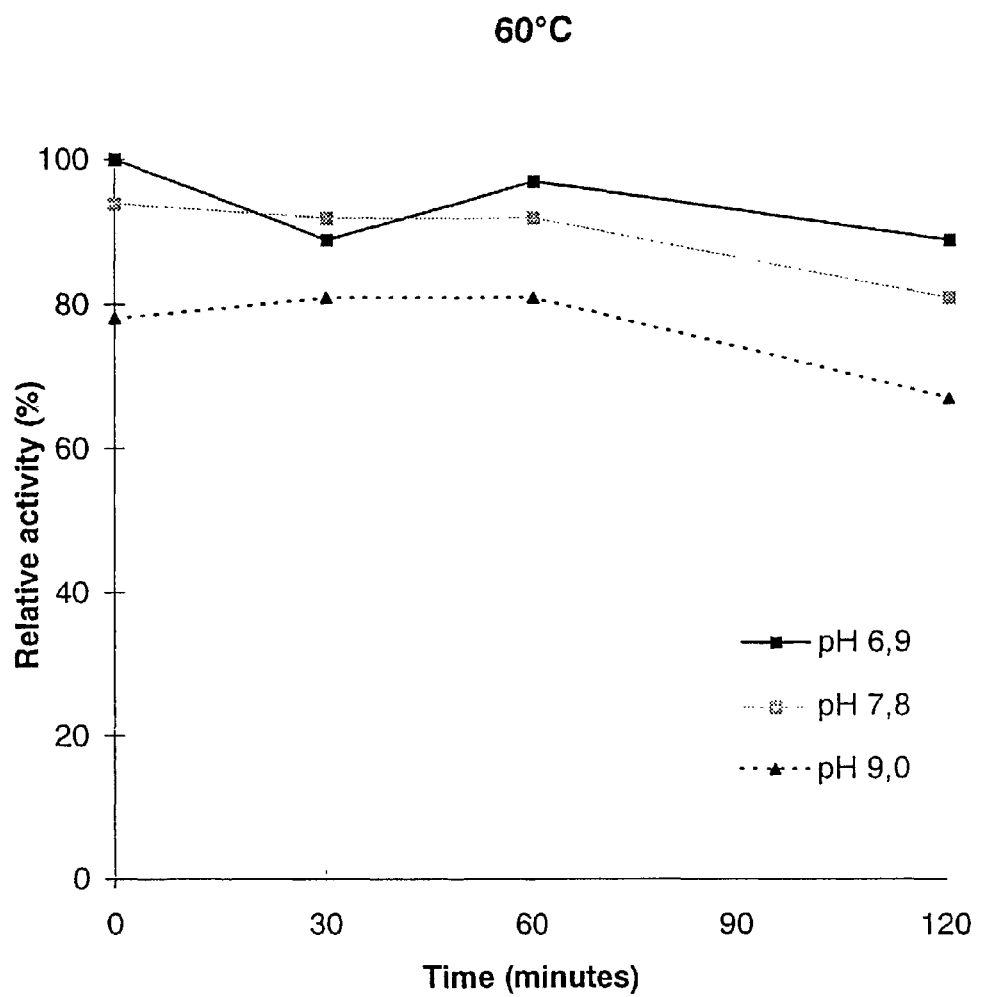
Figure 2B:
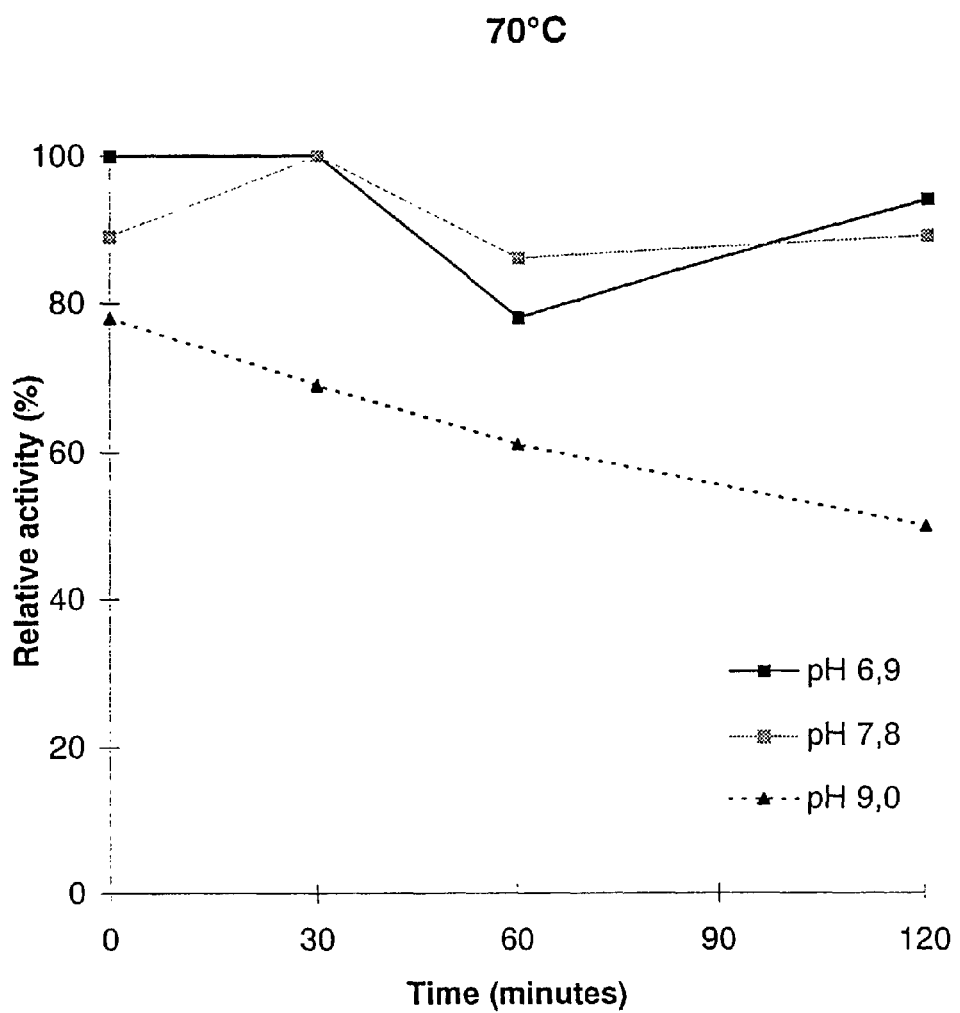
Figure 2C:
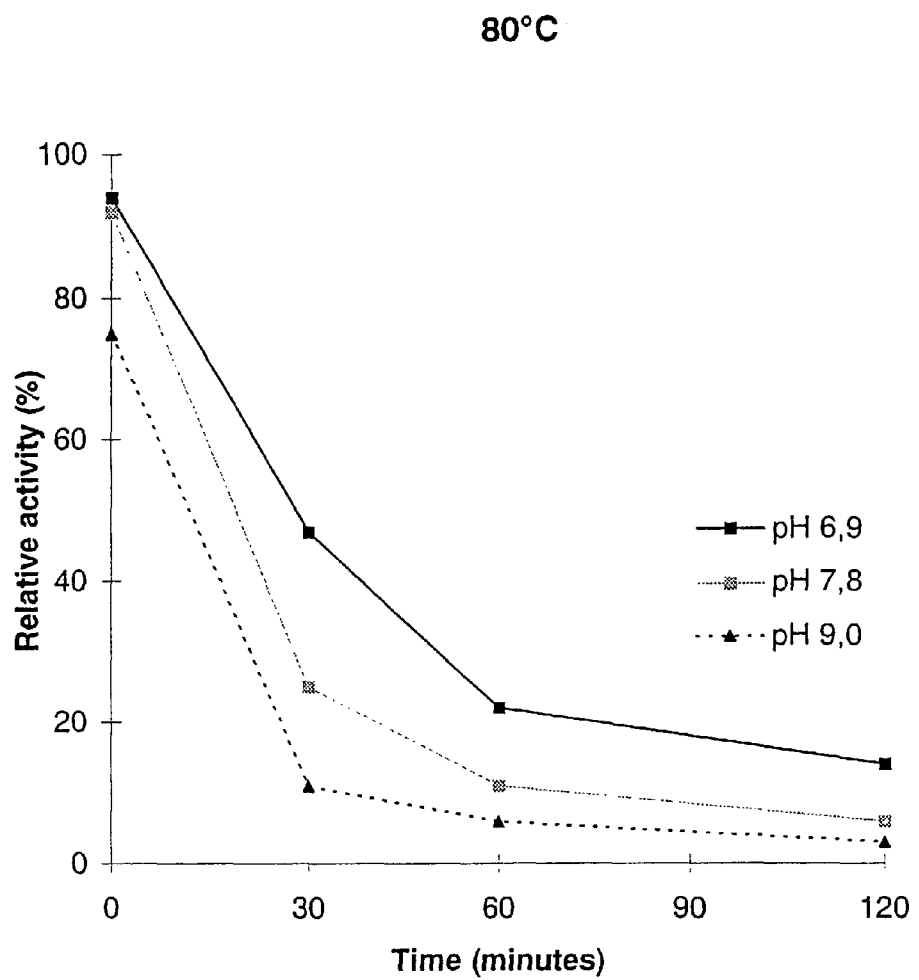

For, the thermal stability determination, samples from the culture supernatant were diluted in 50 mM McIlvain's buffers. Bovine serum albumin (BSA) was added to a concentration of 100 μg/ml and pepstatin A 10 μg/ml as well as phenyl methyl sulfonyl fluoride (PMSF) 174 μg/ml were added as protease inhibitors. The final pH values of the enzyme buffer mixtures were 6.9, 7.8 and 9.0. Samples were incubated in the absence of the substrate at 60° C., 70° C. and 80° C. Samples were taken at intervals of 0, 30, 60 and 120 minutes and immediately cooled on ice prior to the residual xylanase activity determination at 50° C. (5 min reaction in the corresponding pH). The enzyme was very stable when incubated at 60° C. and 70° C.; after 120 minutes incubation at 70° C. at pH 9 over 60% of xylanase activity was retained (FIG. 2A, 2B and 2C).

Example 3

Purification of *Actinomadura flexuosa* Xylanases

Purification of xylanases from *A. flexuosa* growth medium was performed at +4° C. with chromatographic columns coupled to a FPLC apparatus (Pharmacia). Xylanase activity measurements were performed at 50° C. and at pH 6.5. Protein was monitored at 280 nm throughout the purification. Samples were run on polyacrylamide slab gels containing 0.1% SDS on a Bio-Rad Mini Protean II electrophoresis system and stained with Coomassie Brilliant Blue. A polyclonal antibody prepared against *Thermomonospora fusca* xylanase A XynA, obtained from Prof. David Wilson, Cornell University, New York) was used to detect *A. flexuosa* xylanase(s) in Western blots. In the detection, Promega's ProtoBlot AP System was used.

A growth medium of the two 1 l fermentations described in Example 1 was pooled and centrifuged at 8,000 g for 30 min. The supernatant (1,500 ml) was diluted 1+2 with 12.5 mM $Na_2HPO_4$ pH 9 and adjusted to pH 8.6 with 1 M NaOH. This sample was applied, in two sets, on a DEAE Sepharose CL-6B (Pharmacia) ion-exchanger (2.5 x 29 cm) equilibrated with 12.5 mM $Na_2HPO_4$, pH 9, at 100 ml/h. The flow-through of both runs was combined and processed separately as described later.

Elution of the bound proteins from the DEAE-column (FIG. 3) was accomplished by a linear gradient (400 ml+400 ml) from 25 mM $Na_2HPO_4$ pH 9, to 25 mM $Na_2HPO_4$, pH 9 containing 1 M NaCl at a flow rate of 105 ml/h and fractions of 10 ml were collected. Two xylanase activity containing peaks could be collected (pool I and II), as well as a long "tailing" of the second peak (pool III).

The three pools (each combined from both DEAE runs) were adjusted to contain 2 M sodium chloride each and applied separately on a Phenyl Sepharose CL-4B (Pharmacia) column (2.5 ×15 cm) equilibrated with 25 mM $Na_2HPO_4$, pH 9 containing 2 M NaCl. Elution was performed at 100 ml/h with a two step gradient of 100% buffer A (25 mM $Na_2HPO_4$, pH 9) to 35% buffer B (25 mM $Na_2HPO_4$ containing 60% ethylene glycol) in 60 min followed by a steeper gradient from 35% B to 100% B in 60 min. Fractions of 7 ml (pool I) or 5 ml (pools II and III) were collected. The xylanase activity containing fractions of pool I obtained were pooled and named DEPS I (FIG. 4A). Both DEAE pools II and III resulted in two xylanase activity containing peaks named DEPS II/1, DEPS II/2 (FIG. 4B) and DEPS III/1, DEPS III/2 (FIG. 4C), respectively.

Samples of these pools were dialyzed against 25 mM $Na_2PO_4$, pH 9, over night and run on SDS-PAGE and stained for protein with Coomassie Blue (Figure SA) as well as analyzed by Western blots with *T. fusca* antibody (FIG. 5B). The antibody reacted only with two to three bands of smaller molecular mass (35 kDa or lower) from the growth medium and weakly with the proteins in these pools. The apparent molecular masses of the proteins in these pools were 50 kDa as estimated from SDS-PAGE with molecular mass standards. Pools DEPS II/2, DEPS III/1 and DEPS III/2 were the most pure.

The flow-through of the DEAE ion-exchanger (see above) was concentrated with a cut-off membrane of 30 kDa. Roughly half of the xylanase activity was found in the concentrate and half in the permeate. Both were adjusted to contain 2 M NaCl and applied on a Phenyl Sepharose 6 FastFlow (low sub; Pharmacia) column (2.5×34 cm) equilibrated with 25 mM $Na_2HPO_4$, pH 9, containing 2 M NaCl. Elution was accomplished at 300 mlh$^{-1}$ with the same gradient as was used for DEAE pools on Phenyl Sepharose CL-6B and fractions of 10 ml were collected. Xylanase activity containing peaks obtained were named KF1, KF2 and KF3 (FIG. 6B). The permeate from the concentration was subjected to an identical Phenyl Sepharose 6 FastFlow (low sub) run, and the xylanase activity containing fractions were named PF1 and PF2 (FIG. 6A). These peaks were dialyzed over night against 25 mM Na$_2$HPO$_4$, pH 9, and analyzed on SDS-PAGE as well as on Western blots (FIGS. 7A and 7B). The first peak, KF$_1$, from the concentrate showed a band of 40 kDa apparent molecular mass on SDS-PAGE, but no reaction on Western blots. However, this peak had the highest xylanase activity. KF2 showed a band of 50 kDa on SDS-PAGE reacting weakly with the antibody, but a clear band of 30 kDa could be seen on Western blots. The third peak, KF3, showed a band of 35 kDa on Western blots. The concentrate contained xylanases with apparent molecular weights of 50, 40, 35 as well as 30 kDa. The first peak, PF1, from the permeate reacted with *T. fusca* antibody showing two bands of 35 kDa and 30 kDa, respectively. PF2, on the other hand, showed only one band of 35 kDa on Western blots.

As a summary, *A. flexuosa* sp. DSM43186 growth medium contains xylanases with molecular mass of about 50 kDa (represented by pools DEPSII/2, DEPSIII/1 and DEPSIII/2), 40 kDa (represented by pool KF1), 35 kDa (represented by pool PF2 and KF3) and 30 kDa (represented by pool KF2). Of these, the 35 kDa and 50 kDa proteins appear as the major xylanase bands (on SDS-PAGE). It is possible that the 40 kDa xylanase band on SDS-PAGE is a degradation product of the 50 kDa band on SDS-PAGE and that the 30 kDa band on SDS-PAGE is a degradation product of 35 kDa xylanase band on SDS-PAGE.

Example 4

Production and Sequencing of Peptides from the Purified 35 kDa and 50 kDa Xylanases A sample (12 ml) of pool I from the DEAE Sepharose CL-6B (FIG. 3) run was subjected to gel exclusion chromatography on a HighLoad 26/60 Superdex G75 column (Pharmacia) equilibrated with 25 mM Na$_2$HPO$_4$, pH 9 at 120 ml/h. A sample (25 ml) of the xylanase activity containing peak fraction obtained was diluted (1+1) with water and applied on a mono Q (Pharmacia) ion-exchanger equilibrated with 12.5 mM Na$_2$HPO$_4$, pH 9. Elution was performed at 30 ml/h with a linear gradient from 12.5 mM Na$_2$HPO$_4$, pH 9 to 12.5 mM Na$_2$HPO$_4$, pH 9 containing 0.5 M NaCl in 50 min. The xylanase activity containing peak (1 ml) was concentrated on a Centricon micro concentrator (cut-off 30 kDa) and eluted with 1% ammonium bicarbonate. This concentrated sample containing a single 50 kDa protein band on SDS-PAGE was evaporated and alkylated with vinylpyridin. The alkylated sample was digested with trypsin (modified trypsin, sequenal grade, Promega V5111). The digest was applied on a reverse phase column coupled to an HPLC, and peaks absorbing at 214 nm were collected manually. Each of the collected fractions were subjected to Edman degradation in a gas-pulsed-liquid-phase sequencer (Kalkkinen & Tilgmann, *J. Protein Chem.* 7:242-243 (1988)) and the released PTH amino acids were analyzed on-line by using narrow bore reverse phase HPLC.

A sample of purified 35 kDa xylanase (purified essentially as described in Example 3) was subjected to Edman Degradation as above.

Peptides obtained from the purified 50 kDa xylanase and the N-terminal sequence of the purified 35 kDa xylanase are listed in Table 1.

TABLE 1

Peptides from the purified 50 kDa xylanase and the N-terminal sequence of the purified 35 kDa xylanase

| Peptide | Sequence |
| --- | --- |
| # 1696 | Ala-Ala-Ser-Thr-Leu-Ala-Glu-Gly-Ala-Ala-Gln-His-Asn-Arg |
| # 1697 | Tyr-Phe-Gly-Val-Ala-Ile-Ala-Ala-Asn-Arg |
| # 1698 | Leu-Asn-Asp-Ser-Val-Tyr-Thr-Asn-Ile-Ala-Asn-Arg |
| # 1699 | Asn/Gly/X-Thr-Gly-Ile-Thr-Val-X-Gly-Val |
| # 1703 | His/Glu/Thr-Glu/Phe-Leu/Asn-Val/Ser-Tyr/Val-Asn/Thr-Met/Ala-Val/Glu-Asn/X-Glu/X-Met/X |
| # 1704 | Glu-Phe-Asn-Ser-Val-Thr-Ala-Glu-Asn-Glu-Met-(Lys) |
| 35 kDa N-term | Asp-Thr-Thr-Ile-Thr-Gln |

The combination of the 50 kDa xylanase peptide sequences #1696 (SEQ ID NO: 6), #1697 (SEQ ID NO: 7), #1698 (SEQ ID NO: 8) and #1704 (SEQ ID NO: 10) corresponds with 75% similarity to amino acids 42-89 in *Streptomyces lividans* xylanase A (accession number M64551). The peptide #1703 has not been assigned any SEQ ID NO, because the multitude of alternatives present in the sequence and because it is not claimed. In addition, peptide #1699 (SEQ ID NO: 9:) shows 78% similarity to amino acids 301-309 in *S. lividans* XlnA:

```
                       #1696              #1697           #1698             #1704
Actinomadura
     50 kDa    1 AASTLAEGAAQHNR  YFGVAIAANR  LNDSVYTNIANR  EFNSVTAENEMK 48
                 |.|||:.:|||  .|  |||.|||..|  |.||.||.||.|  |||  ||||||||
  S.lividans   42 AESTLGAAAAQSGR  YFGTAIASGR  LSDSTYTSIAGR  EFNMVTAENEMK 89
        XlnA

#1699
Actinomadura     G
     50 kDa     NTGITVXGV
                 ||||:||
  S.lividans    SRCLGITVWGVRD
        XlnA  300         310
```

The sequences of *S. lividans* are present for comparison only.

Example 5

The pH Properties and Temperature Stability of the Purified 35 kDa and 50 kDa Xylanases The temperature stability of the purified 35 and 50 kDa enzymes with or without 100/Ag/ml BSA was determined by incubating the enzyme samples at 70° C., pH 6.0 for a period of 0, 2, 6 and 24 hours after which the xylanase activity of the samples was determined (at pH 6.5, 60° C., 20 min reaction). In the samples into which BSA had been added, over 80% of the original activity could be measured even after 24 h of incubation (FIGS. 8 and 9 for the 35 kDa and the 50 kDa xylanases, respectively). When BSA was not added, still about 60% (35 kDa) or 70% (50 kDa) of the original activity was measured after 24 h of incubation (FIGS. 8 and 9).

The pH dependence was determined by incubating the enzyme samples at different pH values (pH 4-8) and at temperatures of 80° C. (35 kDa) and 60, 70 and 80° C. (50 kDa) for 20 minutes (35 kDa) or 10 minutes (50 kDa). At 80° C., the 35 kDa xylanase showed a pH optimum of around pH 6 having nearly 90% of its activity from about pH 5 to 7 (FIG. 10A). At 60° C. and 70° C., the 50 kDa xylanase showed a pH optimum of pH 5-7 and at 80° C., a pH optimum of pH 6-7. The enzyme was very stable from pH 5-7 under these conditions (FIG. 10B). Incubation of both 35 kDa and 50 kDa xylanases at 60° C. for 60 minutes at pH values from 4.2 to 8.7 showed similar stability as found in the above experiment, except that the 50 kDa xylanase seems to be less stable at pH 4.2 under these conditions (FIG. 10C). Temperature dependence experiments at pH 7 with 60 minute incubations of the 35 kDa and 50 kDa xylanases with substrate at temperatures of 50, 60, 70 and 80° C. showed maximal activity at 70 IC for both enzymes (FIG. 11). The 50 kDa xylanase seemed from these results to be slightly more stable at 80° C. and pH 7 than the 35 kDa xylanase. On the other hand, the 35 kDa xylanase showed more activity and stability in the pH range of 4-5 (FIGS. 10A-10C).

Example 6

Bleaching Experiments Using *Actinomadura flexuosa* Culture Medium

Bleaching experiments were done to determine the usefulness of *A. flexuosa* xylanase activity in both ECF (elementary chlorine free) and TCF (totally chlorine free) bleaching of kraft pulp.

ECF Bleaching

Growth medium containing *A. flexuosa* xylanase activity (Example 1) was added to Finnish oxygen delignified softwood kraft pulp (kappa number 15) in the amount of 50 or 100 nkat/g pulp dry matter. Xylanase activity was measured at pH 6 and 60° C. with 5 minutes incubation time. Cellulase activity of the growth medium was very low. The enzyme treatments were done at pH 7 and 70° C. for one hour. Reference pulp was kept under the same conditions without enzyme addition.

After the enzyme treatments pulps were bleached in two stages: chlorine dioxide stage and alkaline extraction. The absorbance of the filtrate at 280 nm was determined to estimate the amount of dissolved lignin.

As can be seen in Table 2, after the pretreatment with the xylanase preparation more residual lignin was removed from the pulps as evidenced by the increase of $A_{280}$ of the filtrates and reduction of kappa numbers in the final pulps. The final pulps had also 3-4 units higher brightness compared with the reference. The strength of the pulps was not affected, because the viscosity values stayed inside the normal variation of the method.

TABLE 2

|  | Reference | 50 nkat/g | 100 nkat/g |
|---|---|---|---|
| Enzyme treatment | | | |
| Consistency, % | 3 | 3 | 3 |
| Retention time, hours | 1 | 1 | 1 |
| Enzyme dosage, nkat/g | 0 | 50 | 100 |
| Temperature, ° C. | 70 | 70 | 70 |
| pH, start/end | 7.0/7.1 | 7.0/7.2 | 7.2/7.4 |
| Absorbance, 280 nm | 0.22 | 0.49 | 0.65 |
| ClO₂ stage | | | |
| Consistency, % | 3 | 3 | 3 |
| Retention time, hours | 1 | 1 | 1 |
| ClO₂ dosage, % | 2.3 | 2.3 | 2.3 |
| Temperature, ° C. | 60 | 60 | 60 |
| pH at the end | 2.4 | 2.5 | 2.5 |
| Extraction stage | | | |
| Consistency, % | 10 | 10 | 10 |
| Retention time, hours | 1 | 1 | 1 |
| NaOH dosage, % | 1.5 | 1.5 | 1.5 |
| Temperature, ° C. | 70 | 70 | 70 |
| pH at the end | 10.9 | 10.9 | 10.9 |
| Final Pulp | | | |
| Brightness, % ISO | 56.7 | 59.9 | 60.6 |
| Kappa number | 6.6 | 5.6 | 5.4 |
| Viscosity, ml/g | 920 | 910 | 900 |

TCF Bleaching

Finnish oxygen delignified softwood kraft pulp (kappa number 15) was treated with *A. flexuosa* xylanase preparation using enzyme dosages of 50 and 100 nkat/g pulp dry matter. Xylanase activity was measured at pH 6 and 60° C. with 5 minutes incubation time. Cellulase activity of the preparation was very low. The enzyme treatments were done at pH 7 and 70° C. for one hour. Reference pulp was kept under the same conditions without enzyme addition.

After the enzyme treatments the pulps were bleached using QP sequence. Metals were first removed by chelating with 0.2% EDTA (chelating stage, Q) and the pulps were then bleached with hydrogen peroxide (peroxide stage, P). Bleaching chemicals were the following: 3% $H_2O_2$, 3% NaOH 0,2% DPTA (diethylene triamine pentaacetic acid) and 0.5% $MgSO_4$. The absorbance of the filtrate at 280 nm was determined to estimate the amount of dissolved lignin. The results are shown in Table 3.

TABLE 3

|  | Reference | 50 nkat/g | 100 nkat/g |
|---|---|---|---|
| Enzyme treatment | | | |
| Consistency, % | 3.5 | 3.5 | 3.5 |
| Retention time, hours | 1 | 1 | 1 |
| Enzyme dosage, nkat/g | 0 | 50 | 100 |
| Temperature, ° C. | 70 | 70 | 70 |
| pH, start/end | 7.0/7.4 | 7.0/7.3 | 7.0/7.3 |
| Absorbance, 280 nm | 0.27 | 0.43 | 0.57 |
| Chelation stage, Q | | | |
| Consistency, % | 3.0 | 3.0 | 3.0 |
| Retention time, hours | 1 | 1 | 1 |
| EDTA, % of dry matter | 0.2 | 0.2 | 0.2 |
| Temperature, ° C. | 70 | 70 | 70 |
| pH at the end | 5.5 | 5.6 | 5.8 |
| Absorbance, 280 nm | 0.24 | 0.44 | 0.64 |
| Peroxide stage, P | | | |
| Consistency, % | 10 | 10 | 10 |
| Retention time, hours | 3 | 3 | 3 |
| Temperature, ° C. | 80 | 80 | 80 |
| pH at the end | 10.6 | 10.6 | 10.6 |

TABLE 3-continued

|  | Reference | 50 nkat/g | 100 nkat/g |
|---|---|---|---|
| Peroxide dosage, % | 3.0 | 3.0 | 3.0 |
| Peroxide consumed, % | 2.1 | 2.2 | 2.1 |
| Final Pulp |  |  |  |
| Brightness, % | 71.9 | 72.9 | 73.0 |
| Kappa number | 9.0 | 8.3 | 7.9 |
| Viscosity, ml/g | 870 | 890 | 890 |

Table 3 shows that according to the measured $A_{280}$ values and kappa numbers, significantly more lignin was removed after the xylanase treatments compared with the reference. The viscosity values of the pulps remained inside the normal variation of the method, which means that the strength of the pulps was not affected. Also brightness values were higher than reference, but as expected the increase was slighter than in chlorine dioxide bleaching.

Example 7

Bleaching Experiments Using the Purified 35 kDa and 50 kDa Xylanases

The purified larger 50 kDa (AM50) xylanase and the smaller 35 kDa (AM35) xylanase (including also the 30 kDa xylanase) were tested in a three stage peroxide bleaching. The purified enzyme preparations were the same as used in the determination of the pH and temperature properties of the purified enzymes (Example 5).

The purified enzyme preparations were added to Finnish oxygen delignified softwood kraft pulp (kappa number 13.5 and brightness 37%) in the amount of 100 nkat/g pulp dry matter. Xylanase activity was measured at pH 6.5 and 60° C. with 5 minutes incubation time. The enzyme treatments were done at pH 6.5 and 60° C. for one hour. Reference pulp was treated in the same conditions but without enzyme addition. Bleaching was performed with $QP_1P_2P_3$ sequence. The chelation stage (Q) was performed by adding EDTA to 0.2% of pulp dry matter. The three hydrogen peroxide stages ($P_1P_2P_3$) were all carried out the same way. The results are shown in Table 4.

TABLE 4

|  | Reference | AM50 | AM35 |
|---|---|---|---|
| Enzyme treatment |  |  |  |
| Consistency, % | 3.5 | 3.5 | 3.5 |
| Retention time, hours | 1 | 1 | 1 |
| Enzyme dosage, nkat/g | 0 | 100 | 100 |
| Temperature, ° C., start/end | 60/59 | 58/58 | 60/59 |
| pH, start/end | 6.6/6.6 | 6.8/6.8 | 6.7/6.7 |
| Chelation stage, Q |  |  |  |
| Consistency, % | 3.0 | 3.0 | 3.0 |
| Retention time, hours | 1 | 1 | 1 |
| EDTA, % of dry matter | 0.2 | 0.2 | 0.2 |
| Temperature at the end, ° C. | 50 | 49 | 51 |
| pH at the end | 4.6 | 5.4 | 4.8 |
| $P_1$ stage |  |  |  |
| Consistency, % | 10 | 10 | 10 |
| Retention time, hours | 3 | 3 | 3 |
| Temperature, ° C. | 80 | 80 | 80 |
| pH, start/end | 12.0/11.7 | 12.1/12.0 | 11.9/11.7 |
| Peroxide dosage, % | 3.0 | 3.0 | 3.0 |

TABLE 4-continued

|  | Reference | AM50 | AM35 |
|---|---|---|---|
| Peroxide consumed, % | 2.7 | 2.7 | 2.6 |
| Brightness, % | 59.6 | 62.3 | 63.7 |
| Kappa number | (5.9) | 6.3 | 5.3 |
| $P_2$ stage |  |  |  |
| Consistency, % | 10 | 10 | 10 |
| Retention time, hours | 3 | 3 | 3 |
| Temperature, ° C. | 80 | 80 | 80 |
| pH, start/end | 12.2/11.7 | 12.2/11.7 | 12.1/11.6 |
| Peroxide dosage, % | 3.0 | 3.0 | 3.0 |
| Peroxide consumed, % | 2.2 | 2.4 | 2.2 |
| Brightness, % | 67.2 | 69.7 | 70.7 |
| Kappa number | 6.8 | 4.8 | 4.9 |
| $P_3$ stage |  |  |  |
| Consistency, % | 10 | 10 | 10 |
| Retention time, hours | 3 | 3 | 3 |
| Temperature, ° C. | 80 | 80 | 80 |
| pH, start/end | 11.9/12.0 | 12.0/11.6 | 12.0/11.8 |
| Peroxide dosage, % | 3.0 | 3.0 | 3.0 |
| Peroxide consumed, % | 2.1 | 2.2 | 2.0 |
| Brightness, % | 71.3 | 74.0 | 74.4 |
| Kappa number | 5.2 | 4.1 | 2.2 |
| Total peroxide consumption, % | 7.0 | 7.3 | 6.8 |

The use of AM50 and AM35 clearly increased the, brightness without significantly increasing the amount of peroxide that was consumed. Also lignin content of pulps was reduced which is evidenced by the reduction of kappa numbers of pulps treated with these enzymes.

Example 8

Isolation of the Chromosomal DNA and Construction of the Genomic Library

*Actinomadura flexuosa* DSM43186 was cultivated in 50 ml of medium consisting of 10% (w/v) sucrose, 0.5% (w/v) oat spelt xylan, 0.5% (w/v) peptone from casein, 0.5% (w/v) yeast extract, 0.5% (w/v) beef extract, 0.074% (w/v) $CaCl_2 \times 2H_2O$, pH 7.4-7.5, in baffled shake flask for 2.5 days at 52° C. with shaking at 200 rpm. 2.5 ml of this culture was transferred to 50 ml of fresh medium supplemented with 0.8% glycine, and grown for 2 days at 50° C., 200 rpm. Cells were pelleted by centrifugation and washed with 10% sucrose-25mM Tris-HCl (pH 8.0)-25mM EDTA.

The chromosomal DNA was isolated according to Hopwood et al., Genetic manipulation of *Streptomyces*: A laboratory manual, The John Innes Foundation, Norwich, UK (1985). Briefly, the mycelium was lysed with lysozyme and 2×Kirby mixture (2 g sodium triisopropylnaphthalene sulphonate, 12 g sodium 4-amino-salicylate, 5 ml 2 M Tris-HCl (pH 8.0), 6 ml of Tris-HCl saturated phenol, made up to 100 ml with water). The DNA was precipitated with isopropanol and dissolved into TE (10 mM Tris-HCl, 1 MM EDTA, pH 8.0). RNA was digested with RNase.

The chromosomal DNA was partially digested with Sau3A (Boehringer, Germany) and size-fractionated in sucrose gradient (10-40% (w/v) sucrose in 1 M NaCl, 20 mM Tris-HCl, pH 8.0, 5 mM EDTA) run at 55 000 rpm for 6h at 22° C. in the Beckman TL-100 ultracentrifuge in the TLS-55 rotor. The gradient was divided in fractions, and those containing DNA of mainly 7-10 kb in size were used to construct a genomic *Actinomadura* library.

The predigested ZAP Express™ BamHI/CIAP Vector Cloning Kit (Stratagene; U.S.A.) was used to construct the library and the instructions of the manufacturer were followed in all the subsequent steps. Briefly, about 200 ng of size-fractionated DNA was ligated into 1 µg of ZAP Express™ prepared arms, and packaged using Gigapack II packaging extract (Stratagene, U.S.A.). The titer of the library was determined by infecting *E. coli* XL1-Blue MRF cells with serial dilutions of the packaged phage and plating on NZY plates. The total titer of the ligation mixture was approximately $3\times10^7$ pfu/ml, with over 96% insert frequency. The library was used for screening without amplification.

Example 9A

Isolation of the Gene Encoding the 35 kDa Xylanase on the Basis of Hydrolyzing Activity on RBB-Xylan Plates The genomic library of *Actinomadura flexuosa* DSM43186 DNA in ZAP Express™ vector was screened for xylanolytic activity, as follows. The host, Stratagene *E. coli* XL-Blue MRF' cells were grown in LB+0.2% (w/v) maltose+ 10 mM MgSO$_4$ and adjusted to OD$_{600}$=0.5. The cells were infected with the recombinant library for 15 min at 37° C. and plated with NZY top agar on the NZY plates. The plates were incubated for 4 hrs at 42° C., overlaid with nitrocellulose filters saturated with 10 mM IPTG to induce the lacZ-fusion protein expression, and incubated over night at room temperature.

The filters were washed with 50 mM K-phosphate buffer (pH 6.8), and transferred onto RBB-xylan+kanamycin (Km) plates. The plate has two layers; lower layer of 15 ml of regular LB+Km (40 Ag/ml) and upper layer of 5 ml of RBB xylan (0.5% (w/v) RBB xylan, 1% (w/v) oats spelts xylan in LB+Km, buffered with 50 mM K-phosphate, pH 6.8). The plates were transferred to 50° C. for a second night to determine xylanolytic activity. Filters were removed, and the clear halo on the RBB-xylan+Km plates revealed the clones having xylanase activity. 22 positive plaques from the original NZY- plates were picked in SM buffer/chloroform.

The ZAP Express™ vector has been designed to allow simple, efficient in vivo excision and recircularization of any cloned insert contained within the lambda vector to form a phagemid containing the cloned insert. Briefly, the positive clones were incubated with XL1 Blue MRF cells with the ExAssist helper phage. After heat denaturation (70° C., 15 min), and centrifugation, the excised phagemid pBK-CMV is packaged as filamentous phage particles in the supernatant. The rescued phagemid was mixed with XLOLR cells, and plated on LB/kanamycin (50 µg/ml) according to the manufacturer.

*E. coli* XLOLR cells transformed with the rescued phagemid DNAs were retested on RBB-xylan+Km. From the 22 originally positive clones 12 retained the xylanase activity. The phagemid DNAs were digested with EcoRI-PstI, electrophoresed, blotted onto a nylon membrane, and hybridized with a digoxigenin-labeled 1.15 kb *T. fusca* xylanase fragment from pALK185 (FIG. 12). The plasmid pALK185 contains the *T. fusca* xynA gene from pTX101 (Ghangas, G.S. et al., *J. Bact.* 171:2963-2969 (1994)). Four phagemids hybridized with the *T. fusca* DNA probe, indicating that they carried gene(s) sharing some homology with the *T. fusca* fragment. These phagemids were designated pALK938, pALK939, pALK940 and pALK941. From the *A. flexuosa* DSM43186 chromosomal DNA, the *T. fusca* xynA probe hybridized to about a 4 kb EcoRI-PstI fragment.

Example 9B

Isolation of the Gene Encoding for the 35 kDa Xylanase on the Basis of Hybridizing to the *Thermomonospora fusca* xynA Gene The genomic library of *Actinomadura flexuosa* DSM43186 DNA in ZAP Express vector was screened with a digoxigenin-labeled 1.15 kb *T. fusca* xylanase fragment from pALK185 (FIG. 12), according to supplier's instructions. 17 positive clones were picked. The phagemids were excised in vivo, as described above in example 9A. The *E. coli* clones harboring the positive phagemids were tested for xylanolytic activity on RBB-xylan, as described above in example 9A. 11 clones showed xylanolytic activity. One of the clones was chosen, and the plasmid was designated pALK1056.

Example 10

Isolation of the Gene Encoding the 35 kDa Xylanase on the Basis of Production of Polypeptide recognized by the *Thermomonospora fusca* XynA Antibody The polyclonal antibody against *T. fusca* 32 kDa xylanase, XynA (See Example 3), was used to screen the *Actinomadura flexuosa* DSM 43186 genomic library. Stratagene XL1-Blue MRF' cells were grown in LB+0.2% maltose+10 mM MgSO$_4$ and diluted to OD$_{600}$=0.5. The cells were infected with the recombinant library for 15 min at 37° C. and plated with NZY top agar on the NZY plates. Plates were incubated for 3.5 hours at 42° C., overlaid with nitrocellulose filters saturated with 10 mM IPTG, and incubated overnight at room temperature. Detection was performed with the 1:1500 diluted *T. fusca* XynA antibody using Promega's ProtoBlot AP System. Twelve positive clones, of which the clone 1.1 clearly gave the strongest signal, were picked in SM buffer/chloroform, and purified with a second round of screening.

The phagemids were excised in vivo, as described above in example 9A. The phagemids were then digested with EcoRI and PstI, electrophoresed, blotted onto a nylon membrane and hybridized with a digoxigenin-labeled 1.15 kb *T. fusca* xylanase fragment from pALK185 (FIG. 12). Of the *A. flexuosa* DSM43186 chromosomal DNA, the *T. fusca* xynA probe hybridized to about a 4 kb EcoRI-Pst fragment. The clones were also tested for xylanolytic activity on RBB-xylan, as described above in example 9A. One clone (clone 1.1) was positive in both screens. The phagemid carried by this clone was designated pALK923.

Example 11

Restriction Enzyme Analysis and Sequencing of the Xylanase Gene Coding for the 35 kDa Protein The plasmids pALK938 (DSM9399), pALK939 (DSM9900), pALK940 (DSM9901), pALK941 (DSM9902), pALK1056 (DSM9903) and pALK923 (DSM9322) were analyzed by restriction enzyme analysis, and were used for sequencing of the xylanase gene. The DNA was sequenced by using ABI (Applied Biosystems, U.S.A.) kits based on fluorescent-labeled T3 and T7 primers, or sequence-specific primers with fluorescent-labelled dideoxynucleotides, by the Taq dye primer cycle sequencing protocol in accordance with the supplier's instructions. Because of the high GC content in the *A. flexuosa* DNA, the sequencing reactions were performed with 10% (v/v) DMSO, at annealing temperature of 58-60° C. Sequencing reactions were analyzed on ABI 373A sequencer, and the sequences obtained were characterized by using the Genetics Computer Group Sequence Analysis Software Package, version 7.2. The DNA sequence encoding the 35 kDa xylanase is presented in FIG. 13. The sequence shows an ORF (open reading frame) of 1035 bp, predicting a polypeptide of 344 amino acids, and corresponding to a protein with a molecular weight of about 37.5 kDa. A putative signal processing site is found after alanine 43, and the predicted mature protein has a calculated molecular weight of about 32.9 kDa. The sequence data is thus in good agreement with the 35 kDa xylanase purification and sequencing results described in Examples 3 and 4. The 35 kDa gene sequence appeared identical in all the tested clones, except in the pALK923 DNA. pALK923 contained 93 bp of unknown sequence at the N-terminus of the insert, after which the A. flexuosa 35 kDa xylanase gene sequence started at the location corresponding to base pair 411 in FIG. 13.

The sequence shows high homology towards xylanases from different organisms. At amino acid level, the gene shows about 76% identity towards the *T. fusca* XynA. In addition, the *A. flexuosa* 35 kDa xylanase shows 81% identity with xylan binding domain of the *T. fusca* XynA (Irwing et.al., *Appl. Env. Microbiol.* 60: 763-770 (1995)). Thus, *A. flexuosa* 35 kDa xylanase contains a separate xylan binding domain separated from the catalytic domain by a linker region showing only approximately 40% identity with the linker region of *T. fusca* XynA.

Example 12

Isolation of the 50 kDa *Actinomadura flexuosa* Xylanase Gene

The genomic library of *A. flexuosa* DSM43186 DNA in ZAP Express™ vector was screened using a DNA probe.

Oligonucleotide primers were designed based on the peptide sequences derived from the purified 50 kDa protein. The primer sequences are presented in Table 5. Because the combination of peptide sequences #1696 (SEQ ID NO: 6), #1697 (SEQ ID NO: 7), #1698 (SEQ ID NO: 8) and #1704 (SEQ ID NO: 10) corresponds with 75% similarity to amino acids 42-89 in *Streptomyces lividans* xylanase A, a 39 bp antisense oligo was synthesized, from bases 331 to 369 in the *S. lividans* xlnA sequence. The *S. lividans* xlnA 331-369as probe and the primers #1704 (SEQ ID NO: 10:, #1703as, #1696s were labeled with digoxigenin and terminal transferase, and used as probes in hybridization at 50° C. according to Boehringer, DIG DNA Labeling and Detection Nonradioactive, Applications Manual.

The #1704as and the *S. lividans* xlnA 331-339as probe recognized the same 1.0 kb EcoRI-PstI fragment in *A. flexuosa* DNA. The fragment is different from the 4 kb fragment recognized by the *T. fusca* xynA probe (See Example 9A). Based on these results, the *S. lividans* xlnA 331-369as probe was used to screen the *A. flexuosa* library for the 50 kDa xylanase coding gene.

Three positive plaques were picked after an overnight detection. These clones were named Act.xyl.50/13, Act.xyl.50/14 and Act.xyl.50/15.

The phagemids containing the cloned *A. flexuosa* insert were excised as described in Example 9A. To determine the xylanase activity, the *E. coli* clones were streaked on RBB-xylan+Km plates as described in Example 9A, using the strain producing the *A. flexuosa* 35 kDa xylanase (from plasmid pALK923) as a positive control. The clones Act.xyl.50/13 and Act.xyl.50/14 showed xylanase activity, giving a clear halo around the colony.

TABLE 5

Oligonucleotide primers used in the detection of the gene coding for the A. flexuosa 50 kDa xylanase

| Primer | DNA sequence |
|---|---|
| *Actinomadura* sp. DSM43186 | |
| #1696s | GCA/C/G/TGCA/C/G/TCAA/G/CAC/TAAC/TA/CG |
| #1703as | ACCATA/GTTA/GTAA/C/G/TACA/C/G/TA |
| #1704as | TTCATC/TTCA/GTTC/TTCA/C/G/TGC |
| *S. lividans* xlnA 331-369as | CGTGAGTTCAACATGGTGACGGCCGAGAACGAGATGAAG |
| *S. lividans* xlnA 257-284s | AGAGCGGCCGCTACTTCGGCACCGCCAT |
| *S. lividans* xlnA 530-561as | CACGCCGTTGATGTGGTCGATCATCGCCTGGC | s = sense;
as = antisense

Example 13

Sequencing the Gene for 50 kDa *Actinomadura flexuosa* Xylanase Protein

The phagemid DNAs from the Act.xyl.50/13 and Act.xyl.50/14 were named pALK927 and pALK928, respectively. The *S. lividans* xlnA 331-369as oligomer was used to sequence the *A. flexuosa* insert. In addition, two oligomers corresponding to nucleotides 257-284 and 530-561 in the *S. lividans* xlnA sequence, as well as sequence-specific primers, were synthesized to obtain sequence from the cloned insert. The sequencing reactions were performed with 10% (v/v) DMSO, at the annealing temperature of 58° C. The sequencing was performed as described in Example 11. The sequence of the 1864 bps of the *A. flexuosa* DSM43186 50 kDa xylanase gene is presented in FIG. 14. Peptide sequences obtained from the purified 50 kDa protein are indicated by underlining of the derived amino acid sequence. The derived peptide sequence shows 70-71% identity towards *Actinomadura* sp. FC7 xylanase II (FIG. 15A) and *S. lividans* xylanase A (FIG. 15B) proteins. The sequence shows an ORF of 1479 bps, predicting a polypeptide of 492 amino acids, corresponding to a protein with a molecular weight of about 53.5 kDa.

Example 14

Production of Bacterial (Actinomycetous) Enzymes in *Trichoderma reesei*: Production of *Thermomonospora fusca* Xylanase The expression cassette pALK193 (FIG. 16) was constructed for expression of the *T. fusca* xylanase gene, xynA (Ghangas et al., *J. Bacteriol.* 171:2963-2969 (1989); Irwin et al., *Appl. & Environ. Microbiol.* 60:763-770 (1994)) in *T. reesei*. In the expression cassette, the *T. fusca* xylanase gene is fused to the *T. reesei* cellobiohydrolase 1 (cbh1) signal sequence that is preceeded by the cbh1 promoter. The 9.4 kb pALK193 expression cassette was cut from the vector backbone by EcoRI restriction. It was then isolated, purified and transformed into *T. reesei* ALK02221 strain.

The expression fragment pALK193 contains:

* *T. reesei* cbh1 promoter and signal sequence: The approximately 2.2 kb promoter sequence was derived from the plasmid pAMH110 (EP 244 234-FIG. 15) and was originally isolated from *T. reesei* strain VTT-D-80133 (Teeri et al., *Bio/Technol.* 1: 696-699 (1983)). The sequence of the signal sequence and the promoter area preceding the ATG was published by Shoemaker et al., *Bio/Technology* 1: 691-696 (1983)). In the *T. reesei* strain VTT-D-80133 the sequence preceding the ATG is CCGCGGACTGCGCATC (a SacII site is underlined, an additional cytosine in the DNA sequence, compared to the sequence by Shoemaker et al. *Bio/Technology* 1: 691-696 (1983) is bolded).

To make an exact fusion of the *T. fusca* xynA gene to the cbh1 signal sequence, the 12 nucleotides after the SfiI site in the cbh1 signal sequence and the 5'-end of the *T. fusca* xylanase gene (to the internal MluI site, see FIG. 12 and 16) were synthesized by using polymerase chain reaction (PCR).

* *T. fusca* xylanase gene (xynA): The cloning of the xynA gene is published in Ghangas et al., *J. Bacteriol.* 171:2963-2969 (1989), and the sequence of the gene is published in Irwin et al., *Appl. & Environ. Microbiol.* 60:763-770 (1994). The sequence coding for the mature enzyme was fused (exact fusion) to the cbh1 signal sequence. About a 0.7 kb xynA terminator region, to the SmaI site after the STOP codon of the xynA coding region, precedes the cbh1 terminator fragment in the construction.

* *T. reesei* cbh1 terminator: The 0.7 kb AvaII terminator fragment starting 113 bp before the STOP of the cbh1 gene was added after the *T. fusca* xynA gene, to ensure termination of transcription. The terminator fragment derived from the plasmid pAMH110 (originally isolated from *T. reesei* strain VTT-D-80133; Teeri et al., *Bio/Technol.* 1: 696-699 (1983)) and it contains three TAA codons in all reading frames preceding the terminator fragment (from NdeI site, see EP 244 234).

*A. nidulans* amdS gene: The gene has been isolated from *Aspergillus nidulans* VH1-TRSX6. It encodes acetamidase (Hynes et al., *Mol. Cell. Biol.* 3: 1430-1439 (1983)). Acetamidase enables the strain to grow by using acetamide as the only nitrogen source and this characteristic was used for selecting the transformants. The 3.1 kb fragment (SpeI-XbaI) from the plasmid p3SR2 (Kelly and Hynes, *EMBO J.* 4: 475-479 (1985)) is used in the plasmids. The fragment contains 1007 bps of the promoter area, 1897 bps of the coding region (introns included) and the 183 bps terminator area of the amdS gene.

*T. reesei* cbh1 3'-fragment: The fragment was isolated from *T. reesei* ALK02466 by using plasmid rescue (1.7 kb, BamHI-EcoRI, starting 1.4 kb after the gene's STOP codon, Suominen et al., "High frequency one-step gene replacement in *Trichoderma reesei* II. Effects of deletions of individual cellulase genes," *Mol. Gen Genet.* 241: 523-530 (1993)). Strain ALK02466 derives from the strain ALK0233 (Harkki et al., *Enzyme Microb. Technol.* 13: 227-233 (1991)). The 3'-fragment is used together with the promoter area (described above) to target the *T. fusca* xynA gene to the cbh1 locus by homologous recombination.

Standard DNA methods were used for construction of the vectors (Sambrook et al., "Molecular Cloning: A Laboratory Manual", 2nd ed. Cold Spring Harbor Laboratory Press, Cold Spring Harbor, N.Y., 1989). The restriction enzymes, T4 DNA ligase, Klenow fragment of the DNA polymerase I, T4 DNA polymerase, polynucleotide kinase and Taq polymerase were from Boehringer (Germany) and New England Biolabs (U.S.A.). Each enzyme was used according to the supplier's instructions. Plasmid DNA was isolated by using Qiagen columns (Qiagen GmbH, Germany) or Promega Magic Minipreps (Promega, U.S.A.) according to the manufacturer's protocols. The oligonucleotides used in the PCR-reactions and in sequencing reactions were synthesized by a ABI (Applied Biosystems, U.S.A.) 381A DNA Synthesizer. DNA sequencing was done using ABI kits based on fluorescence-labelled primers, or when sequence-specific primers were used, on fluoresence-labelled dideoxynucleotides, by the Taq cycle sequencing method according to the supplier's instructions. Sequencing reactions were analyzed on an ABI 373A sequencer.

DNA fragments for cloning or transformations were isolated from low-melting-point agarose gels (FMC Bioproducts, U.S.A.) by freeze-thaw-phenol method (Benson, *Biotechniques* 2:66-58 1984) or by using Qiaex II Gel Extraction Kit (Qiagen GmbH, Germany), the GeneClean® or Mermaid Kits™ (Bio 101 Inc., U.S.A.) according to the supplier's instructions.

*T. reesei* ALK02221 was transformed with the isolated 9.4 kb EcoRI expression cassette of pALK193 (FIG. 16) as described by Penttilä et al., *Gene* 61: 155-164 (1987)) with the modifications described in Karhunen et al., *Mol. Gen. Genet* 241: 515-522 (1993). *T. reesei* transformants were transferred on a selective medium and purified through conidia. Transformants were stabilized by growing them on selective slants for two generations prior to sporulating on potato dextrose agar.

The culture supernatants of the transformants were analyzed by measuring the xylanase activity produced, by running samples on SDS-PAGE and by performing Western blots. Polyclonal antibody against *T. fusca* xylanase and purified *T. fusca* xylanase used in the Western blots were obtained from Prof. David Wilson (Cornell University, New York).

The xylanase activity from the culture supernatants was measured at 6.5, 60° C. and with 5 minutes incubation time. Prior to the assay the supernatants were incubated at 60° C. for 20 hours in 50 mM McIlvain's buffer with 200 µg/ml BSA to destroy *T. reesei's* own xylanase activity. *T. fusca* supernatant's xylanase activity was unaffected by the 20 hours' incubation used prior to the reaction but the incubation used did destroy host's xylanase activity. The xylanase activity produced by the best pALK193 transformants was about 900 nkat/ml.

The *T. fusca* xylanase produced by the *T. reesei* transformants was not detectable on SDS-PAGE but was detected on the Western blots. The amount of the *T. fusca* xylanase produced by the transformants, based on the estimation from the Western blots where purified *T. fusca* xylanase was used as a control, was about 50-100 mg/l.

Example 15

Production of Bacterial (Actinomycete) Enzymes in *Trichoderma reesei:* Production of *Trichoderma reesei* β-mannanase and *Actinomadura flexuosa* Xylanase Fusions The *Trichoderma reesei* strains were constructed for *Actinomadura flexuosa* xylanase production (35 kDa xylanase, AM35). Strains overproduce *A. flexuosa* xylanase and are unable to produce *T. reesei's* endoglucanase II and cellobiohydrolase I. Such cellulolytic activity-deficient preparations, and the making of same by recombinant DNA methods, are described in U.S. Pat. No. 5,298,405 incorporated herein by reference or Suominen et al., *Mol. Gen. Genet.* 241: 523-530 (1993). For the overproduction of *A. flexuosa* xylanase, the am35 gene was fused to the *T. reesei* mannanase 1 gene's core/hinge region and the gene fusion was expressed from the strong cbh1 promoter. Different protease cleavage sites were added between the mannanase and xylanase encoding sequences.

The plasmids pALK945, pALK948, pALK1021 and pALK1022 (FIG. 17) containing the sequences SEQ ID NO: 11:, SEQ ID NO: 13:, SEQ ID NO: 15 and SEQ ID NO: 17:, respectively. The plasmids were used in the construction of the *A. flexuosa* xylanase overproducing strains and are otherwise identical to each other, except that the fusion between the man1 core/hinge and am35 sequences differs (see FIG. 19, and below).

The plasmids pALK945, pALK948, pALK1021 and pALK1022 contain the following elements:

* cbh1 (cellobiohydrolase 1) promoter: The promoter is from *Trichoderma reesei* VTT-D-80133 (Teeri et al., *Bio/Technology* 1: 696-699 (1983)). The 2.2 kb EcoRI-SacII fragment (Karhunen et al., *Mol. Gen. Genet.* 241: 515-522 (1993)) is used in the constructs. The sequence preceding the ATG was published by Shoemaker et al., *Bio/Technology* 1: 691-696 (1983)). In the *T. reesei* strain VTT-D-80133 the sequence preceding the ATG is CCGCGGACTGCGCATC (the SacII site is underlined, an additional cytosine in the DNA sequence, compared to the sequence by Shoemaker et al. *Bio/Technology* 1: 691-696 (1983), is bolded).

To make an exact fusion, the 10 nucleotides of the promoter, from the SacII site to the ATG, and the 5'-end of the man1 gene (to the internal ClaI site, see FIG. 17) were synthesized by using polymerase chain reaction (PCR).

* the man1 gene's core/hinge region: The man1 gene codes for β-mannanase that degrades mannans/glucomannans (Stålbrand et al., *Appl. Environ. Microbiol.* 61: 1090-1097 (1995)). The gene has been isolated from *T. reesei* QM6a and its sequence is known (Stålbrand et al., 1995). The 1.35 kb DNA fragment from nucleotides 1 to 1346 coding for the man1 core/hinge region (amino acids from 1 to 379) was used in plasmids pALK945 and pALK948. The DNA fragment from nucleotides 1 to 1359 (amino acids 1 to 383) was used in plasmids pALK1021 and pALK1022. The man1 core/hinge region was linked, from its C-terminal end, to the am35 gene by using the PCR method to obtain four different fusions.

* the am35 gene: The nucleotide sequence and deduced amino acid sequence of the am35 gene encoding a 35 kDa xylanase is presented in FIG. 13. The gene was cloned from a genomic library of *Actinomadura flexuosa* DSM43186 by using a plate activity assay (Example 9A). A 1.3 kb fragment from nucleotide 542 (the N-terminal Asp44) to the MluI site about 250 bps after the end of the gene (pALK1055, FIG. 18) was used in all plasmids. The gene was linked, from its N-terminal end, to the man1 core/hinge sequence by using four different fusions.

* the man1 core/hinge-am35 fusions: man1 core/hinge was fused to the AM35 with or without a KEX-linker sequence, marked as . . . KR . . . , representing . . . Lys-Arg . . . in the list below. The fusion was done by PCR and the following amino acid sequences were formed (see FIG. 19 for the DNA sequences):

| man1 core/hinge + synthetic sequence + am35 sequence | | |
|---|---|---|
| pALK945 | . . .PLYGR*DTT*. . . | = additional R |
| pALK948 | . . .PLYGR*DKRDTT*. . . | = KEX2-linker added |

-continued

| man1 core/hinge + synthetic sequence + am35 sequence | | |
|---|---|---|
| pALK1021 | . . .PLYGQCGG*DTT*. . . | = no new amino acids |
| pALK1022 | . . .PLYGQCGG*RDKRDTT*. . . | = KEX2-linker added |

A NruI restriction site (TCGCGA) was introduced to pALK945 and pALK948 linkers to aid construction of the linkage between the two sequences. This was done by changing the native codon encoding glycine 379 in the man1 core/hinge region (GGC) to a synthetic codon (GGT) and selecting the codon CGC for arginine. The N-terminal Asp44 of the am35 is encoded by GAC.

The fusion sequences were sequenced to ensure that no unwanted alterations had taken place.

The linker sequence used in the plasmid pALK945 has been used in the production of murine anti-2-phenyloxazolone IgG1 antibody from, *T. reesei* as a fusion to the cellobiohydrolase I core/hinge region (WO 92/01797; Nyyssönen et al., *Bio/Technology* 11: 591-595 (1993)). The fusions were cleaved at a low frequency by an extracellular, hitherto uncharacterisized *T. reesei* protease. The cleavage was made after the tyrosine residue in the CBHI linker region, two amino acids before the authentic N-terminus of the heavy chain Fd chain.

The linker sequences in the plasmids pALK948 and pALK1022 carried a synthetic spacer peptide, containing a KEX2-like protein processing signal, preceding the mature *Actinomadura* xylanase.

* the cbh1 terminator: The 739 bp AvaII fragment (Karhunen et al., *Mol. Gen. Genet.* 241:515-522 (1993)) starting 113 bp before the STOP of the cbh1 gene was added after the am35 gene to ensure termination of transcription.

* the amdS gene: The fragment containing the amdS gene was the same as used in the construction of *T. fusca* xynA expression plasmid, see Example 14.

* the cbh1 3'-fragment: The fragment was the same as used in the construction of *T. fusca* xynA expression plasmid, see Example 14. The 3'-fragment is used together with the promoter area (described above) to target the man1-am35 gene fusion to the cbh1 locus by homologous recombination.

Standard DNA methods used in the construction of vectors pALK945, pALK948, pALK1021 and pALK1022 are described in Example 16. The 10.3 kb expression cassette was cut from the vector backbone by EcoRI restriction. The expression cassettes were then isolated, purified and transformed into ALK03620 as described in Example 16, but other *Trichoderma* strains can be used as hosts as well.

In the host strain ALK03620 the endoglucanase 2 (egl2) gene has been replaced by the 3.3 kb BglII-XbaI fragment from the plasmid pAN8-1 (Mattern et al., *Fungal Genet. Newlett.* 35: 25 (1988)). This fragment contains a transformation marker gene, ble from *Streptoalloteichus hindustanus* (Drocourt et al., *Nucl. Acids Res.* 18: 4009 (1990)). The ble gene confers resistance to several antibiotics, e.g. phleomycin and it is, in the construct, expressed from *Aspergillus nidulans* gpdA (glyseraldehyde-3-phosphate-dehydrogenase) promoter, *A. nidulans* trpC terminator is used to terminate the transcription. The replacement was done by using the recombinant DNA methods described in U.S. Pat. No. 5,298,405, incorporated herein by reference.

Example 16

Characteristics of the *Actinomadura flexuosa* Xylanase Producing Transformants

Several purified amdS transformants were grown in shake flasks in a medium containing 4% whey, 1.5% complex nitrogen source derived from grain, 1.5% $KH_2PO_4$ and 0.5% $(NH_4)_2SO_4$. Cultures were maintained at 30° C. and 250 rpm for 7 days. *A. flexuosa* was cultivated in 1 l fermentor as described in Example 1.

The culture supernatants were subjected to SDS-polyacrylamide gel electrophoresis (PAGE). CHBI was detected by Western blotting and immunostaining using a CBHI specific monoclonal antibody (CI-258 (Aho et al., *Eur. J. Biochem.* 200: 643-649 (1991)) and the ProtoBlot Western blot AP system (Promega, U.S.A.) according to the recommendations of the manufacturer.

Some of the CBHI negative transformants were chosen for further characterization: e.g. the recombinant *T. reesei* strains ALKO3620/pALK945/8, ALKO3620/pALK945/6, ALKO3620/pALK948/27, ALKO3620/pALK1021/4 and ALKO3620/pALK1022/29 do not contain the cbh1 gene. The cbh1 gene is replaced by the amdS marker gene and the man1-am35 fusion construct in pALK945, pALK948, pALK1021, pALK1022 expression cassettes. The cbh1 gene replacement was verified in Southern hybridisations. The host strain ALKO3620 used in the transformations is deficient of the egl2 gene (see Example 15) Thus, the strains do not produce *Trichoderma's* cellulase components EGII and CBHI.

Xylanase activities were measured at pH 5.3 and 50° C., with an incubation time of 5 minutes in 50 mM $Na_2HPO_4$ buffer and pH 7 and 70° C., with an incubation time of 5 minutes in 50 mM McIlvain's buffer, containing 100 µg/ml of BSA. The xylanase activity of one transformant per each transformation is presented in Table 6. The corresponding production levels of the transformants as estimated from the specific activity of purified *A. flexuosa* AM35 xylanase (18 000 BXU/mg at pH 7.0 and 70° C.) are shown in Table 6. Another shake flask cultivation was performed which contained two cbh1 negative transformants obtained from the pALK945 transformation. Xylanase activities were measured at pH 7, 70° C. with an incubation time of 60 minutes. Results are presented in Table 6.

The xylanase activity of the *T. reesei* host strain ALKO3620 is about ten times lower at optimum conditions for the AM35 protein (pH 7 and 70° C.) than it is under the conditions optimal for the *T. reesei* xylanase (pH 5.3, 50° C.). The lowest activity and production level was obtained with a transformant containing a fusion construct without any protease processing site (ALKO3620/pALK1021/4).

For the thermal stability determination, samples from the culture supernatants were diluted in 50 mM McIlvain's buffers. BSA was added as a carrier protein to the concentration of 100 µg/ml. The xylanase activity was measured by incubating the enzyme samples at 70° C., pH 7.0 for a period of 0, 15, 30 and 120 minutes after which the xylanase activity of the samples was determined at pH 7, 70° C., using a 5 minutes reaction time. The results are shown in FIG. 20. The thermal stability of the AM35 protein produced by recombinant *T. reesei* strains transformed with the pALK945 and pALK1022 plasmids was identical with *A. flexuosa* xylanase. The AM35 protein produced by pALK948 and pALK1021 transformants was less stable (FIG. 20).

Samples from the culture supernatants were run on polyacrylamide slab gels containing 0.1% SDS on Bio-Rad Mini Protean II electrophoresis system. A polyclonal antibody prepared against the purified β-mannanase (pI 5.4) of *T. reesei* RutC30 (Stålbrand et al., *Appl. Environ. Microbiol.* 61: 1090-1097 (1995)) was used to detect the mannanase in Western blots. In the detection, Promega's ProtoBlot AP System was used. The Western result is shown in FIG. 21. The molecular weight of the β-mannanase protein in the culture medium of the host strain ALKO3620 (lane 5) and of all the transformants (lanes 6-10) is somewhat larger than that of the purified 53 kDa β-mannanase protein sample (Stålbrand et al., *J. Biotechnol.* 29: 229-242 (1993)), (lanes 2 and 3). In addition to the native β-mannanase, the transformants ALKO3620/pALK945/8, ALKO3620/pALK945/6, ALKO3620/pALK948/27 and ALKO3620/pALK1022/29 (lanes 6-9) produce a smaller protein (about 50 kDa) reacts with the polyclonal mannanase antibody. This band represents the shortened mannanase protein obtained from the fusion constructs, and shows that the extracellular proteases have processed the fusion. In the strain ALKO3620/pALK1021/4 (lane 10) two bands with molecular weights of about 70 and

TABLE 6

The xylanase activity and estimated production level of *T. reesei* transformants producing *A. flexuosa* 35 kDa xylanase.

| xylanase | BXU/ml (pH 5.3, 50° C., 5 min) | BXU/ml (pH 7, 70° C., 60 min) | BXU/ml (pH 7, 70° C., 5 min) | AM35 g/l (estimate) |
|---|---|---|---|---|
| *A. flexuosa* culture medium | 190 | ND | 440 | 0.02* |
| ALKO3620 | 3560 | 10 | 360 | 0 |
| ALKO3620/pALK945/6 | ND | 6230 | ND | ND |
| ALKO3620 pALK945/8 | 10970 | 8350 | 14970 | 0.83 |
| ALKO3620/pALK948/27 | 6690 | 7010 | 11920 | 0.66 |
| ALKO3620/pALK1021/4 | 8400 | 6630 | 9800 | 0.54 |
| ALKO3620/pALK1022/29 | 7940 | 7410 | 14870 | 0.83 |

*Total xylanase activity in *A. flexuosa* culture medium.

80 kDa are obtained. These bands originate from the unprocessed fusion protein (MANI core/hinge+AM35 mature protein).

The culture supernatants were analysed also with a polyclonal antibody raised against the purified 35 kDA xylanase of *A. flexuosa* (Example 18). The result is presented in FIG. 22. Transformants ALKO3620/pALK945/6, ALKO3620/pALK948/27 and ALKO3620/pALK10 22/29 showed one to two major bands on the Western blots. These bands were estimated to be 37-39 kDa and migrated parallel to the purified 35 kDa xylanase of *A. flexuosa*. In another transformant obtained from the transformation with pALK945 expression cassette the major band had a molecular weight of 31 kDa. Transformant ALKO3620/pALK1021/4 showed two protein bands of about 70-80 kDa which correlated with the molecular weight of the unprocessed fusion protein. The transformant also produced the processed form of the fusion protein.

When plain actinomycetes xylanase is expressed in *T. reesei* as a fusion of a homologous gene, high production levels of the heterologous protein can be achieved. When *Actinomadura* am35 gene was expressed under the cbh1 promoter as a mannanase fusion, the level of xylanase produced was about 500-800 mg/l (Example 14). When *T. fusca* xynA was expressed in *T. reesei* by linking it to the same promoter (cbh1), without a fusion to homologous gene, only 50-100 mg/i of xylanase was produced (Example 16). Identity between the two actinomycetes xylanases, *Actinomadura* xylanase AM35 and *T. fusca* xylanase A is 76% at amino acid level.

Example 17

Bleaching Experiments Using the *Actinomadura flexuosa* Xylanase Synthesized in *Trichoderma reesei* as a Mannanase Fusion Protein Bleaching experiments were done to determine the usefulness of the *A. flexuosa* AM35 xylanase activity synthesized in *Trichoderma reesei* as a mannanase fusion protein in TCF (totally chlorine free) bleaching of kraft pulp.

The culture media of transformants ALKO3620/pALK945/8, ALKO3620/pALK948/27 and ALKO3620/pALK1022/29 (Example 16) were added to Finnish oxygen delignified softwood kraft pulp (kappa number 16) in the amount of 100 nkat/g pulp dry matter. Xylanase activity was measured at pH 7 and 70° C. with 60 minutes incubation time. The enzyme treatments were done at pH 7 and 80° C. for one hour. Reference pulp was treated in the same way but without enzyme addition. Bleaching was performed using QP sequence. Metals were first removed by chelation with EDTA (chelation stage, Q) and the pulps were then bleached with hydrogen peroxide (peroxide stage, P). The results are shown in Table 7.

TABLE 7

|  | Reference | ALKO3620 pALK945/8 | ALKO3620 pALK948/27 | ALKO3620 pALK1022/29 |
| --- | --- | --- | --- | --- |
| Enzyme treatment |  |  |  |  |
| Consistency, % | 3.5 | 3.5 | 3.5 | 3.5 |
| Retention time, hours | 1 | 1 | 1 | 1 |
| Enzyme dosage, nkat/g | 0 | 100 | 100 | 100 |
| Temperature, ° C., start/end | 81/79 | 82/80 | 80/77 | 83/79 |
| pH, start/end | 7.1/6.9 | 6.9/6.9 | 7.0/7.0 | 7.0/7.3 |
| Chelation stage, Q |  |  |  |  |
| Consistency, % | 3.0 | 3.0 | 3.0 | 3.0 |
| Retention time, hours | 1 | 1 | 1 | 1 |
| EDTA, % of dry matter | 0.2 | 0.2 | 0.2 | 0.2 |
| Temperature at the end, ° C. | 75 | 76 | 74 | 76 |
| pH at the end | 5.2 | 5.1 | 5.0 | 4.9 |
| Peroxide stage, P |  |  |  |  |
| Consistency, | 10 | 10 | 10 | 10 |
| Retention time, hours | 3 | 3 | 3 | 3 |
| Temperature, ° C. | 80 | 80 | 80 | 80 |
| pH, start/end | 11.3/10.8 | 11.4/10.8 | 11.4/10.8 | 11.4/10.9 |
| Peroxide dosage, % | 3.0 | 3.0 | 3.0 | 3.0 |
| Peroxide consumed, % | 2.3 | 2.3 | 2.3 | 2.3 |
| Brightness, % | 64.2 | 66.2 | 65.5 | 65.9 |
| Viscosity, ml/g | 840 | 850 | 850 | 870 |

The use of *A. flexuosa* xylanase activity containing culture media of transformants ALKO3620/pALK945/8, ALKO3620/pALK948/27 and. ALKO3620/pALK1022/29 as a pretreatment of pulp in peroxide bleaching at 80° C. increased the brightness (2 units at its best) of the pulps obtained without increasing the amount of peroxide that was consumed. Viscosity of the pulps was not reduced because of low contaminating cellulase activity in the culture media.

Bleaching experiment was also performed at pH 7 and 70° C. for one hour using the same culture media as above. The brightness values of the final pulps were similar (1.2 units at its best) than when the enzyme pretreatments were performed at pH 7 and 80° C.

Example 18

Purification and Characterization of the Recombinant *Actinomadura flexuosa* 35 kDa Xylanase A 0.5 mg sample of purified 35 kDa xylanase from *A. flexuosa* DSM43186 was sent to Diabor Ltd (Kiviharjuntie 11 A 4, FIN-90220 Oulu, Finland) in order to raise polyclonal antibodies in rabbits. The titer of the produced antibody was good, and a dilution of 1:10.000 was suitable for Western blots.

The protein products of the 35 kDa *A. flexuosa* DSM43186 xylanase gene in *T. reesei* of both ALKO3620/pALK945/8 and ALKO3620/pALK945/6 were identified by running samples of growth medium obtained from fermentor cultivations on SDS-PAGE followed by Western blotting with the wild-type 35 kDa xylanase antibody. Western blotting was performed with the ProtoBlot Western blot AP system (Promega, U.S.A) according to the manufacturer's instructions. Prestained Bio-Rad (LMW-standards) standard proteins were used as molecular mass standards.

The different bands identified from ALKO3620/pALK945/8 depended on growth conditions and growth time. As a whole, five different bands reacted with the 35 kDa xylanase antibody (FIG. 23A). The upper band was estimated to be a 80 kDa protein. The four other band were estimated to be 27, 30, 31 and 34 kDa. *A. flexuosa* (wild type) 35 kDa xylanase was on the same gel estimated to be 39 kDa. Thus, the gene of ALKO36201pALK945/8 did not produce a xylanase band of the same size as the wild-type xylanase. The mass of the upper band, 80 kDa, correlates well with the intact fusion protein. ALKO3620/pALK94516 showed two to three bands on the western blots, also depending on growth conditions (FIG. 23B). The upper band was estimated to about 80 kDa and thus probably the intact fusion protein. The main band on the blots of ALKO3620/pALK945/6 was estimated to 39 kDa and migrated parallel to the wild-type 35 kDa xylanase. Growth medium samples after prolonged growth of the ALKO3620/pALK945/6 strain showed also a faint 31 kDa band on Western blots. The occurrence of smaller size xylanases after prolonged growth of the fungus suggests that post translational modifications, e.g. proteolysis, are present.

The samples of ALKO3620/pALK945/8 and ALKO3620/pALK945/6 above were rerun on SDS-PAGE and blotted on PVDF membrane. The bands obtained were cut out from the PVDF blot and subjected to Edman degradation as described in Example 4. All bands showed the same amino terminal sequence i.e. SEQ ID NO: 5 as the wild-type 35 kDa xylanase (D-T-T-I-T-Q-). Thus, C-terminal modifications must account for the observed differences in molecular masses.

In order to further characterize the gene products of the recombinant 35 kDa *A. flexuosa* xylanase, the different molecular mass xylanases were purified from suitable growth mediums of ALKO3620/pALK945/8 and ALKO3620/pALK945/6. Purification was essentially performed as described in Example 3. Samples of 40 to 150 ml growth medium, depending on the estimated xylanase content, were adjusted to pH 9.1 with 1 M NaOH. The samples were centrifuged at 11.000 g (+4° C. for 20 min). The supernatants were adjusted to 3.7 mS/cm and separately applied on a 5×18 cm DEAE-Sepharose FF (Pharmacia) column equilibrated with 20 mM $Na_2HPO_4$, pH 8.6, at a flow rate of 30 ml/min. Most of the *T. reesei* proteins bound to the DEAE, but the xylanase activity was found in the flow-through.

The flow-through fractions containing xylanase activity were pooled and NaCl was added to 2 M. The pool was applied on a 5×13 cm Phenyl-Sepharose FF (Pharmacia) equilibrated at a flow rate of 20 ml/min with 40 mM $Na2HPO_4$, pH 8.6, containing 2 M NaCl. Elution was performed at a flow rate of 20 ml/min with a gradient from 100% equilibration buffer to 100% 40 mM $Na_2HPO_4$, pH 8.6, in 20 min. The column was further washed with this buffer for 10 min. Elution was continued for 30 min with a gradient from 100% 40 mM $Na_2HPO_4$, pH 8.6, to 100% 40 mM $Na_2HPO_4$, pH 8.6, containing 60% ethylene glycol. Fractions of 10 ml were collected and assayed for xylanase activity, on SDS-PAGE as well as on Western blots. Fractions containing purified xylanases were pooled and stored at −20° C. Wild-type 35 kDa xylanase was purified as above from a 840 ml growth medium sample of *A. flexuosa* (DSM43186).

The purified recombinant *A. flexuosa* xylanases and the wild-type 35 kDa xylanase were run on SDS-PAGE (FIG. 24). From ALKO3620/pALK945/6 a purified 39 kDa xylanase was obtained and from ALKO3620/pALK945/8 a 30 kDa and a 27 kDa xylanase. These, as well as the wild-type 35 kDa xylanase, were subjected to mass spectrometric analysis on a Brucker Biflex Reflector MALDI-TODF (Brucker-Franzeen GmbH, Germany) mass spectrometer. The wild-type 35 kDa xylanase showed a mass of 32 857, in well agreement to the mass calculated from the *A. flexuosa* 35 kDa gene (32 876), Example 11. Thus, wild-type 35 kDa xylanase seems to be unglycosylated. The 39 kDa xylanase from ALKO3620/pALK945/6 gave a mass of 33 429 by mass spectrometry. Since the N-terminal of this sample was identical with the wild-type xylanase, probably either a C-terminal extension or glycosylation accounted for the 572 Da deference in mass. There are no stop codons in the gene sequence, following the wild-type stop codon, which could account for the larger mass of the recombinant xylanase. Thus, probably one or more of the five potential N-glycosylation sites (Asn-X-Ser/Thr, X=/Pro) have been glycosylated in *T. reesei*. The two 30 and 27 kDa xylanases purified from ALKO3620/pALK945/8 had the same N-terminal sequence as the wild-type 35 kDa xylanase. On the mass spectrometer their masses were determined to 23 974 and 21 974 respectively. The estimated molecular masses from SDS-PAGE were thus larger than the masses determined by mass spectrometry. The SDS-PAGE 39 kDa xylanase was renamed to 33.4 kDa and the 30 kDa xylanase to 23.8 kDa and the 27 kDa xylanase to 22 kDa. The wild-type *A. flexuosa* xylanase name was kept as 35 kDa xylanase.

The protein concentration of the purified xylanases was determined at $A_{205}$ by the method of Scopes (Scopes, *Anal. biochem.* 59: 277-287, 1974). The $K_m$ values and the $k_{cat}$ values (based on protein concentration and molecular mass) of the purified xylanases were determined at pH 7 and 70° C. in the substrate range from 2 to 25 mg/ml (birch xylan, Roth 7 500). The $k_{cat}$ values obtained were slightly smaller for both the 35 and 33.4 kDa xylanases as compared to the 22 and 23.8 kDa xylanases (Table 8). However, the $K_m$ values for the 22 and 23.8 kDa xylanases (approximately 10 mg/ml) were 2.5× higher than the corresponding $K_m$ values of the 33.4 and 35 kDa xylanases (approximately 4 mg/ml). As judged from the protein sequence of the 35 kDa gene, the 22 and 23.8 kDa xylanase products miss the C-terminal xylan binding domain (see Example 11) resulting in less efficient binding to xylan. Roughly estimated the 22 kDa form contains only the core domain without the linker region. The 23.8 kDa form contains in addition part of the linker region.

Determination of the pI of the purified xylanases was performed by running samples on a 0.5×20 cm mono P chromatofocusing column (Pharmacia) equilibrated with 0.075 mM Tris-HCl pH 9.3. Elution was performed with polybuffer (10 ml polybuffer in 100 ml water and adjusted to pH 6 with 1 M acetic acid) at a flow rate of 0.5 ml/min and fractions of 0.5 ml were collected. The pH and xylanase activity of the fractions were determined, and the xylanase activity was found in the fraction corresponding to its pI (Table 8).

TABLE 8

| Xylanase Strain | | mass (kDa) | Km (mg/ml) | kcat (1/s) | pI |
|---|---|---|---|---|---|
| 33.4 | ALKO3620/pALK945/6 | 33.429 | 3.8 | 1397 | 8.6 |
| 23.8 | ALKO3620/pALK945/8 | 23.769 | 9.8 | 1525 | 7.6 |

TABLE 8-continued

|  | Xylanase Strain | mass (kDa) | Km (mg/ml) | kcat (1/s) | pI |
|---|---|---|---|---|---|
| 22 | ALKO3620/pALK945/8 | 21.974 | 10.0 | 1682 | 8.2 |
| 35 | DSM43186 | 32.857 | 4.5 | 1135 | 8.5 |

The temperature and pH dependence of the purified xylanases were determined by incubating samples for 60 min with substrate in the pH range of 5.1 to 7.9 and at temperatures of 60, 70 and 80° C., essentially as described in Example 5. From the results, it seems that the full length xylanases, 35 and 33.4 kDa, are slightly more active at higher temperatures and pH than the shorter, 22 and 23.8 kDa, xylanases (FIG. 25).

The purified xylanases were tested for thermal stability by incubating samples at 80° C. and both pH 5 and pH 7 (in 50 mM McIlvains buffer). Samples were withdrawn at suitable time intervals, and the residual activity was measured at pH 7 and 70° C. (5 min incubation time). The half-lives of the xylanases are shown in Table 9. Both 22 and 23.8 kDa xylanases shoved a longer half-life than the full length 33.4 and 35 kDa xylanases under the conditions tested. This stability difference could be a result of the presence of the separate binding domain in the full length xylanases, destabilizing the structure at high temperatures in the absence of substrate. In the temperature dependence experiments (giving slightly different results), the presence of substrate binding to the xylan-binding domain may, on the contrary, stabilize the full length xylanases.

TABLE 9

| Xylanase (kDa) | $t_{1/2}$ (min) (80° C., pH 5) | $t_{1/2}$ (min) (80° C., pH 7) |
|---|---|---|
| 33.4 | 13 | 17 |
| 23.8 | 157 | 95 |
| 22 | 123 | 63 |
| 35 | 32 | 31 |

Apparently the truncations of the 35 kDa xylanase from the C-terminal end has some, but not severe, effects on the kinetic features of this xylanase. A 22 kDa fragment of the 35 kDa xylanase is still active and shows similar kinetics as its longer counterparts.

Example 19

Bleaching Experiments Using Purified 22.0 kDa, 23.8 kDa and 33.4 kDa Forms of AM35 Xylanase from *Actinomadura flexuosa*

The bleach boosting effect of purified forms 22.0 kDa, 23.8 kDa and 33.4 kDa of AM35 xylanase (Example 18) was tested in one stage peroxide bleaching.

The purified forms were added to Finnish oxygen delignified softwood kraft pulp in the amount of 100 nkat/pulp dry matter as such without a protecting agent (results in Table 10) and with *T. reesei* culture medium suitable for protective background (results in Table 11). The xylanase activity of the purified forms as well as the *T. reesei* culture medium were measured at pH 7 70° C. with 5 minutes incubation time. The enzyme treatments were done at pH 8 80° C. for one hour. Reference pulps were treated in the same way but without enzyme addition. Bleachings were performed using QP sequence. Metal ions were first removed by adding EDTA 0.2% of pulp dry matter (chelation stage, Q). The pulps were then bleached with hydrogen peroxide (P) using the following chemicals: 3% $H_2O_2$, 3% NaOH, 0.2% DTPA and 0.5% $MgSO_4$. The conditions of Q and P stages are shown in Tables 10 and 11.

TABLE 10

|  | Reference | 22.0 kDa | 23.8 kDa | 33.4 kDa |
|---|---|---|---|---|
| Enzyme treatment |  |  |  |  |
| Consistency, % | 3.5 | 3.5 | 3.5 | 3.5 |
| Retention time, hours | 1 | 1 | 1 | 1 |
| Enzyme dosage, nkat/g | 0 | 100 | 100 | 100 |
| Temperature, ° C., start/end | 80/79 | 80/79 | 79/79 | 81/80 |
| pH, start/end | 8.3/8.2 | 8.1/8.0 | 8.2/8.1 | 8.2/8.1 |
| Chelation stage, Q |  |  |  |  |
| Consistency, % | 3.0 | 3.0 | 3.0 | 3.0 |
| Retention time, hours | 1 | 1 | 1 | 1 |
| EDTA, % of dry matter | 0.2 | 0.2 | 0.2 | 0.2 |
| Temperature at the end, ° C. | 73 | 73 | 72 | 74 |
| pH at the end | 5.8 | 5.6 | 5.7 | 5.8 |
| Peroxide stage, P |  |  |  |  |
| Consistency, % | 10 | 10 | 10 | 10 |
| Retention time, hours | 3 | 3 | 3 | 3 |
| Temperature, ° C. | 80 | 80 | 80 | 80 |
| pH, start/end | 11.3/10.9 | 11.3/10.8 | 11.3/10.7 | 11.3/10.7 |
| Peroxide dosage, % | 3.0 | 3.0 | 3.0 | 3.0 |
| Peroxide consumed, % | 2.3 | 2.3 | 2.3 | 2.3 |
| Brightness, % | 64.7 | 65.0 | 65.6 | 65.5 |

The 33.4 kDa and 23.8 kDa forms of AM35 xylanase seemed to boost the bleaching effect in peroxide bleaching when pH was 8, temperature 80° C., time one hour and enzyme dosage 100 nkat/g of dry pulp. The 22.0 kDa form did not enhance bleachability probably because of the missing substrate binding domain and incomplete linker region. Generally the increase of brightness was quite small, 0.9 units at its best. This might be due to the fact that the purified enzymes were added as such to 80° C. pulp without any protecting agent or carrier protein, such as *T. reesei* culture medium or BSA.

The second bleaching experiment was carried out the same way as the first one. Only the purified enzyme forms were first mixed with a *T. reesei* culture medium and then added to the pulps. This culture medium was similar to the culture medium from which the enzyme forms were purified. The results are shown in Table 11.

The result of the second bleaching experiment was similar to the first one. The treatments with the 33.4 kDa and 23.8 kDa forms increased brightness about 1.5 units compared with the treatment where only *T. reesei* culture medium was used. Also 22 kDa form gave about 1 unit brightness increase. The results show that the *T. reesei* culture medium worked as a protecting background and 33.4 kDa and 23.8 kDa protein forms, whose linker regions between catalytic and binding domains are intact, increased brightness values more than the 22 kDa form.

TABLE 11

|  | Reference | 22.0 kDa | 23.8 kDA | 33.4 kDa | T. reesei culture medium used as a protection background |
|---|---|---|---|---|---|
| Enzyme treatment |  |  |  |  |  |
| Consistency, % | 3.5 | 3.5 | 3.5 | 3.5 | 3.5 |
| Retention time, hours | 1 | 1 | 1 | 1 | 1 |
| Enzyme dosage, nkat/g | 0 | 100 (+100*) | 100 (+100*) | 100 (+100*) | 100* |
| Temperature, ° C., start/end | 81/80 | 80/80 | 80/80 | 82/82 | 81/80 |
| pH, start/end | 7.9/7.8 | 7.6/7.7 | 7.6/7.7 | 7.6/7.6 | 7.6/7.6 |
| Chelation stage, Q |  |  |  |  |  |
| Consistency, % | 3.0 | 3.0 | 3.0 | 3.0 | 3.0 |
| Retention time, hours | 1 | 1 | 1 | 1 | 1 |
| EDTA, % of dry matter | 0.2 | 0.2 | 0.2 | 0.2 | 0.2 |
| Temperature at the end, ° C. | 76 | 75 | 75 | 76 | 77 |
| pH at the end | 5.2 | 5.2 | 5.2 | 5.2 | 5.1 |
| Peroxide stage, P |  |  |  |  |  |
| Consistency, % | 10 | 10 | 10 | 10 | 10 |
| Retention time, hours | 3 | 3 | 3 | 3 | 3 |
| Temperature, ° C. | 80 | 80 | 80 | 80 | 80 |
| pH, start/end | 11.4/10.7 | 11.4/10.7 | 11.5/10.8 | 11.5/10.8 | 11.6/10.8 |
| Peroxide dosage, % | 3.0 | 3.0 | 3.0 | 3.0 | 3.0 |
| Peroxide consumed, % | 2.2 | 2.3 | 2.3 | 2.3 | 2.3 |
| Brightness, % | 62.1 | 64.1 | 64.6 | 64.5 | 63.0 |

*The xylanase activity is originated in the *T. reesei* culture medium consisting *T. reesei*'s own xylanases.

Example 20

Production of 23.8 kDa form of *Actinomadura flexuosa* 35 kDa xylanase in *Trichoderma reesei*

*T. reesei* strains are constructed for the production of xylanolytically active but shortened, still catalytically active fragments of the full-length actinomycete enzymes. Especially, *T. reesei* strains for the production of the 23.8 kDa form (see example 18) of *A. flexuosa* 35 ka xylanase are constructed. The expression of the shortened form can lead to enhanced xylanase activity in the culture medium.

A recombinant vector encoding a xylanase or a desired domain of it is prepared by fusing the sequence encoding xylanase or a desired domain of it with the sequence of a secretable fungal protein or one or more functional domains of said protein. Especially, the sequence encoding the 23.8 kDa form of the *A. flexuosa* 35 kDa xylanase is fused to *T. reesei* cellulase or hemicellulase as described in U.S. Pat. No. 5,298,405, WO 93/24621 and Stålbrand et al., *Appl. Environ. Microbiol.* 61:1090-1097 (1995) incorporated herein by reference. Especially, the enzyme is selected from the group consisting of CBHI, CBHII, EGI, EGII, XYLI, XYLII and MANI, or a functional domain thereof.

Fusion proteins can be constructed that contain an N-terminal mannanase, xylanase, cellobiohydrolase or endoglucanase core domain or the core and the hinge domains from the same, fused to the *A. flexuosa* xylanase sequence encoding the 23.8 kDa form. The result is a protein that contains N-terminal mannanase, xylanase, cellobiohydrolase or endoglucanase core or core and hinge regions and a C-terminal *A. flexuosa* 23.8 kDa form. The fusion protein contains both the mannanase, xylanase, cellobiohydrolase or endoglucanase and xylanase activities of various domains as provided in the fusion construct.

Fusion proteins can also be constructed such that the mannanase or cellobiohydrolase or endoglucanase tail or a desired fragment thereof, is included, placed before the *A. flexuosa* xylanase sequence, especially so as to allow use of a nonspecific protease site in the tail as a protease site for the recovery of the cellulase sequence from the expressed fusion protein. Alternatively, fusion proteins can be constructed that provide for a protease site in a linker that is placed before the *A. flexuosa* xylanase cellulase, with or without tail sequences.

Example 21

Production of *Thermomonospora fusca* Cellulases in *Trichoderma reesei*

*T. fusca* produces at least six cellulase degrading enzymes, four endoglucanases E1, E2, E4 and E5 and two exocellulases E3 and E6 (Irwin et al., *Biotechnol. and Bioeng.* 42:1002-1013 (1993)). *T. reesei* strains are constructed for efficient production of *T. fusca* cellulases. Especially, *T. reesei* strains are constructed that express *T. fusca* endocellulase, E5. The cloning of the E5 gene is described in Lao et al., *Bacteriol.* 173:3297-3407 (1991).

A recombinant vector encoding a cellulase is prepared by fusing the sequence encoding a polypeptide with cellolytic activity with the sequence of a secretable fungal protein or at least a functional domain of said protein. Especially the *T. fusca* cellulase encoding sequence is fused to *T. reesei* cellulase or hemicellulase or one or more functional domains of said cellulase or hemicellulase, as described in U.S. Pat. No. 5,298,405, WO 93/24621 and Stålbrand et al., *Appl. Environ. Microbiol.* 61: 1090-1097 (1995)) incorporated herein by reference. Especially, the enzyme is selected from the group consisting of CBHI, CBHII, EGI, EGII, XYLI, XYLII and MANI, or a domain thereof, such as secretion signal or the core sequence.

Fusion proteins can be constructed that contain an N-terminal mannanase, xylanase, cellobiohydrolase or endoglucanase core domain or the core and the hinge domains from the same, fused to the *T. fusca* cellulase sequence. The result is a protein that contains N-terminal mannanase, xylanase, cellobiohydrolase or endoglucanase core or core and hinge regions and a C-terminal *T. fusca* cellulase. The fusion protein contains both the mannanase, xylanase, cellobiohydrolase or endoglucanase and cellulase activities of various domains as provided in the fusion construct.

Fusion proteins can also be constructed such that the mannanase or cellobiohydrolase or endoglucanase tail or a desired fragment thereof, is included, placed before the *T. fusca* cellulase sequence, especially so as to allow use of a nonspecific protease site in the tail as a protease site for the recovery of the cellulase sequence from the expressed fusion protein. Alternatively, fusion proteins can be constructed that provide for a protease site in a linker that is placed before the *T. fusca* cellulase, with or without tail sequences.

Example 22

Bacterial Protein Expressed in *Aspergillus*

A recombinant vector encoding a bacterial enzyme is prepared by fusing the enzyme encoding sequence to an *Aspergillus* secretable protein. The protein is preferably *A. niger* or *A. niger* var awamori glucoamylase or α-amylase; or one or more functional domains thereof. (Stoffer et at., *Biochem. J.* 292:197-202 (1993); Svensson et al., Structure-Function relationship in amylases, Ed. R. B. Friedman. *Biotechnology of Amylodextrin Oligosaccharides. ACS Symposium Serium* 458:28-43 (1991); Boel et al., *EMBO J.* 3:1581-1585 (1984), Boel et al., EMBO J. 3: 1097-1102 (1984), Korman et at, *Curr. Genet* 17: 203-212, (1990)

Fusion proteins can be constructed that contain an N-terminal glucoamylase or (X-amylase or one or more functional domains or from the same, fused to a sequence encoding bacterial protein such as *Actinomadura* xylanase. The result is a protein that contains N-terminal glucoamylase or α-amylase or part of them, and a C-terminal *Actinomadura* xylanase. The fusion protein contains both the mannanase or glucoamylase or α-amylase and xylanase activities of the various domains as provided in the fusion construct.

Fusion proteins can also be constructed such that e.g. glucoamylase tail or a desired fragment thereof, is included, placed before the *Actinomadura* xylanase sequence, especially so as to allow use of a nonspecific protease site in the tail as a protease site for the recovery of the xylanase sequence from the expressed fusion protein. Alternatively, fusion proteins can be constructed that provide for a protease site in a linker that is placed before the *Actinomadura* xylanase, with or without tail sequences.

The expression vector uses e.g. *A. niger* glucoamylase promoter. (Boel et al., *EMBO J.* 3:1581-1585 (1984)). The transformation host may be some *Aspergillus niger* strain (Kelly and Hynes, *EMBO J.* 4:475479 (1985)) or for example some *Aspergillus niger* var awamori strain (e.g. ATCC 38854). The chosen *Aspergillus* strain is transformed similar to that described by Kelly and Hynes, *EMBO J.* 4:475-479 (1985)).

The *Actinomadura* xylanase producing transformants are then characterized similar to Example 16 with modification obvious to a person skilled in the art. The culture medium used may be *Aspergillus* complete medium. (Rowlands et al., *Mol. Gen. Genet.* 126:201-216 (1973)).

All references cited herein are incorporated herein by reference. While this invention has been described in detail and with reference to specific embodiments thereof, it will be apparent to one skilled in the art that various changes and modifications could be made therein without departing from the spirit and scope thereof.

What is claimed is:

1. A recombinant expression vector for production of bacterial enzyme in a *Trichoderma* host, the vector comprising:
   (a) a promoter functional in said *Trichoderma* host and operably linked to a first DNA sequence, wherein said first DNA sequence encodes a signal sequence functional in said *Trichoderma* host and a functional domain or functional domains of the native amino acid sequence of *Trichoderma reesei* mannanase I (MANI), *Trichoderma reesei* cellobiohydrolase I (CBHI), *Trichoderma reesei* cellobiohydrolase II (CBHII), *Trichoderma reesei* endoglucanase I (EGI), or *Trichoderma reesei* endoglucanase II (EGII),
   wherein said functional domain or domains of said MANI consist of the native *T. reesei* amino acid sequence of:
      (1) the core domain of said MANI,
      (2) said MANI core domain and the hinge domain of said MANI,
      (3) the tail domain of said MANI, or
      (4) said MANI tail domain and said MANI hinge domain;
   wherein said functional domain or said domains of said CBHI consist of the native *T. reesei* amino acid sequence of:
      (1) the tail domain of said CBHI, or
      (2) the tail and hinge domains of said CBHI,
   wherein said functional domain or domains of said CBHII consist of the native *T. reesei* amino acid sequence of:
      (1) the core domain of said CBHII,
      (2) the core and hinge domains of said CBHII,
      (3) the tail domain of said CBHII, or
      (4) the tail and hinge domain of said CBHII,
   wherein said functional domain or domains of said EGI consist of the native *T. reesei* amino acid sequence of:
      (1) the core domain of said EGI,
      (2) the core and hinge domains of said EGI,
      (3) the tail domain of said EGI, or
      (4) the tail and hinge domain of said EGI;
   wherein said functional domain or domains of said EGII consist of the native *T reesei* amino acid sequence of:
      (1) the core domain of said EGII,
      (2) the core and hinge domains of said EGII,
      (3) the tail domain of said EGII, or
      (4) the tail and hinge domain of said EGII,
   and
   (b) a second DNA sequence which is fused in frame to said first DNA sequence, wherein said second DNA sequence encodes a bacterial enzyme
   wherein said domain or domains result in said bacterial enzyme being secreted from said host at levels that are higher than the levels achieved under the same conditions but using a recombinant expression vector that lacks said DNA sequence encoding said functional domain or domains.

2. The vector of claim 1, wherein said functional domains are said core and hinge domains of said *Trichoderma reesei* MANI.

3. The vector of claim 1, wherein said functional domain is said tail domain of said *Trichoderma reesei* MANI.

4. The vector of claim 1, wherein said functional domain is said tail domain of said *Trichoderma reesei* CBHI, CBHII, EGI, or EGII.

5. The vector of claim 1, wherein said enzyme encoded by said second DNA sequence is derived from an actinomycetes bacteria.

6. The vector of claim 1, wherein said bacterial enzyme is a catalytically active fragment of a full-length bacterial enzyme.

7. The vector of claim 1, wherein said bacterial enzyme is produced at levels that are at least 50-fold higher than the production levels achieved using the actinomycetes bacteria from which the bacterial enzyme is normally expressed.

8. The vector of claim 1, wherein said *Trichoderma* host is *Trichoderma reesei* (*T. reesei*).

9. The vector of claim 1, wherein said promoter is the *Trichoderma reesei* cbh1 promoter.

10. The vector of claim 1, wherein said bacterial enzyme is a xylanase.

11. The vector of claim 1, wherein said functional domain is said core domain of said MANI.

12. The vector of claim 1, wherein said functional domain is said core domain of said CBHII.

13. The vector of claim 1, wherein said functional domains are said core and hinge domains of said CBHII.

14. The vector of claim 1, wherein said functional domain is said core domain of said EGI.

15. The vector of claim 1, wherein said functional domains are said core and hinge domains of said EGI.

16. The vector of claim 1, wherein said functional domain is said core domain of said EGII.

17. The vector of claim 1, wherein said functional domains are said core and hinge domains of said EGII.

18. The vector of claim 1, wherein said functional domains are said tail and hinge domains of said MANI.

19. The vector of claim 1, wherein said functional domain is said tail domain of said CBHI.

20. The vector of claim 1, wherein said functional domains are said tail and hinge domains of said CBHI.

21. The vector of claim 1, wherein said functional domain is said tail domain of said CBHII.

22. The vector of claim 1, wherein said functional domains are said tail and hinge domains of said CBHII.

23. The vector of claim 1, wherein said functional domain is said tail domain of said EGI.

24. The vector of claim 1, wherein said functional domains are said tail and hinge domains of said EGI.

25. The vector of claim 1, wherein said functional domain is said tail domain of said EGII.

26. The vector of claim 1, wherein said functional domains are said tail and hinge domains of said EGII.

27. The vector of claim 1, wherein said bacterial enzyme is *Actinomadura* xylanase and has the amino acid sequence of SEQ ID NO:2.

* * * * *

SEQUENCE LISTING

```
<160> NUMBER OF SEQ ID NOS: 18

<210> SEQ ID NO 1
<211> LENGTH: 1375
<212> TYPE: DNA
<213> ORGANISM: Actinomadura flexuosa (Strain: DSM43186)
<220> FEATURE:
<221> NAME/KEY: CDS
<222> LOCATION: (303)..(1337)
<223> OTHER INFORMATION: Product= AM35 xylanase

<400> SEQUENCE: 1
cccgggtatt  catgtgaatg  attagcaaca  gttatgttac  ggagatattt  ctgagagtgt      60
tgacaggtcg  tgaagtcggt  ccgatacttt  cgagctagct  ccgatagttt  tcgatacgcc     120
ggcacatcga  gcacgtcgga  cgagtcacgc  gccacgtcgg  ttttccgccg  cacgccgcgc     180
agagcggccg  gagaaccccc  gcgtgtccgc  ggcatcggtg  ccggtccgtc  gttcgccgcc     240
gaccgcgcgc  cgggtcgcga  cacgccagcc  cccatcggcc  cttcttcacg  aggaagccgt     300 ac atg aac gaa ccc ctc acc atc acg cag gcc agg cgc cgc aga cgc              347
   Met Asn Glu Pro Leu Thr Ile Thr Gln Ala Arg Arg Arg Arg
   1               5                  10                  15 ctc ggc ctc cgg cgc atc gtc acc agt gcc ttc gcc ctg gca ctc gcc            395
Leu Gly Leu Arg Arg Ile Val Thr Ser Ala Phe Ala Leu Ala Leu Ala
                20                  25                  30 atc gcc ggt gcg ctg ctg ccc ggc acg gcc cac gcc gac acc acc atc            443
Ile Ala Gly Ala Leu Leu Pro Gly Thr Ala His Ala Asp Thr Thr Ile
```

-continued

|  |  |  |  |  |  |  |  |  |  |  |  |  |  |  |  |
|---|---|---|---|---|---|---|---|---|---|---|---|---|---|---|---|
|  |  | 35 |  |  |  | 40 |  |  |  |  | 45 |  |  |  |  |
| acc | aac | cag | acc | ggg | tac | gac | aac | ggc | tac | ttc | tac | tcg | ttc | tgg | 491 |
| Thr | Gln | Asn | Gln | Thr | Gly | Tyr | Asp | Asn | Gly | Tyr | Phe | Tyr | Ser | Phe | Trp |
|  |  | 50 |  |  |  | 55 |  |  |  |  | 60 |  |  |  |  |
| acc | gac | gcg | ccc | ggg | acc | gtc | tcc | atg | acc | ctc | cac | tcg | ggc | ggc | agc | 539 |
| Thr | Asp | Ala | Pro | Gly | Thr | Val | Ser | Met | Thr | Leu | His | Ser | Gly | Gly | Ser |
| 65 |  |  |  |  | 70 |  |  |  |  | 75 |  |  |  |  |  |
| tac | agc | acc | tcg | tgg | cgg | aac | acc | ggg | aac | ttc | gtc | gcc | ggc | aag | ggc | 587 |
| Tyr | Ser | Thr | Ser | Trp | Arg | Asn | Thr | Gly | Asn | Phe | Val | Ala | Gly | Lys | Gly |
| 80 |  |  |  |  | 85 |  |  |  |  | 90 |  |  |  |  | 95 |
| tgg | tcc | acc | ggg | gga | cgg | cgg | acc | gtg | acc | tac | aac | gcc | tcc | ttc | aac | 635 |
| Trp | Ser | Thr | Gly | Gly | Arg | Arg | Thr | Val | Thr | Tyr | Asn | Ala | Ser | Phe | Asn |
|  |  |  |  | 100 |  |  |  |  | 105 |  |  |  |  | 110 |  |
| ccg | tcg | ggt | aac | ggc | tac | ctc | acg | ctc | tac | ggc | tgg | acc | agg | aac | ccg | 683 |
| Pro | Ser | Gly | Asn | Gly | Tyr | Leu | Thr | Leu | Tyr | Gly | Trp | Thr | Arg | Asn | Pro |
|  |  |  |  | 115 |  |  |  |  | 120 |  |  |  |  | 125 |  |
| ctc | gtc | gag | tac | tac | atc | gtc | gag | agc | tgg | ggc | acc | tac | cgg | ccc | acc | 731 |
| Leu | Val | Glu | Tyr | Tyr | Ile | Val | Glu | Ser | Trp | Gly | Thr | Tyr | Arg | Pro | Thr |
|  |  | 130 |  |  |  |  | 135 |  |  |  |  | 140 |  |  |  |
| ggc | acc | tac | aag | ggc | acc | gtc | acc | acc | gac | ggg | gga | acg | tac | gac | atc | 779 |
| Gly | Thr | Tyr | Lys | Gly | Thr | Val | Thr | Thr | Asp | Gly | Gly | Thr | Tyr | Asp | Ile |
|  | 145 |  |  |  |  | 150 |  |  |  |  | 155 |  |  |  |  |
| tac | gag | acc | tgg | cgg | tac | aac | gcg | ccg | tcc | atc | gag | ggc | acc | cgg | acc | 827 |
| Tyr | Glu | Thr | Trp | Arg | Tyr | Asn | Ala | Pro | Ser | Ile | Glu | Gly | Thr | Arg | Thr |
| 160 |  |  |  |  | 165 |  |  |  |  | 170 |  |  |  |  | 175 |
| ttc | cag | cag | ttc | tgg | agc | gtc | cgg | cag | cag | aag | cgg | acc | agc | ggc | acc | 875 |
| Phe | Gln | Gln | Phe | Trp | Ser | Val | Arg | Gln | Gln | Lys | Arg | Thr | Ser | Gly | Thr |
|  |  |  |  | 180 |  |  |  |  | 185 |  |  |  |  | 190 |  |
| atc | acc | atc | ggc | aac | cac | ttc | gac | gcc | tgg | gcc | cgc | gcc | ggc | atg | aac | 923 |
| Ile | Thr | Ile | Gly | Asn | His | Phe | Asp | Ala | Trp | Ala | Arg | Ala | Gly | Met | Asn |
|  |  |  | 195 |  |  |  |  | 200 |  |  |  |  | 205 |  |  |
| ctg | ggc | agc | cac | gac | tac | cag | atc | atg | gcg | acc | gag | ggc | tac | cag | agc | 971 |
| Leu | Gly | Ser | His | Asp | Tyr | Gln | Ile | Met | Ala | Thr | Glu | Gly | Tyr | Gln | Ser |
|  | 210 |  |  |  |  | 215 |  |  |  |  | 220 |  |  |  |  |
| agc | ggt | agc | tcc | acc | gtc | tcc | atc | agc | gag | ggt | ggc | aac | ccc | ggc | aac | 1019 |
| Ser | Gly | Ser | Ser | Thr | Val | Ser | Ile | Ser | Glu | Gly | Gly | Asn | Pro | Gly | Asn |
| 225 |  |  |  |  | 230 |  |  |  |  | 235 |  |  |  |  |  |
| ccg | ggt | aac | ccc | ggc | aac | ccc | ggc | aac | ccc | ggt | aac | ccg | ggt | aac | ccc | 1067 |
| Pro | Gly | Asn | Pro | Gly | Asn | Pro | Gly | Asn | Pro | Gly | Asn | Pro | Gly | Asn | Pro |
| 240 |  |  |  |  | 245 |  |  |  |  | 250 |  |  |  |  | 255 |
| ggc | ggt | ggc | tgc | gtc | gcg | acc | ctc | tcc | gcc | ggc | cag | cag | tgg | agc | gac | 1115 |
| Gly | Gly | Gly | Cys | Val | Ala | Thr | Leu | Ser | Ala | Gly | Gln | Gln | Trp | Ser | Asp |
|  |  |  | 260 |  |  |  |  | 265 |  |  |  |  | 270 |  |  |
| cgc | tac | aac | ctc | aac | gtc | tcg | gtc | agc | ggc | tcg | aac | aac | tgg | acg | gtc | 1163 |
| Arg | Tyr | Asn | Leu | Asn | Val | Ser | Val | Ser | Gly | Ser | Asn | Asn | Trp | Thr | Val |
|  |  |  | 275 |  |  |  |  | 280 |  |  |  |  | 285 |  |  |
| cgg | atg | gac | gtg | ccc | tac | ccg | gcc | cgc | atc | atc | gcc | acc | tgg | aac | atc | 1211 |
| Arg | Met | Asp | Val | Pro | Tyr | Pro | Ala | Arg | Ile | Ile | Ala | Thr | Trp | Asn | Ile |
|  |  | 290 |  |  |  |  | 295 |  |  |  |  | 300 |  |  |  |
| cac | gcc | cag | tgg | ccc | gag | tcc | cag | gtg | ctc | atc | gcc | aga | ccc | aac | ggc | 1259 |
| His | Ala | Gln | Trp | Pro | Glu | Ser | Gln | Val | Leu | Ile | Ala | Arg | Pro | Asn | Gly |
|  | 305 |  |  |  |  | 310 |  |  |  |  | 315 |  |  |  |  |
| aac | ggc | aac | aac | tgg | ggc | gtg | acg | atc | cag | cac | aac | ggc | aac | tgg | acc | 1307 |
| Asn | Gly | Asn | Asn | Trp | Gly | Val | Thr | Ile | Gln | His | Asn | Gly | Asn | Trp | Thr |
| 320 |  |  |  |  | 325 |  |  |  |  | 330 |  |  |  |  | 335 |
| tgg | ccg | acg | gtc | acc | tgt | acc | gcg | aac | tga | gttcccgccc | | ccaaaggtgg | | | | 1357 |
| Trp | Pro | Thr | Val | Thr | Cys | Thr | Ala | Asn |  |  |  |  |  |  |  |
|  |  |  |  | 340 |  |  |  |  |  |  |  |  |  |  |  |
| cgcggcggct | | cccggccg | | | | | | | | | | | | | 1375 |

<210> SEQ ID NO 2
<211> LENGTH: 344
<212> TYPE: PRT
<213> ORGANISM: Actinomadura flexuosa

<400> SEQUENCE: 2

```
Met Asn Glu Pro Leu Thr Ile Thr Gln Ala Arg Arg Arg Arg Leu
1               5                   10                  15

Gly Leu Arg Arg Ile Val Thr Ser Ala Phe Ala Leu Ala Leu Ala Ile
            20                  25                  30

Ala Gly Ala Leu Leu Pro Gly Thr Ala His Ala Asp Thr Thr Ile Thr
            35                  40                  45

Gln Asn Gln Thr Gly Tyr Asp Asn Gly Tyr Phe Tyr Ser Phe Trp Thr
50                  55                  60

Asp Ala Pro Gly Thr Val Ser Met Thr Leu His Ser Gly Gly Ser Tyr
65                  70                  75                  80

Ser Thr Ser Trp Arg Asn Thr Gly Asn Phe Val Ala Gly Lys Gly Trp
                85                  90                  95

Ser Thr Gly Gly Arg Arg Thr Val Thr Tyr Asn Ala Ser Phe Asn Pro
            100                 105                 110

Ser Gly Asn Gly Tyr Leu Thr Leu Tyr Gly Trp Thr Arg Asn Pro Leu
            115                 120                 125

Val Glu Tyr Tyr Ile Val Glu Ser Trp Gly Thr Tyr Arg Pro Thr Gly
130                 135                 140

Thr Tyr Lys Gly Thr Val Thr Thr Asp Gly Gly Thr Tyr Asp Ile Tyr
145                 150                 155                 160

Glu Thr Trp Arg Tyr Asn Ala Pro Ser Ile Glu Gly Thr Arg Thr Phe
                165                 170                 175

Gln Gln Phe Trp Ser Val Arg Gln Gln Lys Arg Thr Ser Gly Thr Ile
            180                 185                 190

Thr Ile Gly Asn His Phe Asp Ala Trp Ala Arg Ala Gly Met Asn Leu
            195                 200                 205

Gly Ser His Asp Tyr Gln Ile Met Ala Thr Glu Gly Tyr Gln Ser Ser
210                 215                 220

Gly Ser Ser Thr Val Ser Ile Ser Glu Gly Gly Asn Pro Gly Asn Pro
225                 230                 235                 240

Gly Asn Pro Gly Asn Pro Gly Asn Pro Gly Asn Pro Gly Asn Pro Gly
                245                 250                 255

Gly Gly Cys Val Ala Thr Leu Ser Ala Gly Gln Gln Trp Ser Asp Arg
            260                 265                 270

Tyr Asn Leu Asn Val Ser Val Ser Gly Ser Asn Asn Trp Thr Val Arg
            275                 280                 285

Met Asp Val Pro Tyr Pro Ala Arg Ile Ile Ala Thr Trp Asn Ile His
290                 295                 300

Ala Gln Trp Pro Glu Ser Gln Val Leu Ile Ala Arg Pro Asn Gly Asn
305                 310                 315                 320

Gly Asn Asn Trp Gly Val Thr Ile Gln His Asn Gly Asn Trp Thr Trp
                325                 330                 335

Pro Thr Val Thr Cys Thr Ala Asn
            340
```

<210> SEQ ID NO 3
<211> LENGTH: 1864
<212> TYPE: DNA

<213> ORGANISM: Actinomadura flexuosa (Strain: DSM43186)
<220> FEATURE:
<221> NAME/KEY: CDS
<222> LOCATION: (194)..(1672)
<223> OTHER INFORMATION: Product= AM50 xylanase

<400> SEQUENCE: 3

```
ttcggcagcc tattgacaaa tttcgtgaat gtttcccaca cttgctctgc agacggcccc      60
gccgatcatg ggtgcaccgg tcggcgggac cgtgctccga cgccattcgg gggtgtgcgc     120
ctgcgggcgc ggcgtcgatc ccgcggggac tcccgcggtt cccttccgt gtccctctaa      180 tggaggctca ggc atg ggc gtg aac gcc ttc ccc aga ccc gga gct cgg        229
             Met Gly Val Asn Ala Phe Pro Arg Pro Gly Ala Arg
               1               5                  10 cgg ttc acc ggc ggg ctg tac cgg gcc ctg gcc gcg gcc acg gtg agc       277
Arg Phe Thr Gly Gly Leu Tyr Arg Ala Leu Ala Ala Ala Thr Val Ser
           15                  20                  25 gtg gtc ggc gtg gtc acg gcc ctg acg gtg acc cag ccc gcc agc gcc       325
Val Val Gly Val Val Thr Ala Leu Thr Val Thr Gln Pro Ala Ser Ala
 30                  35                  40 gcg gcg agc acg ctc gcc gag ggt gcc gcg cag cac aac cgg tac ttc       373
Ala Ala Ser Thr Leu Ala Glu Gly Ala Ala Gln His Asn Arg Tyr Phe
45                  50                  55                  60 ggc gtg gcc atc gcc gcg aac agg ctc acc gac tcg gtc tac acc aac       421
Gly Val Ala Ile Ala Ala Asn Arg Leu Thr Asp Ser Val Tyr Thr Asn
                65                  70                  75 atc gcg aac cgc gag ttc aac tcg gtg acg gcc gag aac gag atg aag       469
Ile Ala Asn Arg Glu Phe Asn Ser Val Thr Ala Glu Asn Glu Met Lys
             80                  85                  90 atc gac gcc acc gag ccg cag cag ggg cgg ttc gac ttc acc cag gcc       517
Ile Asp Ala Thr Glu Pro Gln Gln Gly Arg Phe Asp Phe Thr Gln Ala
         95                 100                 105 gac cgg atc tac aac tgg gcg cgc cag aac ggc aag cag gtc cgc ggc       565
Asp Arg Ile Tyr Asn Trp Ala Arg Gln Asn Gly Lys Gln Val Arg Gly
     110                 115                 120 cac acc ctg gcc tgg cac tcg cag cag ccg cag tgg atg cag aac ctc       613
His Thr Leu Ala Trp His Ser Gln Gln Pro Gln Trp Met Gln Asn Leu
125                 130                 135                 140 agc ggc cag gcg ctg cgc cag gcg atg atc aac cac atc cag ggg gtc       661
Ser Gly Gln Ala Leu Arg Gln Ala Met Ile Asn His Ile Gln Gly Val
                145                 150                 155 atg tcc tac tac cgg ggc aag atc ccg atc tgg gac gtg gtg aac gag       709
Met Ser Tyr Tyr Arg Gly Lys Ile Pro Ile Trp Asp Val Val Asn Glu
             160                 165                 170 gcg ttc gag gac gga aac tcc ggc cgc cgg tgc gac tcc aac ctc cag       757
Ala Phe Glu Asp Gly Asn Ser Gly Arg Arg Cys Asp Ser Asn Leu Gln
         175                 180                 185 cgc acc ggt aac gat tgg atc gag gtc gcg ttc cgc acc gcc cgc cag       805
Arg Thr Gly Asn Asp Trp Ile Glu Val Ala Phe Arg Thr Ala Arg Gln
     190                 195                 200 ggg gac ccc tcg gcc aag ctc tgc tac aac gac tac aac atc gag aac       853
Gly Asp Pro Ser Ala Lys Leu Cys Tyr Asn Asp Tyr Asn Ile Glu Asn
205                 210                 215                 220 tgg aac gcg gcc aag acc cag gcg gtc tac aac atg gtg cgg gac ttc       901
Trp Asn Ala Ala Lys Thr Gln Ala Val Tyr Asn Met Val Arg Asp Phe
                225                 230                 235 aag tcc cgc ggc gtg ccc atc gac tgc gtg ggc ttc cag tcg cac ttc       949
Lys Ser Arg Gly Val Pro Ile Asp Cys Val Gly Phe Gln Ser His Phe
             240                 245                 250 aac agc ggt aac ccg tac aac ccg aac ttc cgc acc acc ctg cag cag       997
```

```
                Asn Ser Gly Asn Pro Tyr Asn Pro Asn Phe Arg Thr Thr Leu Gln Gln
                        255                 260                 265 ttc gcg gcc ctc ggc gtg gac gtc gag gtc acc gag ctg gac atc gag          1045
Phe Ala Ala Leu Gly Val Asp Val Glu Val Thr Glu Leu Asp Ile Glu
        270                 275                 280 aac gcc ccg gcc cag acc tac gcc agc gtg atc cgg gac tgc ctg gcc          1093
Asn Ala Pro Ala Gln Thr Tyr Ala Ser Val Ile Arg Asp Cys Leu Ala
285                 290                 295                 300 gtg gac cgc tgc acc ggc atc acc gtc tgg ggt gtc cgc gac agc gac          1141
Val Asp Arg Cys Thr Gly Ile Thr Val Trp Gly Val Arg Asp Ser Asp
                305                 310                 315 tcc tgg cgc tcg tac cag aac ccg ctg ctg ttc gac aac aac ggc aac          1189
Ser Trp Arg Ser Tyr Gln Asn Pro Leu Leu Phe Asp Asn Asn Gly Asn
            320                 325                 330 aag aag cag gcc tac tac gcg gtg ctc gac gcc ctg aac gag ggc tcc          1237
Lys Lys Gln Ala Tyr Tyr Ala Val Leu Asp Ala Leu Asn Glu Gly Ser
        335                 340                 345 gac gac ggt ggc ggc ccg tcc aac ccg ccg gtc tcg ccg ccg ccg ggt          1285
Asp Asp Gly Gly Gly Pro Ser Asn Pro Pro Val Ser Pro Pro Pro Gly
    350                 355                 360 ggc ggt tcc ggg cag atc cgg ggc gtg gcc tcc aac cgg tgc atc gac          1333
Gly Gly Ser Gly Gln Ile Arg Gly Val Ala Ser Asn Arg Cys Ile Asp
365                 370                 375                 380 gtg ccg aac ggc aac acc gcc gac ggc acc cag gtc cag ctg tac gac          1381
Val Pro Asn Gly Asn Thr Ala Asp Gly Thr Gln Val Gln Leu Tyr Asp
                385                 390                 395 tgc cac agc ggt tcc aac cag cag tgg acc tac acc tcg tcc ggt gag          1429
Cys His Ser Gly Ser Asn Gln Gln Trp Thr Tyr Thr Ser Ser Gly Glu
            400                 405                 410 ttc cgc atc ttc ggc aac aag tgc ctg gac gcg ggc ggc tcc agc aac          1477
Phe Arg Ile Phe Gly Asn Lys Cys Leu Asp Ala Gly Gly Ser Ser Asn
        415                 420                 425 ggt gcg gtg gtc cag atc tac agc tgc tgg ggc ggc gcc aac cag aag          1525
Gly Ala Val Val Gln Ile Tyr Ser Cys Trp Gly Gly Ala Asn Gln Lys
    430                 435                 440 tgg gag ctc cgg gcc gac ggc acc atc gtg ggc gtg cag tcc ggg ctg          1573
Trp Glu Leu Arg Ala Asp Gly Thr Ile Val Gly Val Gln Ser Gly Leu
445                 450                 455                 460 tgc ctc gac gcg gtg ggt ggc ggc acc ggc aac ggc acg cgg ctg cag          1621
Cys Leu Asp Ala Val Gly Gly Gly Thr Gly Asn Gly Thr Arg Leu Gln
                465                 470                 475 ctc tac tcc tgc tgg ggc ggc aac aac cag aag tgg tcc tac aac gcc          1669
Leu Tyr Ser Cys Trp Gly Gly Asn Asn Gln Lys Trp Ser Tyr Asn Ala
            480                 485                 490 tga tccccggctg atcgaccta gttgaggccg tctccggtac ggcaccgtcg                1722
gaccggaggc ggtcccttgt tcgtccagga cggaaggacc ggtctgagca ggcgcggcga       1782
tcggacacca tggtgggagg cacgaaagcg ggaggggggtc gtattccgag actccgggaa      1842
gtggaggtgt tcctccacct ga                                                1864

<210> SEQ ID NO 4
<211> LENGTH: 492
<212> TYPE: PRT
<213> ORGANISM: Actinomadura flexuosa

<400> SEQUENCE: 4

Met Gly Val Asn Ala Phe Pro Arg Pro Gly Ala Arg Arg Phe Thr Gly
1               5                   10                  15
```

-continued

```
Gly Leu Tyr Arg Ala Leu Ala Ala Ala Thr Val Ser Val Val Gly Val
             20                  25                  30

Val Thr Ala Leu Thr Val Thr Gln Pro Ala Ser Ala Ala Ala Ser Thr
         35                  40                  45

Leu Ala Glu Gly Ala Ala Gln His Asn Arg Tyr Phe Gly Val Ala Ile
     50                  55                  60

Ala Ala Asn Arg Leu Thr Asp Ser Val Tyr Thr Asn Ile Ala Asn Arg
 65                  70                  75                  80

Glu Phe Asn Ser Val Thr Ala Glu Asn Glu Met Lys Ile Asp Ala Thr
                 85                  90                  95

Glu Pro Gln Gln Gly Arg Phe Asp Phe Thr Gln Ala Asp Arg Ile Tyr
            100                 105                 110

Asn Trp Ala Arg Gln Asn Gly Lys Gln Val Arg Gly His Thr Leu Ala
        115                 120                 125

Trp His Ser Gln Gln Pro Gln Trp Met Gln Asn Leu Ser Gly Gln Ala
    130                 135                 140

Leu Arg Gln Ala Met Ile Asn His Ile Gln Gly Val Met Ser Tyr Tyr
145                 150                 155                 160

Arg Gly Lys Ile Pro Ile Trp Asp Val Val Asn Glu Ala Phe Glu Asp
                165                 170                 175

Gly Asn Ser Gly Arg Arg Cys Asp Ser Asn Leu Gln Arg Thr Gly Asn
            180                 185                 190

Asp Trp Ile Glu Val Ala Phe Arg Thr Ala Arg Gln Gly Asp Pro Ser
        195                 200                 205

Ala Lys Leu Cys Tyr Asn Asp Tyr Asn Ile Glu Asn Trp Asn Ala Ala
    210                 215                 220

Lys Thr Gln Ala Val Tyr Asn Met Val Arg Asp Phe Lys Ser Arg Gly
225                 230                 235                 240

Val Pro Ile Asp Cys Val Gly Phe Gln Ser His Phe Asn Ser Gly Asn
                245                 250                 255

Pro Tyr Asn Pro Asn Phe Arg Thr Thr Leu Gln Gln Phe Ala Ala Leu
            260                 265                 270

Gly Val Asp Val Glu Val Thr Glu Leu Asp Ile Glu Asn Ala Pro Ala
        275                 280                 285

Gln Thr Tyr Ala Ser Val Ile Arg Asp Cys Leu Ala Val Asp Arg Cys
    290                 295                 300

Thr Gly Ile Thr Val Trp Gly Val Arg Asp Ser Asp Ser Trp Arg Ser
305                 310                 315                 320

Tyr Gln Asn Pro Leu Leu Phe Asp Asn Gly Asn Lys Lys Gln Ala
                325                 330                 335

Tyr Tyr Ala Val Leu Asp Ala Leu Asn Glu Gly Ser Asp Gly Gly
            340                 345                 350

Gly Pro Ser Asn Pro Pro Val Ser Pro Pro Gly Gly Ser Gly
        355                 360                 365

Gln Ile Arg Gly Val Ala Ser Asn Arg Cys Ile Asp Val Pro Asn Gly
    370                 375                 380

Asn Thr Ala Asp Gly Thr Gln Val Gln Leu Tyr Asp Cys His Ser Gly
385                 390                 395                 400

Ser Asn Gln Gln Trp Thr Tyr Thr Ser Ser Gly Glu Phe Arg Ile Phe
                405                 410                 415

Gly Asn Lys Cys Leu Asp Ala Gly Gly Ser Ser Asn Gly Ala Val Val
            420                 425                 430
```

```
Gln Ile Tyr Ser Cys Trp Gly Gly Ala Asn Gln Lys Trp Glu Leu Arg
        435                 440                 445

Ala Asp Gly Thr Ile Val Gly Val Gln Ser Gly Leu Cys Leu Asp Ala
    450                 455                 460

Val Gly Gly Gly Thr Gly Asn Gly Thr Arg Leu Gln Leu Tyr Ser Cys
465                 470                 475                 480

Trp Gly Gly Asn Asn Gln Lys Trp Ser Tyr Asn Ala
                485                 490

<210> SEQ ID NO 5
<211> LENGTH: 6
<212> TYPE: PRT
<213> ORGANISM: Actinomadura flexuosa (Strain: DM43186)
<220> FEATURE:
<221> NAME/KEY: PEPTIDE
<222> LOCATION: (1)..(6)
<223> OTHER INFORMATION: Label= AM35_N-term

<400> SEQUENCE: 5

Asp Thr Thr Ile Thr Gln
1               5

<210> SEQ ID NO 6
<211> LENGTH: 14
<212> TYPE: PRT
<213> ORGANISM: Actinomadura flexuosa (Strain: DM43186)
<220> FEATURE:
<221> NAME/KEY: PEPTIDE
<222> LOCATION: (1)..(14)
<223> OTHER INFORMATION: Label= AM50_1696_pep

<400> SEQUENCE: 6

Ala Ala Ser Thr Leu Ala Glu Gly Ala Ala Gln His Asn Arg
1               5                   10

<210> SEQ ID NO 7
<211> LENGTH: 10
<212> TYPE: PRT
<213> ORGANISM: Actinomadura flexuosa (Strain: DM43186)
<220> FEATURE:
<221> NAME/KEY: PEPTIDE
<222> LOCATION: (1)..(10)
<223> OTHER INFORMATION: Label= AM50_1697_pep

<400> SEQUENCE: 7

Tyr Phe Gly Val Ala Ile Ala Ala Asn Arg
1               5                   10

<210> SEQ ID NO 8
<211> LENGTH: 12
<212> TYPE: PRT
<213> ORGANISM: Actinomadura flexuosa (STRAIN: DSM43186)
<220> FEATURE:
<221> NAME/KEY: PEPTIDE
<222> LOCATION: (1)..(12)
<223> OTHER INFORMATION: Label= AM50_1698_pep

<400> SEQUENCE: 8

Leu Asn Asp Ser Val Tyr Thr Asn Ile Ala Asn Arg
1               5                   10

<210> SEQ ID NO 9
<211> LENGTH: 9
<212> TYPE: PRT
<213> ORGANISM: Actinomadura flexuosa (STRAIN: DSM43186)
```

```
<220> FEATURE:
<221> NAME/KEY: PEPTIDE
<222> LOCATION: (1)..(9)
<223> OTHER INFORMATION: Label= AM50_1699_pep
<220> FEATURE:
<221> NAME/KEY: Misc_feature
<222> LOCATION: (1)
<223> OTHER INFORMATION: Xaa can be any amino acid
<220> FEATURE:
<221> NAME/KEY: Misc_feature
<222> LOCATION: (7)
<223> OTHER INFORMATION: Xaa can be any amino acid

<400> SEQUENCE: 9

Xaa Thr Gly Ile Thr Val Xaa Gly Val
1               5

<210> SEQ ID NO 10
<211> LENGTH: 11
<212> TYPE: PRT
<213> ORGANISM: Actinomadura flexuosa (STRAIN: DSM43186)
<220> FEATURE:
<221> NAME/KEY: PEPTIDE
<222> LOCATION: (1)..(11)
<223> OTHER INFORMATION: Label= AM50_1704_pep

<400> SEQUENCE: 10

Glu Phe Asn Ser Val Thr Ala Glu Asn Glu Met
1               5                   10

<210> SEQ ID NO 11
<211> LENGTH: 18
<212> TYPE: DNA
<213> ORGANISM: Trichoderma reesei and Actinomadura flexuosa (STRAIN:
      QM6a and DSM43186)
<220> FEATURE:
<221> NAME/KEY: CDS
<222> LOCATION: (1)..(18)
<223> OTHER INFORMATION: Partial sequence of the fusion in pALK945.
      Bases 1-5 are bases 1342-1346 of T.reesei man1 sequence, bases 6-9
      synthetic and bases 10-18 are bases 432-440 of A. flexuosa AM35
      sequence.

<400> SEQUENCE: 11 tat ggt cgc gac acc acc                                            18
Tyr Gly Arg Asp Thr Thr
1               5

<210> SEQ ID NO 12
<211> LENGTH: 6
<212> TYPE: PRT
<213> ORGANISM: Trichoderma reesei and Actinomadura flexuosa

<400> SEQUENCE: 12

Tyr Gly Arg Asp Thr Thr
1               5

<210> SEQ ID NO 13
<211> LENGTH: 27
<212> TYPE: DNA
<213> ORGANISM: Trichoderma reesei and Actinomadura flexuosa (STRAIN:
      QM6a and DSM43186)
<220> FEATURE:
<221> NAME/KEY: CDS
<222> LOCATION: (1)..(27)
<223> OTHER INFORMATION: Partial sequence of the fusion in pALK948.
      Bases 1-5 are bases 1342-1346 of T.reesei man1 sequence, bases
      6-18 are synthetic KEX2-linker, bases are 19-27 are bases 432-440
      of A. flexuosa AM35 sequence
```

```
<400> SEQUENCE: 13 tat ggt cgc gac aag cgc gac acc acc                          27
Tyr Gly Arg Asp Lys Arg Asp Thr Thr
1               5

<210> SEQ ID NO 14
<211> LENGTH: 9
<212> TYPE: PRT
<213> ORGANISM: Trichoderma reesei and Actinomadura flexuosa

<400> SEQUENCE: 14

Tyr Gly Arg Asp Lys Arg Asp Thr Thr
1               5

<210> SEQ ID NO 15
<211> LENGTH: 39
<212> TYPE: DNA
<213> ORGANISM: Trichoderma reesei and Actinomadura flexuosa (STRAIN:
      QM6a and DSM43186)
<220> FEATURE:
<221> NAME/KEY: CDS
<222> LOCATION: (1)..(39)
<223> OTHER INFORMATION: Partial sequence of the fusion in pALK1021.
      Bases 1-18 are bases 1342-1359 of T.reesei man1 sequence, and
      bases 19-39 are bases 432-452 of A. flexuosa AM35 sequence

<400> SEQUENCE: 15 tat ggc cag tgt gga ggt gac acc acc atc acc cag aac          39
Tyr Gly Gln Cys Gly Gly Asp Thr Thr Ile Thr Gln Asn
1               5                   10

<210> SEQ ID NO 16
<211> LENGTH: 13
<212> TYPE: PRT
<213> ORGANISM: Trichoderma reesei and Actinomadura flexuosa

<400> SEQUENCE: 16

Tyr Gly Gln Cys Gly Gly Asp Thr Thr Ile Thr Gln Asn
1               5                   10

<210> SEQ ID NO 17
<211> LENGTH: 39
<212> TYPE: DNA
<213> ORGANISM: Trichoderma reesei and Actinomadura flexuosa (STRAIN:
      QM6a and DSM43186)
<220> FEATURE:
<221> NAME/KEY: CDS
<222> LOCATION: (1)..(39)
<223> OTHER INFORMATION: Partial sequence of the fusion in pALK1022.
      Bases 1-18 are bases 1342-1359 of T.reesei man1 sequence, bases
      19-30 are synthetic KEX2-linker, bases 31-39 are bases 432-440 of
      A. flexuosa AM35 sequence

<400> SEQUENCE: 17 tat ggc cag tgt gga ggt cgc gac aag cgc gac acc acc          39
Tyr Gly Gln Cys Gly Gly Arg Asp Lys Arg Asp Thr Thr
1               5                   10

<210> SEQ ID NO 18
<211> LENGTH: 13
<212> TYPE: PRT
<213> ORGANISM: Trichoderma reesei and Actinomadura flexuosa

<400> SEQUENCE: 18

Tyr Gly Gln Cys Gly Gly Arg Asp Lys Arg Asp Thr Thr
1               5                   10
```